United States Patent
Embrey et al.

(10) Patent No.: US 9,714,243 B2
(45) Date of Patent: Jul. 25, 2017

(54) 4-PYRIDINONETRIAZINE DERIVATIVES AS HIV INTEGRASE INHIBITORS

(71) Applicant: Merck Sharp & Dohme Corp., Rahway, NJ (US)

(72) Inventors: Mark W. Embrey, Harleysville, PA (US); Thomas H. Graham, Scotch Plains, NJ (US); Abbas Walji, Lansdale, PA (US); Sherman T. Waddell, Wesetfield, NJ (US); Tao Yu, Edison, NJ (US); Yonglian Zhang, Metuchen, NJ (US); Wensheng Liu, Edison, NJ (US); Paul J. Coleman, Harleysville, PA (US); John Wai, Harleysville, PA (US); Thomas Steele, Schwenksville, PA (US); Christina Di Marco, Lafayette Hill, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/652,580

(22) PCT Filed: Dec. 12, 2013

(86) PCT No.: PCT/US2013/074590
§ 371 (c)(1),
(2) Date: Jun. 16, 2015

(87) PCT Pub. No.: WO2014/099586
PCT Pub. Date: Jun. 26, 2014

(65) Prior Publication Data
US 2015/0329539 A1 Nov. 19, 2015

Related U.S. Application Data

(60) Provisional application No. 61/738,112, filed on Dec. 17, 2012.

(51) Int. Cl.
| | | |
|---|---|---|
| *C07D 471/04* | (2006.01) |
| *A61K 31/53* | (2006.01) |
| *C07D 471/10* | (2006.01) |
| *C07F 9/6521* | (2006.01) |
| *A61K 31/675* | (2006.01) |
| *A61K 31/55* | (2006.01) |
| *A61K 31/4985* | (2006.01) |
| *A61K 45/06* | (2006.01) |
| *C07D 471/14* | (2006.01) |
| *C07D 471/20* | (2006.01) |
| *C07D 491/20* | (2006.01) |
| *C07D 495/20* | (2006.01) |
| *C07D 498/14* | (2006.01) |

(52) U.S. Cl.
CPC ........ *C07D 471/04* (2013.01); *A61K 31/4985* (2013.01); *A61K 31/53* (2013.01); *A61K 31/55* (2013.01); *A61K 31/675* (2013.01); *A61K 45/06* (2013.01); *C07D 471/10* (2013.01); *C07D 471/14* (2013.01); *C07D 471/20* (2013.01); *C07D 491/20* (2013.01); *C07D 495/20* (2013.01); *C07D 498/14* (2013.01); *C07F 9/6521* (2013.01)

(58) Field of Classification Search
CPC .................................................. C07D 400/12
See application file for complete search history.

(56) References Cited

U.S. PATENT DOCUMENTS

| | | |
|---|---|---|
| 7,037,908 B2 | 5/2006 | Naidu et al. |
| 7,115,601 B2 | 10/2006 | Naidu et al. |
| 7,135,467 B2 | 11/2006 | Walker et al. |
| 7,157,447 B2 | 1/2007 | Naidu et al. |
| 7,169,780 B2 | 1/2007 | Crescenzi et al. |

(Continued)

FOREIGN PATENT DOCUMENTS

| | | |
|---|---|---|
| WO | 2006103399 A1 | 10/2006 |
| WO | 2006116764 A1 | 11/2006 |
| WO | 2011045330 A1 | 4/2011 |
| WO | WO2011105590 A1 | 9/2011 |
| WO | 2011121105 A1 | 10/2011 |
| WO | 2011129095 A1 | 10/2011 |
| WO | WO2007049675 A1 | 10/2011 |

OTHER PUBLICATIONS

Banker et al. (1997).*
Extended European Search Report for 13864799.5, mailed May 3, 2016, 7 pages.
Kawasuji, T.; et al., Carbamoyl Pyridone HIV-1 Integrase Inhibitors. 2. Bi- and Tricyclic Derivatives Result in Superior Antiviral and Pharmacokinetic Profiles, Journal of Medicinal Chemistry, 2013, pp. 1124-1135., vol. 56, No. 3.

(Continued)

*Primary Examiner* — Paul V Ward
(74) *Attorney, Agent, or Firm* — Nicole M. Beeler; Catherine D. Fitch

(57) ABSTRACT

The present invention relates to 4-Pyridinonetriazine Derivatives of Formula (I); and pharmaceutically acceptable salts thereof, wherein A, X, Y, $R^1$, $R^2$, $R^3$ and $R^5$ are as defined herein. The present invention also relates to compositions comprising at least one 4-Pyridinonetriazine Derivative, and methods of using the 4-Pyridinonetriazine Derivatives for treating or preventing HIV infection in a subject.

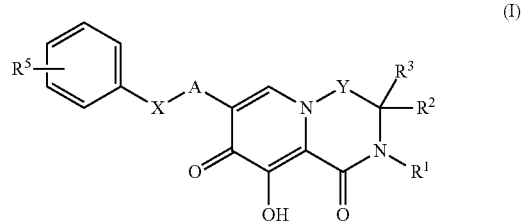

(I)

19 Claims, No Drawings

(56) References Cited

U.S. PATENT DOCUMENTS

| | | |
|---|---|---|
| 7,173,022 B2 | 2/2007 | Naidu et al. |
| 7,176,196 B2 | 2/2007 | Naidu et al. |
| 7,192,948 B2 | 3/2007 | Banville et al. |
| 7,211,572 B2 | 5/2007 | Miyazaki e |
| 7,217,713 B2 | 5/2007 | Crescenzi et al. |
| 7,232,819 B2 | 6/2007 | Di Francesco et al. |
| 7,273,859 B2 | 9/2007 | Naidu |
| 7,279,487 B2 | 10/2007 | Egbertson et al. |
| 7,414,045 B2 | 8/2008 | Crescenzi et al. |
| 7,419,969 B2 | 9/2008 | Naidu et al. |
| 2004/0229909 A1 | 11/2004 | Kiyama et al. |
| 2005/0054645 A1 | 3/2005 | Miyazaki et al. |
| 2006/0276466 A1 | 12/2006 | Naidu et al. |
| 2007/0049606 A1 | 3/2007 | Banville et al. |
| 2007/0083045 A1 | 4/2007 | Di Francesco et al. |
| 2007/0111984 A1 | 5/2007 | Naidu et al. |
| 2007/0111985 A1 | 5/2007 | Naidu et al. |
| 2007/0112190 A1 | 5/2007 | Naidu |
| 2007/0123524 A1 | 5/2007 | Crescenzi et al. |
| 2007/0142635 A1 | 6/2007 | Askin et al. |
| 2007/0149556 A1 | 6/2007 | Mikamiyama et al. |
| 2007/0281917 A1 | 12/2007 | Naidu et al. |
| 2008/0004265 A1 | 1/2008 | Walker et al. |
| 2009/0143356 A1 | 6/2009 | Yoshida et al. |
| 2012/0108564 A1 | 5/2012 | Miyazaki et al. |
| 2012/0208998 A1 | 8/2012 | Yoshida et al. |
| 2013/0096109 A1 | 4/2013 | Hattori et al. |

OTHER PUBLICATIONS

Berge et al., Pharmaceutical Salts, J. Pharm Sci., 1977, pp. 1-19, 66.

Bingham et al., Over one hundred solvates of sulfathiazole, Chem. Commun., 2001, 603-604.

Caira et al, Preparation and Crystal Characterization of a Polymorph, a Monohydrate, and an Ethyl Acetate Solvate of the Antifungal Fluconazole, J. Pharmaceutical Sci, 2004, 601-611, 93(3).

Elsa C. Van Tonder, et al, Preparation and Physicochemical Characterization of 5 Niclosamide Solvates and 1 Hemisolvate, AAPS Pharmscitech, 2004, pp. 1-10, 5(1), US.

Ester Muraglia, et al, Design and Synthesis of Bicyclic Pyrimidinones as Potent and Orally Bioavailable HIV-1 Integrase Inhibits, J. Med. Chem., 2008, pp. 861-874, vol. 51, US.

Gould, Salt selection for basic drugs, International J. of Pharmaceutics, 1986, 201-217, 33.

Hiroyuki Toh, et al, Close Structural Resemblance Between Putative Polymerase of a *Drosophila* Transposable Genetic Element 17.5 and Pol Gene Product of Moloney Murine Leukaemia Virus, The EMBO Journal, 1985, pp. 1267-1272, vol. 4, No. 5, US.

Laurence H. Pearl, et al, A Structural Model for the Retroviral Proteases, Nature, 1987, pp. 351-354, vol. 329, US.

Lee Ratner, et al, Complete Nucleotide Sequence of AIDS Virus, HTLV-III, Nature, 1985, pp. 277-284, vol. 313, US.

Marco Ferrara, et al, Synthesis of a Hexahydropyrimido[1,2-a]Azepine-2-Carboxamide Derivative Useful as an HIV Integrase Inhibitor, Tetrahedron Letters, Jul. 2007, pp. 8379-8382, vol. 48, No. 37, US.

Michael D. Power, et al, Nucleotide Sequence of SRV-1, a Type D Simian, Science, 1986, pp. -1572, vol. 231, US.

Olaf D. Kinzel, et al, The Syntheis of Tetrahydropyridopyrimidones as a New Scaffold for HIV-1 Integrase Inhibitors, Tetrahedron Letters, 2007, pp. 6552-6555, vol. 48, No. 37, US.

T. Higuchi and V. Stella, Pro-drugs as NovelDelivery Systems (1987) 14 of the A.C.S. Symposium Series.

\* cited by examiner

4-PYRIDINONETRIAZINE DERIVATIVES AS HIV INTEGRASE INHIBITORS

CROSS-REFERENCE TO RELATED APPLICATIONS

This application is the national stage application under 35 U.S.C. 371 of International Patent Application No. PCT/US2013/074590, filed Dec. 12, 2013, which claims priority to U.S. Provisional Patent Application No. 61/738,112, filed Dec. 17, 2012. Each of the aforementioned provisional and PCT applications is incorporated by reference in its entirety.

FIELD OF THE INVENTION

The present invention relates to 4-Pyridinonetriazine Derivatives, compositions comprising at least one 4-Pyridinonetriazine Derivative, and methods of using the 4-Pyridinonetriazine Derivatives for treating or preventing HIV infection in a subject.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication.

The following references are of interest as background:

International Publication Nos. WO 11/045330 and WO 11/121105 disclose macrocyclic compounds having HIV integrase inhibitory activity.

Kinzel et al., *Tet. Letters* 2007, 48(37): pp. 6552-6555 discloses the synthesis of tetrahydropyridopyrimidones as a scaffold for HIV-1 integrase inhibitors.

Ferrara et al., *Tet. Letters* 2007, 48(37), pp. 8379-8382 discloses the synthesis of a hexahydropyrimido[1,2-a]azepine-2-carboxamide derivative useful as an HIV integrase inhibitor.

Muraglia et al., *J. Med. Chem.* 2008, 51: 861-874 discloses the design and synthesis of bicyclic pyrimidinones as potent and orally bioavailable HIV-1 integrase inhibitors.

US2004/229909 discloses certain compounds having integrase inhibitory activity.

U.S. Pat. No. 7,232,819 and US 2007/0083045 disclose certain 5,6-dihydroxypyrimidine-4-carboxamides as HIV integrase inhibitors.

U.S. Pat. Nos. 7,169,780, 7,217,713, and US 2007/0123524 disclose certain N-substituted 5-hydroxy-6-oxo-1,6-dihydropyrimidine-4-carboxamides as HIV integrase inhibitors.

U.S. Pat. No. 7,279,487 discloses certain hydroxynaphthyridinone carboxamides that are useful as HIV integrase inhibitors.

U.S. Pat. Nos. 7,135,467 and 7,037,908 disclose certain pyrimidine carboxamides that are useful as HIV integrase inhibitors.

U.S. Pat. No. 7,211,572 discloses certain nitrogenous condensed ring compounds that are HIV integrase inhibitors.

U.S. Pat. No. 7,414,045 discloses certain tetrahydro-4H-pyrido[1,2-a]pyrimidine carboxamides, hexahydropyrimido[1,2-a]azepine carboxamides, and related compounds that are useful as HIV integrase inhibitors.

WO 2006/103399 discloses certain tetrahydro-4H-pyrimidooxazepine carboaxmides, tetrahydropyrazinopyrimidine carboxamides, hexahydropyrimidodiazepine carboxamides, and related compounds that are useful as HIV integrase inhibitors.

US 2007/0142635 discloses processes for preparing hexahydropyrimido[1,2-a]azepine-2-carboxylates and related compounds.

US 2007/0149556 discloses certain hydroxypyrimidinone derivatives having HIV integrase inhibitory activity.

Various pyrimidinone compounds useful as HIV integrase inhibitors are also disclosed in U.S. Pat. Nos. 7,115,601, 7,157,447, 7,173,022, 7,176,196, 7,192,948, 7,273,859, and 7,419,969.

US 2007/0111984 discloses a series of bicyclic pyrimidinone compounds useful as HIV integrase inhibitors.

US 2006/0276466, US 2007/0049606, US 2007/0111985, US 2007/0112190, US 2007/0281917, US 2008/0004265 each disclose a series of bicyclic pyrimidinone compounds useful as HIV integrase inhibitors.

SUMMARY OF THE INVENTION

In one aspect, the present invention provides Compounds of Formula (I):

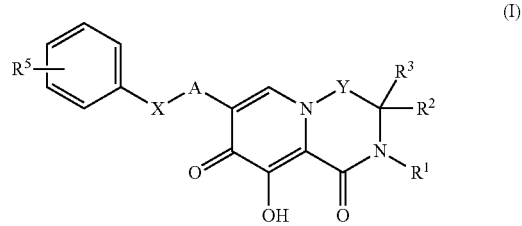

or a pharmaceutically acceptable salt or prodrug thereof, wherein:

A is —NHC(O)— or 5 or 6-membered monocyclic heteroaryl;

X is $C_1$-$C_3$ alkylene;

Y is O, —C($R^8$)$_2$— or —N($R^4$)—;

$R^1$ is $C_1$-$C_6$ alkyl, $C_3$-$C_7$ cycloalkyl or —($C_1$-$C_4$ alkylene)-O—($C_1$-$C_6$ alkyl);

$R^2$ is selected from H, $C_1$-$C_6$ alkyl, $C_1$-$C_6$ hydroxyalkyl, —($C_1$-$C_6$ alkylene)$_p$-C(O)OR$^6$, —($C_1$-$C_6$ alkylene)$_p$-C(O)R$^6$, —($C_1$-$C_6$ alkylene)$_p$-C(O)N(R$^9$)$_2$, $C_3$-$C_7$ cycloalkyl, 5 or 6-membered monocyclic heterocycloalkyl, 5 or 6-membered monocyclic heteroaryl and —($C_1$-$C_4$ alkylene)-O—($C_1$-$C_6$ alkyl), wherein said $C_3$-$C_7$ cycloalkyl group, said 5 or 6-membered monocyclic heteroaryl group and said 5 or 6-membered monocyclic heterocycloalkyl group can be optionally substituted with $R^7$;

$R^3$ is selected from H, $C_1$-$C_6$ alkyl, $C_3$-$C_7$ cycloalkyl, 5 or 6-membered monocyclic heterocycloalkyl and —($C_1$-$C_4$ alkylene)-O—($C_1$-$C_6$ alkyl), wherein said $C_3$-$C_7$ cycloalkyl group and said 5 or 6-membered monocyclic heterocycloalkyl group can be optionally substituted with one or more groups selected from $R^7$, or $R^2$ and $R^3$, together with the common carbon atom to which they are both attached, can optionally join to form a spirocyclic $C_3$-$C_7$ cycloalkyl group or a spirocyclic $C_3$-$C_7$ cycloalkenyl group, wherein said spirocyclic $C_3$-$C_7$ cycloalkyl group and said spirocyclic $C_3$-$C_7$ cycloalkenyl group can be optionally substituted with one or more groups selected from $R^7$, and wherein said spirocyclic $C_3$-$C_7$ cycloalkyl group can be fused to another ring, selected from $C_3$-$C_7$ cycloalkyl, 3 to 8-membered monocyclic heterocycloalkyl and 5 or 6-membered monocyclic heteroaryl, and wherein said spirocyclic $C_3$-$C_7$ cycloalkyl group can form a spirocyclic ring system with a $C_3$-$C_7$ cycloalkyl group or a 3 to 8-membered monocyclic heterocycloalkyl group, or $R^1$ and $R^3$, together with the carbon atoms to which they are attached, can optionally join to form a 3 to 8-membered monocyclic heterocycloalkyl group, which can be optionally substituted with one or more groups selected from $R^7$;

$R^4$ is selected from H, $C_1$-$C_6$ alkyl, —SO$_2$R$^6$, —C(O)R$^6$, —($C_1$-$C_6$ alkylene)$_p$-C(O)N(R$^9$)$_2$, and —($C_2$-$C_4$ alkylene)-O—($C_1$-$C_6$ alkyl);

$R^5$ represents up to 3 optional substitutents, each independently selected from halo, $C_1$-$C_6$ alkyl, —O—($C_1$-$C_6$ alkyl) and $C_1$-$C_6$ haloalkyl; and each occurrence of $R^6$ is independently selected from $C_1$-$C_6$ alkyl, $C_1$-$C_6$ haloalkyl, $C_3$-$C_7$ cycloalkyl, phenyl, 3 to 8-membered monocyclic heterocycloalkyl or 6-membered monocyclic heteroaryl and 8 to 10-membered bicyclic heteroaryl, wherein said $C_3$-$C_7$ cycloalkyl group, said phenyl group, said 5 or 6-membered monocyclic heteroaryl group and said 8 to 10-membered bicyclic heteroaryl group can be optionally substituted with $R^7$;

each occurrence of $R^7$ is independently selected from halo, $C_1$-$C_6$ alkyl, $C_1$-$C_6$ haloalkyl, 3 to 8-membered monocyclic heterocycloalkyl, 6 to 10-membered bicyclic heterocycloalkyl, —O—($C_1$-$C_6$ alkyl), —O—($C_6$-$C_{10}$ aryl), —O—($C_1$-$C_6$ alkylene)-O—($C_1$-$C_6$ alkyl), —O—($C_1$-$C_6$ haloalkyl), —O—($C_1$-$C_6$ alkylene)-O—($C_1$-$C_6$ alkylene)-O—($C_1$-$C_6$ alkyl), —NH$_2$, —NH($C_1$-$C_6$ alkyl), —N($C_1$-$C_6$ alkyl)$_2$, —S(O)$_2$—($C_1$-$C_6$ alkyl), —NHS(O)$_2$—($C_1$-$C_6$ alkyl), —OC(O)—($C_1$-$C_6$ haloalkyl), —($C_1$-$C_6$ alkylene)$_p$-C(O)OR$^6$, —($C_1$-$C_6$ alkylene)$_p$-C(O)R$^6$, —($C_1$-$C_6$ alkylene)$_p$-C(O)N(R$^9$)$_2$, $C_1$-$C_6$ hydroxyalkyl, —P(O)(OR$^{11}$)$_2$, and —CN;

each occurrence of $R^8$ is independently selected from H, $C_1$-$C_6$ alkyl, $C_3$-$C_7$ cycloalkyl, 3 to 8-membered monocyclic heterocycloalkyl and 5 or 6-membered monocyclic heteroaryl;

each occurrence of $R^9$ is independently selected from H, $C_1$-$C_6$ alkyl, $C_3$-$C_7$ cycloalkyl, —($C_1$-$C_6$ alkylene)-N(R$^9$)$_2$, $C_1$-$C_6$ haloalkyl, —C(O)O($C_1$-$C_6$ alkyl), —($C_1$-$C_6$ alkylene)$_p$-R$^{10}$ and —($C_1$-$C_6$ alkylene)-O—($C_1$-$C_6$ alkyl);

each occurrence of $R^{10}$ is independently selected from H, $C_1$-$C_6$ alkyl, $C_3$-$C_7$ cycloalkyl, 5 or 6-membered monocyclic heteroaryl and 3 to 8-membered monocyclic heterocycloalkyl;

each occurrence of $R^{11}$ is independently selected from H and $C_1$-$C_6$ alkyl;

n is an integer ranging from 0 to 3; and each occurrence of p is independently 0 or 1.

The Compounds of Formula (I) (also referred to herein as the "4-Pyridinonetriazine Derivatives") and pharmaceutically acceptable salts thereof can be useful, for example, for inhibiting HIV viral replication or replicon activity, and for treating or preventing HIV infection in a subject. Without being bound by any specific theory, it is believed that the 4-Pyridinonetriazine Derivatives inhibit HIV viral replication by inhibiting HIV Integrase.

Accordingly, the present invention provides methods for treating or preventing HIV infection in a subject, comprising administering to the subject an effective amount of at least one 4-Pyridinonetriazine Derivative.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention includes to 4-Pyridinonetriazine Derivatives, compositions comprising at least one 4-Pyridinonetriazine Derivative, and methods of using the 4-Pyridinonetriazine Derivatives for treating or preventing HIV infection in a subject.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . .

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of 4-Pyridinonetriazine Derivative and/or an additional therapeutic agent, or a composition thereof that is effective in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —CH($CH_3$)$CH_2CH_2$—, —CH($CH_3$)— and —$CH_2$CH($CH_3$)$CH_2$—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —$CH_2$—. The term "$C_1$-$C_4$ alkylene" refers to an alkylene group having from 1 to 4 carbon atoms. The term "$C_2$-$C_4$ alkylene" refers to an alkylene group having from 2 to 4 carbon atoms.

The term "alkenylene," as used herein, refers to an alkenyl group, as defined above, wherein one of the alkenyl group's hydrogen atoms has been replaced with a bond. Non-limiting examples of alkenylene groups include —CH=CH—, —CH=CHCH$_2$—, —CH$_2$CH=CH—, —CH$_2$CH=CHCH$_2$—, —CH=CHCH$_2$CH$_2$—, —CH$_2$CH$_2$CH=CH— and —CH(CH$_3$)CH=CH—. In one embodiment, an alkenylene group has from 2 to about 6 carbon atoms. In another embodiment, an alkenylene group has from about 3 to about 5 carbon atoms. In another embodiment, an alkenylene group is branched. In another embodiment, an alkenylene group is linear. The term "$C_2$-$C_6$ alkylene" refers to an alkenylene group having from 2 to 6 carbon atoms. The term "$C_3$-$C_5$ alkenylene" refers to an alkenylene group having from 3 to 5 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

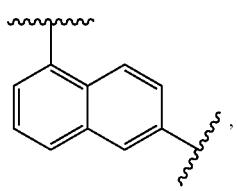 [SMILES: *c1ccc2c(*)cccc2c1]

is understood to represent both:

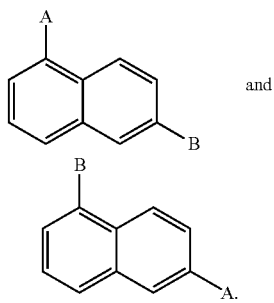

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

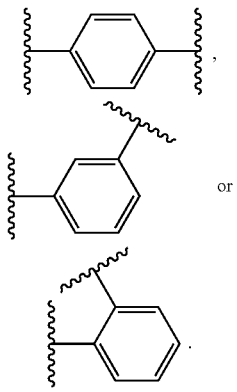

Unless otherwise indicated, an arylene group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to cyclobutanoyl:

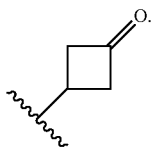 [SMILES: *C1CC(=O)C1]

The term "cycloalkenyl," as used herein, refers to a cycloalkyl group, as defined above, wherein said cycloalkyl group is non-aromatic and has at least one endocyclic double bond. In one embodiment, a cycloalkenyl contains from about 5 to about 10 ring carbon atoms. In another embodiment, a cycloalkyl contains from about 3 to about 7 ring atoms. In another embodiment, a cycloalkenyl contains from about 5 to about 6 ring atoms. The term "cycloalkenyl" also encompasses a cycloalkenyl group, as defined above, which is fused to an aryl (e.g., benzene) or heteroaryl ring. Non-limiting examples of monocyclic cycloalkenyls include cyclopropenyl, cyclobutenyl, cyclopentenyl, cyclohexenyl, cycloheptenyl and cyclooctenyl. A cycloalkenyl group can be optionally substituted with one or more "ring system substituents" which may be the same or different, and are as defined herein below. In one embodiment, a cycloalkenyl group is unsubstituted. The term "3 to 7-membered cycloalkenyl" refers to a cycloalkenyl group having from 3 to 7 ring carbon atoms. Unless otherwise indicated, a cycloalkenyl group is unsubstituted. A ring carbon atom of a cycloalkenyl group may be functionalized as a carbonyl group.

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered monocyclic heteroaryl. In another embodiment, a heteroaryl group comprises a 5- to 6-membered monocyclic heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

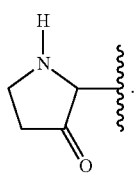

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic heterocycloalkyl" refers to a monocyclic heterocycloalkyl group having from 3 to 6 ring atoms. The term "4 to 7-membered monocyclic heterocycloalkyl" refers to a monocyclic heterocycloalkyl group having from 4 to 7 ring atoms. The term "7 to 11-membered bicyclic heterocycloalkyl" refers to a bicyclic heterocycloalkyl group having from 7 to 11 ring atoms. Unless otherwise indicated, a heterocycloalkyl group is unsubstituted.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

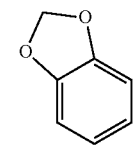

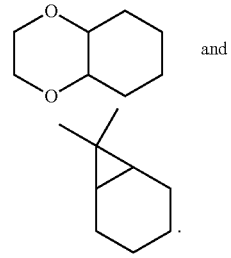

The term "substituted" means that one or more hydrogens on the designated atom is replaced with a selection from the indicated group, provided that the designated atom's normal valency under the existing circumstances is not exceeded, and that the substitution results in a stable compound.

Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, $R^1$, $R^7$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a 4-Pyridinonetriazine Derivative or a pharmaceutically acceptable salt of the compound. The transformation may occur by various mechanisms (e.g., by metabolic or chemical processes), such as, for example, through hydrolysis in blood. For example, if a 4-Pyridinonetriazine Derivative or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl, and the like.

Similarly, if a 4-Pyridinonetriazine Derivative contains an alcohol functional group, a prodrug can be formed by the replacement of one or more of the hydrogen atoms of the alcohol groups with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkyl, α-amino $(C_1-C_4)$alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a 4-Pyridinonetriazine Derivative incorporates an amine functional group, a prodrug can be formed by the replacement of a hydrogen atom in the amine group with a group such as, for example, R-carbonyl-, RO-carbonyl-, NRR'-carbonyl- wherein R and R' are each independently $(C_1-C_{10})$alkyl, $(C_3-C_7)$ cycloalkyl, benzyl, a natural α-aminoacyl, —C(OH)C(O)OY$^1$ wherein Y$^1$ is H, $(C_1-C_6)$ alkyl or benzyl, —C(OY$^2$)Y$^3$ wherein Y$^2$ is $(C_1-C_4)$ alkyl and Y$^3$ is $(C_1-C_6)$alkyl; carboxy$(C_1-C_6)$alkyl; amino$(C_1-C_4)$ alkyl or mono-N— or di-N,N—$(C_1-C_6)$alkylaminoalkyl; —C(Y$^4$)Y$^5$ wherein Y$^4$ is H or methyl and Y$^5$ is mono-N— or di-N,N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$ alkyl, —O—$(C_{1-4})$alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The 4-Pyridinonetriazine Derivatives can form salts which are also within the scope of this invention. Reference to a 4-Pyridinonetriazine Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a 4-Pyridinonetriazine Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a 4-Pyridinonetriazine Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J of Pharmeutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the 4-Pyridinonetriazine Derivatives may be atropisomers (e.g., substituted biaryls) and are considered as part of this invention. Enantiomers can also be directly separated using chiral chromatographic techniques.

It is also possible that the 4-Pyridinonetriazine Derivatives may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a 4-Pyridinonetriazine Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

The 4-Pyridinonetriazine Derivatives are useful in human and veterinary medicine for treating or preventing HIV infection in a subject. In one embodiment, the 4-Pyridinonetriazine Derivatives can be inhibitors of HIV viral replication. In a specific embodiment, the 4-Pyridinonetriazine Derivatives are inhibitors of HIV-1. Accordingly, the 4-Pyridinonetriazine Derivatives are useful for treating HIV infections and AIDS. In accordance with the invention, the 4-Pyridinonetriazine Derivatives can be administered to a subject in need of treatment or prevention of HIV infection.

Accordingly, in one embodiment, the invention provides methods for treating HIV infection in a subject comprising administering to the subject an effective amount of at least one 4-Pyridinonetriazine Derivative or a pharmaceutically acceptable salt thereof. In a specific embodiment, the present invention provides methods for treating AIDS in a subject comprising administering to the subject an effective amount of at least one 4-Pyridinonetriazine Derivative or a pharmaceutically acceptable salt thereof.

List of Abbreviations

Anal.=analytical
n-BuLi=n-butyl lithium
m-CPBA=3-chloroperoxybenzoic acid
DCM=dichloromethane
DEA=diethylamine
DIPEA=N,N-diisopropylethylamine
DMF=dimethylformamide
ESI=electrospray ionization
EtOAc=ethyl acetate
EtOH=ethanol
HPLC=high-pressure liquid chromatography
IPA=iso-propyl alcohol
IPAc=iso-propyl acetate
KF=Karl-Fischer titration (to determine water content)
KOt-Bu=potassium tert-butoxide
LCMS=liquid chromatography-mass spectrometry
LiHMDS=lithum hexamethyl silazane
MeCN=acetonitrile
MeOH'=methanol
MPa=milipascal
MS=mass spectroscopy
MTBE=methyl tert-butyl ether
NHS=normal human serum
NMR=nuclear magnetic resonance spectroscopy
Piv=pivalate, 2,2-dimethylpropanoyl
Pd/C=palladium on carbon
rt=room temperature
SFC=supercritical fluid chromatography
TFA=trifluoroacetic acid
TLC=thin-layer chromatography
p-TsOH=para-toluene sulfonic acid
THF=tetrahydrofuran The Compounds of Formula (I)

The present invention provides 4-Pyridinonetriazine Derivatives of Formula (I):

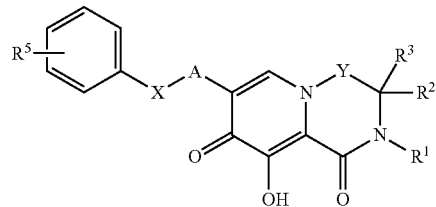

(I)

and pharmaceutically acceptable salts thereof, wherein A, X, Y, $R^1$, $R^2$, $R^3$ and $R^5$ are defined above for the Compounds of Formula (I).

In one embodiment, A is 5 or 6-membered monocyclic heterocycle.

In another embodiment, A is 5-membered monocyclic heterocycle.

In another embodiment, A is —NHC(O)—.

In still another embodiment, A is:

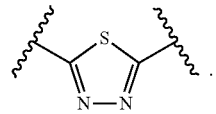 [SMILES: *c1nnc(*)s1]

In one embodiment, X is —$CH_2$—.
In another embodiment, X is —$CH(CH_3)$—.
In one embodiment, Y is O.
In another embodiment, Y is —$N(R^4)$—.
In another embodiment, Y is —$N(CH_3)$—.
In still another embodiment, Y is —$CHR^4$—.
In another embodiment, Y is —$C(R^4)_2$—.
In another embodiment, Y is —$CH_2$—.
In another embodiment, Y is —$CH(CH_3)$—.
In one embodiment, $R^1$ is $C_1$-$C_6$ alkyl.
In another embodiment, $R^1$ is $C_3$-$C_7$ cycloalkyl.
In another embodiment, $R^1$ is ethyl.
In still another embodiment, $R^1$ is —($C_1$-$C_4$ alkylene)-O—($C_1$-$C_6$ alkyl).
In another embodiment, $R^1$ is —$CH_2CH_2OCH_3$.
In one embodiment, $R^2$ is H.
In another embodiment, $R^2$ is $C_1$-$C_6$ alkyl.
In another embodiment, $R^2$ is $C_3$-$C_7$ cycloalkyl.
In another embodiment, $R^2$ is 5 or 6-membered monocyclic heterocycloalkyl.
In still another embodiment, $R^2$ is —($C_1$-$C_4$ alkylene)-O—($C_1$-$C_6$ alkyl).
In another embodiment, $R^2$ is methyl.
In one embodiment, $R^3$ is H.
In another embodiment, $R^3$ is $C_1$-$C_6$ alkyl.
In another embodiment, $R^3$ is $C_3$-$C_7$ cycloalkyl, which is optionally substituted with $R^7$.
In another embodiment, $R^3$ is 5 or 6-membered monocyclic heterocycloalkyl, which is optionally substituted with $R^7$.
In still another embodiment, $R^3$ is —($C_1$-$C_4$ alkylene)-O—($C_1$-$C_6$ alkyl).
In another embodiment, $R^3$ is selected from methyl, cyclopropyl, tetrahydropyranyl, imidazolyl and —$CH_2OCH_3$.
In one embodiment, $R^2$ is H and $R^3$ is selected from methyl, cyclopropyl, tetrahydropyranyl, imidazolyl and —$CH_2OCH_3$.

In one embodiment, $R^2$ and $R^3$, together with the common carbon atom to which they are both attached, join to form a spirocyclic $C_3$-$C_7$ cycloalkyl group, which is optionally substituted as set forth above for the compounds of formula (I).

In another embodiment, $R^2$ and $R^3$, together with the common carbon atom to which they are both attached, join to form a spirocyclic $C_3$-$C_7$ cycloalkyl group, selected from cyclobutyl, cyclopentyl or cyclohexyl, which is optionally substituted as set forth above for the compounds of formula (I).

In one embodiment, $R^1$ and $R^3$, together with the atoms to which they are attached, join to form a $C_3$-$C_7$ cycloalkyl group or a 3-8 membered heterocycloalkyl group, which is optionally substituted as set forth above for the compounds of formula (I).

In one embodiment, each occurrence of $R^5$ is halo.

In another embodiment, $R^5$ represents 2 fluoro groups.

In one embodiment, n is 1.

In one embodiment, the compounds of formula (I) have the formula (Ia):

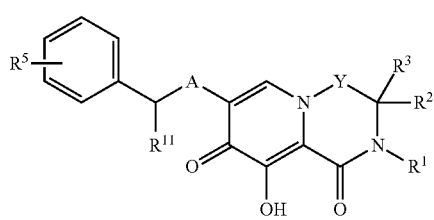

(Ia)

or a pharmaceutically acceptable salt or prodrug thereof, wherein:

A is —NHC(O)— or 5-membered heteroaryl;

Y is selected from O, —NHR$^4$, —CH$_2$— or —CH(CH$_3$)—;

$R^1$ is $C_1$-$C_6$ alkyl or —CH$_2$CH$_2$OCH$_3$;

$R^2$ is selected from H, $C_1$-$C_6$ alkyl, and —($C_1$-$C_4$ alkylene)-O—($C_1$-$C_6$ alkyl);

$R^3$ is selected from $C_1$-$C_6$ alkyl, $C_3$-$C_7$ cycloalkyl, 5 or 6-membered monocyclic heterocycloalkyl and —($C_1$-$C_4$ alkylene)-O—($C_1$-$C_6$ alkyl), or $R^2$ and $R^3$, together with the common carbon atom to which they are both attached, join to form a spirocyclic $C_3$-$C_7$ cycloalkyl group which can be optionally substituted as set forth in claim 1, or $R^1$ and $R^3$, together with the atoms o which they are attached, join to form a 3 to 8-membered heterocycloalkyl group, which can be optionally substituted as set forth above for the compounds of formula (I);

$R^4$ is selected from H, $C_1$-$C_6$ alkyl and —($C_2$-$C_4$ alkylene)-O—($C_1$-$C_6$ alkyl);

$R^5$ represents up to 2 optional substitutents, each independently selected from halo; and $R^{11}$ is H or methyl.

In one embodiment, the compounds of formula (I) have the formula (Ib):

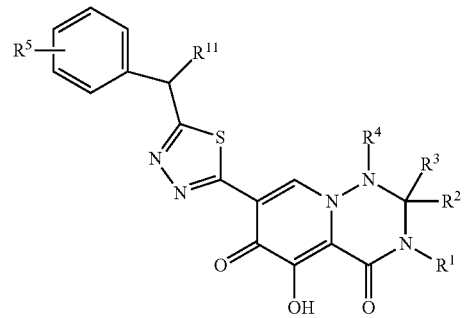

(Ib)

or a pharmaceutically acceptable salt or prodrug thereof, wherein:

$R^1$ is $C_1$-$C_6$ alkyl;

$R^2$ is selected from H, $C_1$-$C_6$ alkyl, and —($C_1$-$C_4$ alkylene)-O—($C_1$-$C_6$ alkyl);

$R^3$ is selected from $C_1$-$C_6$ alkyl, $C_3$-$C_7$ cycloalkyl, 5 or 6-membered monocyclic heterocycloalkyl and —($C_1$-$C_4$ alkylene)-O—($C_1$-$C_6$ alkyl), or $R^2$ and $R^3$, together with the common carbon atom to which they are both attached, join to form a spirocyclic $C_3$-$C_7$ cycloalkyl group which can be optionally substituted as set forth in claim 1;

$R^4$ is selected from H, $C_1$-$C_6$ alkyl and —($C_2$-$C_4$ alkylene)-O—($C_1$-$C_6$ alkyl);

$R^5$ represents up to 2 optional substitutents, each being fluoro; and $R^{11}$ is H or methyl.

In one embodiment, for the compounds of formula (I), (Ia) or (Ib), $R^1$ is H.

In one embodiment, for the compounds of formula (I), (Ia) or (Ib), $R^2$ is H, methyl or —CH$_2$CH$_2$OCH$_3$.

In another embodiment, for the compounds of formula (I), (Ia) or (Ib), $R^3$ is methyl, cyclopropyl, —CH$_2$CH$_2$OCH$_3$ or tetrahyrdopyranyl.

In one embodiment, for the compounds of formula (I), (Ia) or (Ib), $R^1$ and $R^3$, together with the atoms to which they are both attached, join to form a 3 to 8-membered monocyclic heterocycloalkyl group that is optionally substituted as set forth above for the Compounds of Formula (I).

In one embodiment, for the compounds of formula (I), (Ia) or (Ib), $R^2$ and $R^3$, together with the common carbon atom to which they are both attached, join to form a spirocyclic $C_3$-$C_7$ cycloalkyl group that is optionally substituted as set forth above for the Compounds of Formula (I).

In another embodiment, for the compounds of formula (I), (Ia) or (Ib), $R^2$ and $R^3$, together with the common carbon atom to which they are both attached, join to form a cyclopropyl, cyclobutyl or cyclopentyl group.

In still another embodiment, for the compounds of formula (I), (Ia) or (Ib), $R^4$ is methyl or —CH$_2$CH$_2$OCH$_3$.

In one embodiment, for the compounds of formula (I), (Ia) or (Ib), $R^5$ represents: (i) a single fluoro group in the para position or (ii) two fluoro groups, in the ortho and para positions.

In another embodiment, for the compounds of formula (I), (Ia) or (Ib), $R^5$ represents a single fluoro group in the para position.

In another embodiment, for the compounds of formula (I), (Ia) or (Ib), $R^5$ represents two fluoro groups, in the ortho and para positions.

In one embodiment, variables n, X, Y, $R^1$, $R^2$, $R^3$ and $R^5$ for the Compounds of Formula (I) are selected independently of each other.

In another embodiment, the Compounds of Formula (I) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HIV antiviral agents, immunomodulators, and anti-infective agents.

(c) The pharmaceutical composition of (b), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(d) A pharmaceutical combination that is (i) a Compound of Formula (I) and (ii) a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(e) The combination of (d), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(f) A method of inhibiting HIV replication in a subject in need thereof which comprises administering to the subject an effective amount of a Compound of Formula (I).

(g) A method of treating HIV infection and/or reducing the likelihood or severity of symptoms of HIV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine, (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (k) above are understood to include all embodiments of the compounds, including such embodiments as result from combinations of embodiments.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Non-limiting examples of the Compounds of Formula (I) include compounds 5-226 as set forth below, and pharmaceutically acceptable salts thereof.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Scheme 1 below. Alternative synthetic pathways and analogous structures will be apparent to those skilled in the art of organic synthesis.

Scheme 1 describes a method for making the compounds of formula (I), which correspond to the 4-pyridotriazines compounds of Formula (I).

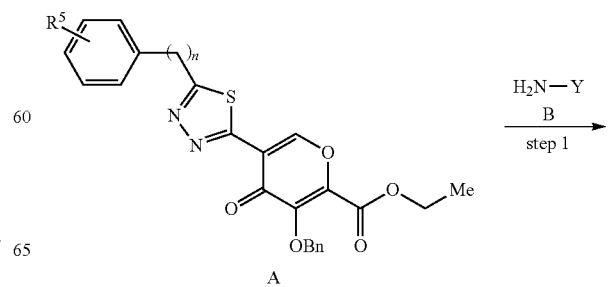

-continued

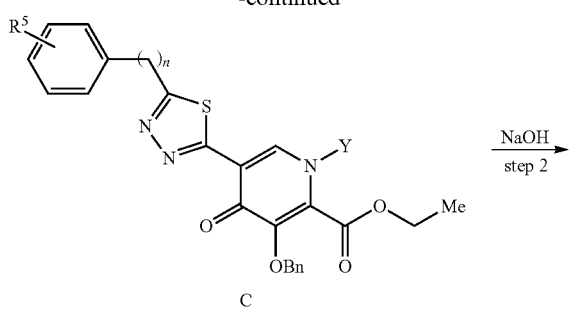

C

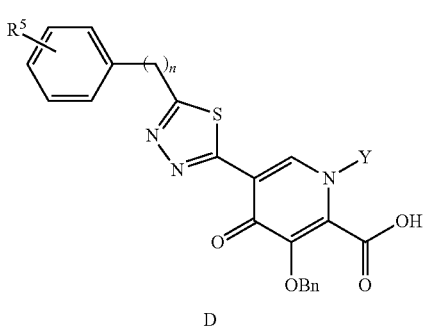

D

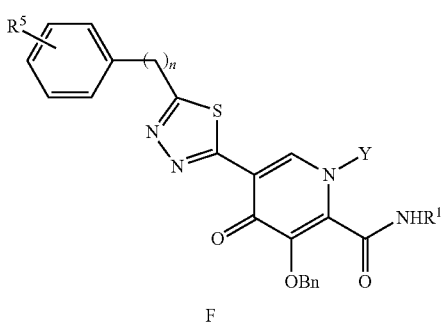

F

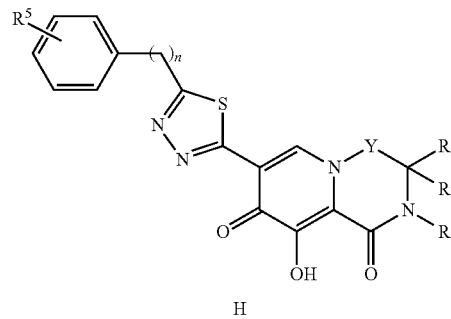

H

A pyranone compound of formula A is reacted with an amime of formula B to provide dihydropyridine compounds of formula C. Base promoted hydrolysis of the ester moiety of C to provide carboxylic acids of formula D, followed by amide coupling of D with an amine compound of formula E provides cyclization precursors of formula F. Acid catalyzed deprotection of the benzyl protecting group, followed by condensation with an aldehyde or ketone of formula G provides the product H.

Scheme 2

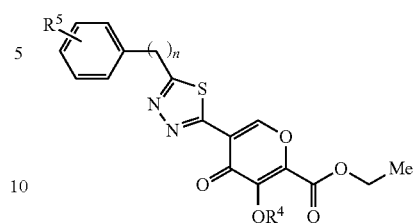 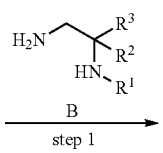

A

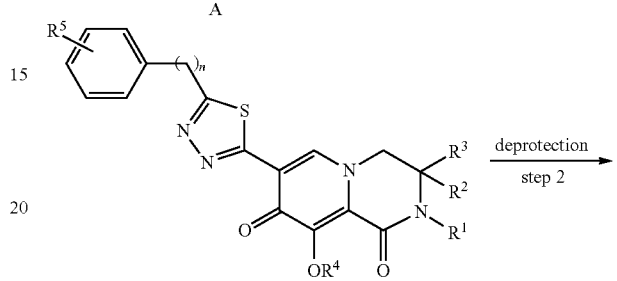

C

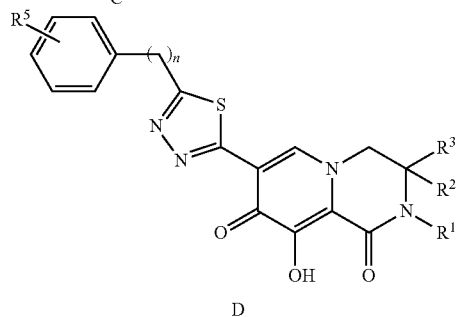

D

A pyranone compound of formula A is reacted with an amine of formula B to provide, either in a single step or in a multi-step fashion, dihydropyridine compounds of formula C. Deprotection of formula C will then provide compounds of the formula D.

Scheme 3

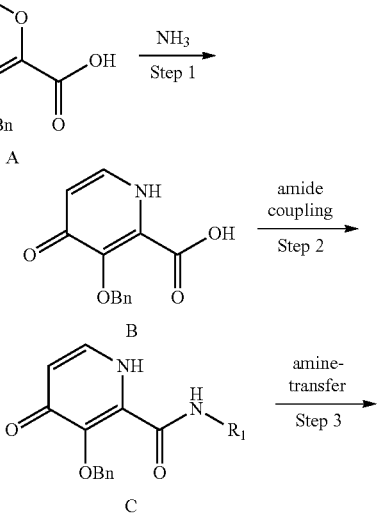

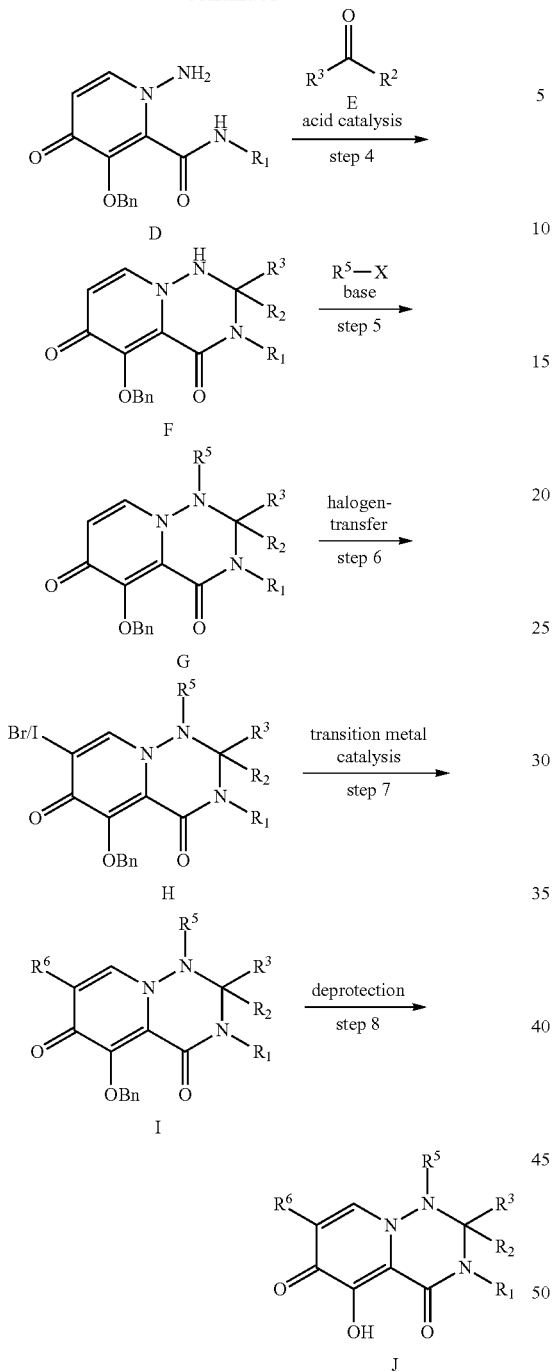

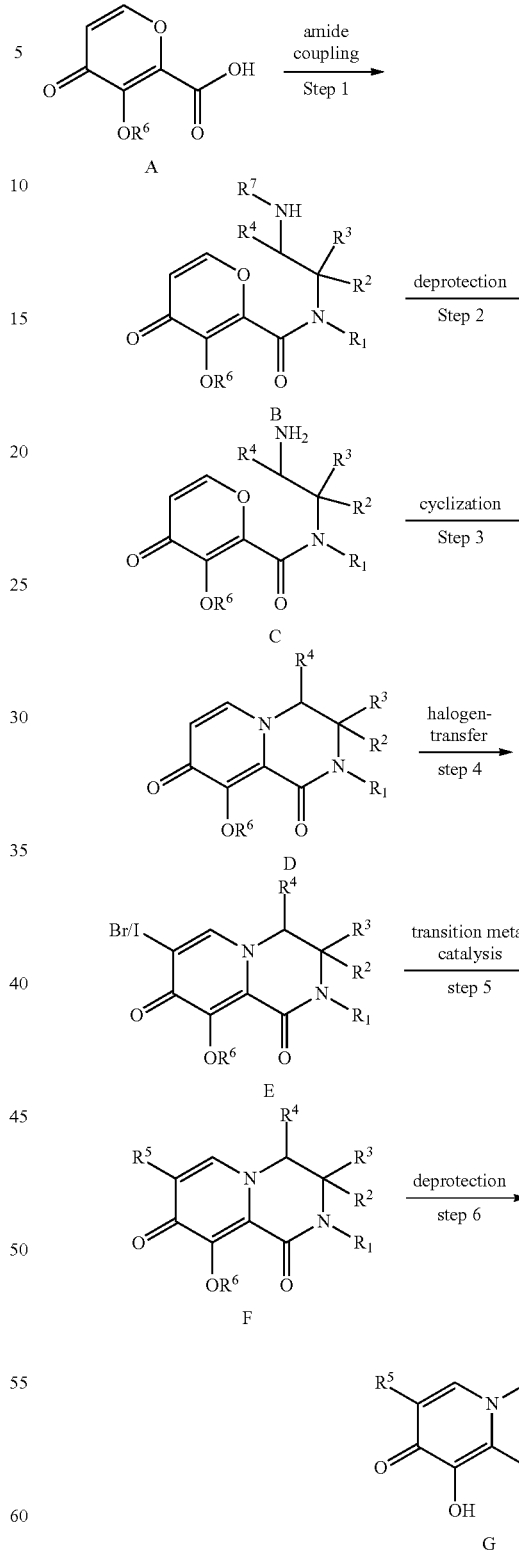

A pyranone compound of formula A is reacted with ammonia to provide a compound of formula B. Amide coupling with a suitably functionalized amine affords a compound of the formula C. Amine transfer will then afford a compound of the formula D. Acid-catalyzed condensation with a carbonyl compound of the formula E affords a compound of the formula F. Alkylation under basic conditions then affords a compound of the formula G. Halogen-transfer using a suitable reagent affords a compound of the formula H. Transition metal-catalyzed cross-coupling with a suitable reagent will afford a compound of the formula I. Finally, deprotection affords a compound of the formula J.

A pyranone compound of formula A is reacted with a suitably functionalized amine to provide a compound of formula B. Deprotection affords a compound of the general formula C. Cyclization then affords a compound of the formula D. Halogen-transfer using a suitable reagent affords a compound of the formula E. Transition metal-catalyzed cross-coupling with a suitable reagent will afford a compound of the formula F. Finally, deprotection affords a compound of the formula G.

EXAMPLES

General Methods

The compounds described herein can be prepared according to the procedures of the following schemes and examples, using appropriate materials and are further exemplified by the following specific examples. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted. Mass spectra (MS) were measured by electrospray ion-mass spectroscopy (ESI). $^1$H NMR spectra were recorded at 400-500 MHz. Compounds described herein were synthesized as a racemic mixture unless otherwise stated in the experimental procedures.

Example 1

Preparation of Intermediate Compound 1

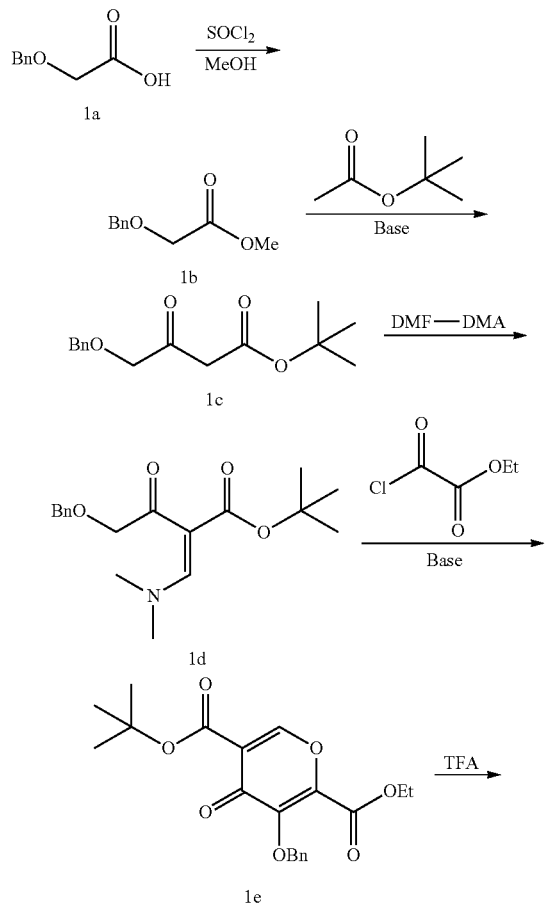

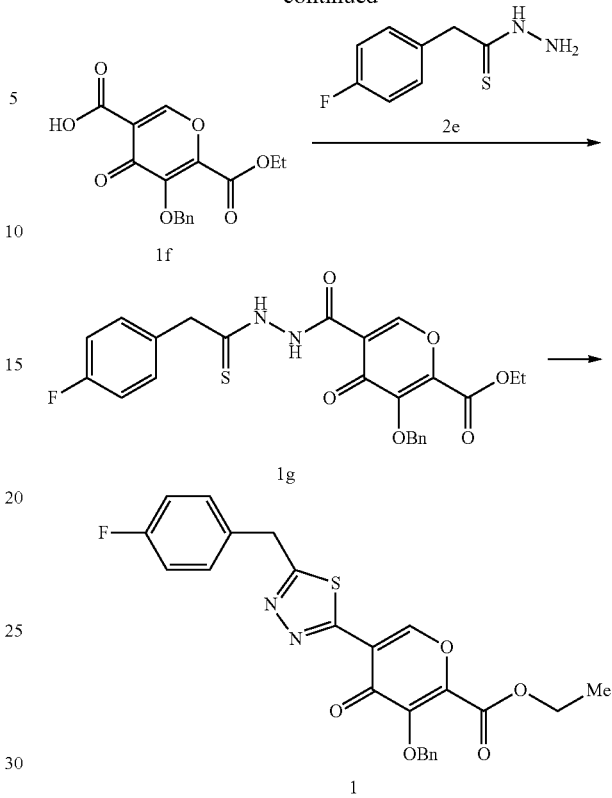

Step A—Synthesis of Intermediate Compound 1b

To a solution of compound 1a (200 g, 1.2 mol) in dry Methanol (2 L) was added SOCl$_2$ (424 g, 3.6 mol) under N$_2$ at 0° C., then heated under reflux for 6 hours. The reaction mixture was concentrated in vacuo and the resulting residue was dissolved in EtOAc (3 L). The organic phase was washed with NaHCO$_3$ (2 L×2), brine, dried over Na$_2$SO$_4$ and concentrated in vacuo to provide compound 1b (200 g) as an oil.

Step B—Synthesis of Intermediate Compound 1c

To a solution of compound 1b (322 g, 2.78 mol) in dry THF (2.8 L) was added LiHMDS (2.78 L, 2.78 mol) at −70° C. under N$_2$. After stirred at −70° C. for 1 hourour, then compound 2 (250 g, 1.39 mol) was added and the mixture was allowed to stir at −70° C. for 1.5 hours. The reaction was quenched with H$_2$O (2 L) and extracted with EtOAc (8 L×3). The combined organic phase was washed with brine, dried over Na$_2$SO$_4$, and concentrated in vacuo to provide compound 1c (190 g) as an oil.

Step C—Synthesis of Intermediate Compound 1d

A mixture of compound 1c (85 g, 0.32 mol) and DMF-DMA (76 g, 0.64 mol) in DMF (200 mL) was heated to 100° C. for 6 hours. The reaction was concentrated in vacuo and the resulting residue was purified using flash chromatography on silica gel (PE:EA=50:1 to 1:1) to provide compound 1d as solid.

Step D—Synthesis of Intermediate Compound 1e

To a solution of compound 1d (50 g, 0.16 mol) in THF (300 mL) was added LiHMDS (190 mL, 0.19 mmol) at −70° C. under N$_2$. After stirring at −70° C. for 0.5 h, ethyl 2-chloro-2-oxoacetate (25.8 g, 0.19 mol) was added and the mixture was allowed to stir at −70° C. for 1 hourour. TLC(PE:EA=1:1) showed the reaction was complete. The reaction was quenched with sat. aq. KHSO$_4$ (250 mL) and extracted with EtOAc (500 mL×3). The combined organic phase was washed with brine, dried over Na$_2$SO$_4$ and concentrated in vacuo to provide the crude product. The residue was diluted with toluene and concentrated in vacuo, then toluene (500 mL) and TEA (50 mL) were added and the mixture was allowed to stir at room temperature for 1 hourour. The mixture was concentrated in vacuo and the crude product was purified using flash chromatography on silica gel (PE:EA=1:0 to 40:1) to provide compound 1e as a solid.

Step E—Synthesis of Intermediate Compound 1f

To a stirring solution of the compound 1e (85 g, 0.23 mol) in EtOAc (100 mL) was added HCl/EtOAc (4 N, 920 mL) at 0° C. and the resulting mixture was allowed to stir at room temperature for 1 hourour. TLC (PE: EA=5:1) showed the reaction was complete. The reaction was concentrated in vacuo and to the resulting residue was added hexane (1 L). The mixture was allowed to stir for 1 hourour and filtered to provide compound 1f as a solid.

Steps F&G—Synthesis of Intermediate 1

To a stirring solution of the compound 1f (3.3 g, 10.3 mmol) in toluene (70 mL) was added oxalyl chloride (20.6 mL) and DMF (0.2 mL) at 0° C. under N$_2$ and the resulting mixture was allowed to stir at room temperature for 2 hours. The mixture was concentrated in vacuo and to the resulting residue was added CHCl$_3$ (100 mL) and compound 2e (2.84 g, 15.45 mmol). The resulting mixture was allowed to stir at room temperature overnight. TLC (Dichloromethane: Methanol=10:1) showed the starting material was consumed. To the reaction mixture was added HCl (4M, 10 mL in MTBE) the mixture was allowed to stir at room temperature for 2 h. To the mixture was added 5% aq. KHSO$_4$ (200 mL) and extracted with CHCl$_2$ twice. The organic layer was washed with brine, dried over Na$_2$SO$_4$ and concentrated in vacuo. The crude product was purified using silica gel column (PE:EA=50:1 to 1:1) to provide 1 as a solid. $^1$H NMR (CDCl3, 400 MHz) 9.07 (s, 1H), 7.45 (m, 2H), 7.35-7.25 (m, 5H), 7.03 (m, 2H).5.34 (s, 2H), 4.39-4.37 (q, 2H), 1.36-1.32 (t, 3H) LCMS (M+H)=467.1

Example 2

Preparation of Intermediate Compound 2

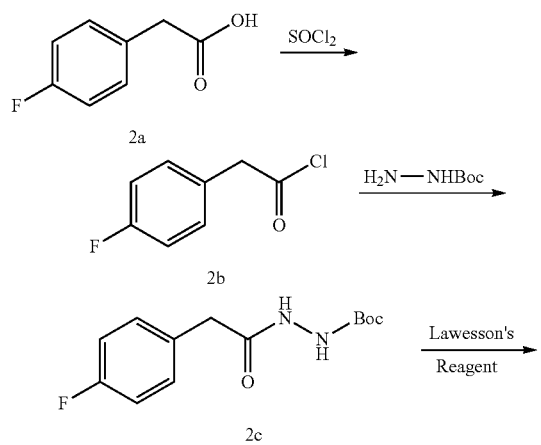

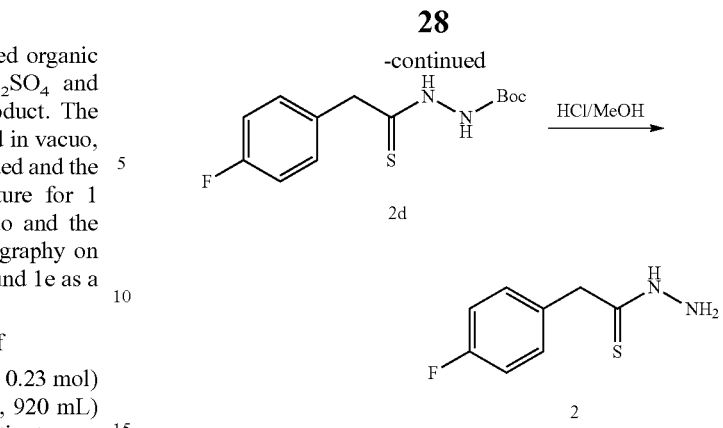

Step A—Synthesis of Intermediate Compound 2b

To a solution of compound 2a (100 g, 0.65 mol) in anhydrous DCM (1 L) was added SOCl$_2$ (200 mL) dropwise at 0° C. under a drying tube charged with CaCl$_2$. After the addition, the mixture was heated to reflux and stirred overnight. The reaction was done in 2 batches, which were combined and concentrated in vacuo to provide crude compound 2b as an oil.

Step B—Synthesis of Intermediate Compound 2c

To a solution of BocNHNH$_2$ (102.9 g, 0.78 mol) and TEA (135.4 mL, 0.97 mol) in anhydrous DCM (800 mL) was added a solution of compound 2b (138 g) in anhydrous DCM (500 mL) at 0° C. under drying tube charging with CaCl$_2$. The mixture was warmed up to room temperature and stirred for 2 hours. The mixture was quenched with H$_2$O (1 L). The reaction was done in two batches which were combined. The two phases were separated and the aqueous layer was extracted with DCM (1 L×2). The organic layer was washed with water (1 L×4), brine, dried over Na$_2$SO$_4$, concentrated in vacuo to provide compound 2c as a solid.

Step C—Synthesis of Intermediate Compound 2d

A mixture of compound 2c (50 g, 186.4 mmol) and Lawesson's reagent (75.4 g, 186.4 mmol) in THF (600 mL) was allowed to stir at 60° C. overnight. The mixture was poured into 10% Na$_2$CO$_3$ (1000 mL) and stirred at room temperature for 1 hourour. The reaction was done in two batches which were combined, and the mixture was extracted with EtOAc (1 L×3). The organic layer was washed with brine, dried over Na$_2$SO$_4$, concentrated in vacuo to provide compound 2d as a solid.

Step D—Synthesis of Intermediate 2

The suspension of compound 2d (240 g, 186.4 mmol, crude) in HCl/Methanol (1.2 L, 4N) was allowed to stir at room temperature for 1 hourour. The mixture was filtered and the filtrate was concentrated in vacuo to provide the HCl salt of compound 2, which was dissolved into water. The aqueous layer was basified with 10% Na$_2$CO$_3$ until pH=8 and extracted with EtOAc (1 L×4). The organic layer was washed with brine, dried over Na$_2$SO$_4$, concentrated in vacuo to provide compound 2 as a solid. $^1$H NMR (CDCl$_3$, 400 MHz) 8.44 (br, 1H), 7.26-7.21 (m, 2H), 7.07-7.02 (m, 2H), 4.83 (br, 2H), 4.05 (s, 2H) LCMS (M+H)=185.0

The compound set forth in the table below was prepared using the method described above in Example 1 and substituting the appropriate reactants and reagents:

| Compound | Structure | Exact Mass [M + H]+ |
|---|---|---|
| 1-2 | 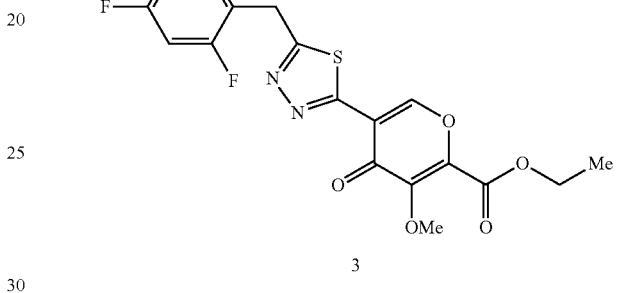 | 485 |

Example 3

Preparation of Intermediate Compound 3

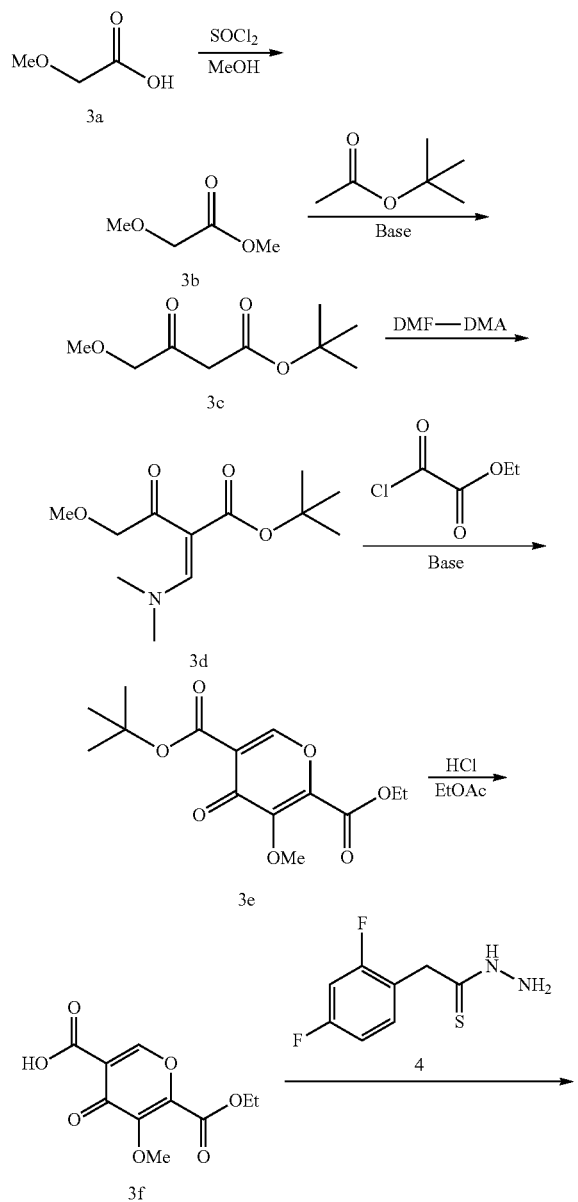

Step A—Synthesis of Intermediate Compound 3b

To the solution of compound 3a (200 g, 2.2 mol) in dry methanol (2 L) was added SOCl$_2$ (778 g, 6.6 mol) under N$_2$ at 0° C., then heated to reflux and allowed to stir at this temperature for 6 hours. The reaction mixture was concentrated in vacuo, the resulting residue was dissolved in EtOAc (3 L) and washed with NaHCO$_3$ (2 L×2), the organic phase was washed with brine, dried over anhydrous Na$_2$SO$_4$ and concentrated in vacuo to provide compound 3b as an oil that was used without further purification.

Step B—Synthesis of Intermediate Compound 3c

A 10 L three-necked round bottom flask equipped with a mechanic stirrer and thermometer was charged with a solution of tert-butyl acetate (1612, 13.9 mol) in dry THF (14 L) and cooled to −70° C. under N$_2$. A solution of LiHMDS (13.9 L, 13.9 mol) in THF was added at −70° C. and the mixture was allowed to stir at −70° C. for 1 hour. A solution of 3b (723 g, 6.95 mol) in THF (1 L) was added to the reaction and stirred at −70° C. for 0.5 hours. The reaction was quenched by the addition of water (10 L) and the mixture was extracted with EtOAc. The combined the organic phase was washed with brine, dried over Na$_2$SO$_4$ and concentrated in vacuo to provide 3c as oil. $^1$H NMR (400 MHz, CDCl$_3$) δ 4.09 (s, 2H), 3.43 (s, 2H), 3.42 (s, 2H), 1.47 (s, 9H).

Step C—Synthesis of Intermediate Compound 3d

A mixture of 3c (564 g, 3 mol) and DMF-DMA (696 g, 6 mol) in toluene (1380 L) was heated to 80° C. for 2 hours. The reaction was concentrated to provide 3d as solid that was used without further purification. $^1$H NMR (400 MHz, CDCl$_3$) δ 7.65 (s, 1H), 4.35 (s, 2H), 3.40 (s, 2H), 3.36-2.87 (m, 6H), 1.48 (s, 9H).

Step D—Synthesis of Intermediate Compound 3e

A solution of 3d (600 g, 2469 mmol) in dry THF (3600 mL) was cooled to −70° C. under N$_2$, and treated dropwise over 0.5 hours with a solution of LiHMDS (3 L, 3 mol) in THF. The resulting mixture was then treated at −70° C. with ethyl 2-chloro-2-oxoacetate (403 g, 2962 mmol) and mixture was aged at −70° C. for 1 hourour. The reaction was quenched with saturated aqueous KHSO$_4$ and extracted with EtOAc. The combined organic phase was washed with brine, dried over anhydrous Na$_2$SO$_4$ and concentrated in vacuo to provide the crude product. The residue was diluted with toluene and concentrated in vacuo. Toluene (6 L) and triethylamine (600 mL) were were added and the mixture was allowed to stir at room temperature for 1 hour and then concentrated in vacuo. The crude product was purified using flash column chromatography on silica gel column (PE:EA=100:1 to 10:1) to provide 3e as a solid. $^1$H NMR (400 MHz, CDCl$_3$) δ 8.41 (s, 1H), 4.43-4.42 (m, 2H), 4.03 (s, 2H), 1.57 (s, 9H), 1.43-1.39 (t, J=7.2, 3H).

Step E—Synthesis of Intermediate Compound 3f

To a stirred solution of the 3e (140 g, 469 mmol) in EtOAc (140 mL) at 0° C. was added HCl/EtOAc (4 N, 1400 mL). The resulting mixture was allowed to stir at room temperature for 1 hour and then concentrated in vacuo. To the resulting residue was added hexane (1.4 L). The resulting mixture was allowed to stir at room temperature to provide a precipitate. The mixture was filtered and the solid ws collected and dried in vacuo to provide 3f.

Steps F—Synthesis of Compound 3

To a stirred solution of the 3f (10 g, 41.3 mmol) in toluene (200 mL) was added oxalyl chloride (60 mL) and DMF (0.6 mL) at 0° C. under N$_2$. The resulting mixture was allowed to stir at room temperature for 2 hours and then the mixture was concentrated in vacuo. The residue was dissolved in CHCl$_3$ (300 mL), treated with 4 (12.5 g, 61.9 mmol) and aged at room temperature for 16 hours. The crude product was recrystallized from petroleum ether and ethyl acetate to provide 3 as a solid. $^1$H NMR (400 MHz, CDCl$_3$) δ 9.08 (s, 1H), 7.33-7.27 (m, 1H), 6.89-6.84 (m, 2H), 4.49-4.44 (m, 4H), 4.08 (s, 3H), 1.45-1.42 (t, J=7.2, 3H).

Example 4

Preparation of Intermediate Compound 4

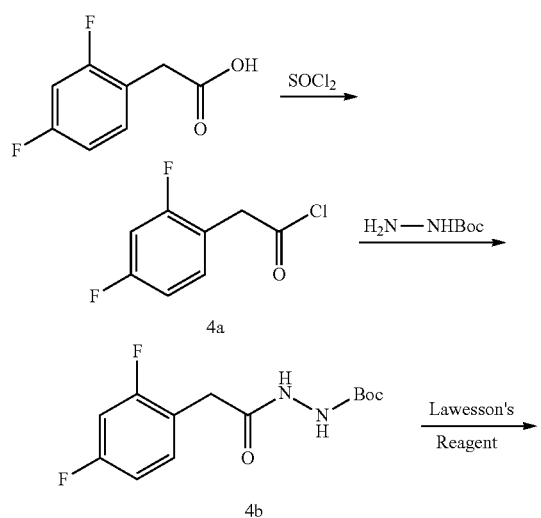

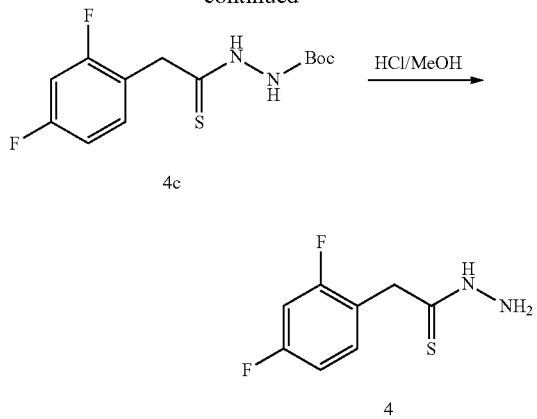

Step A—Synthesis of Intermediate Compound 4a

To a solution of 2-(2,4-difluorophenyl)acetic acid (100 g, 0.58 mol) in anhydrous dichloromethane (1000 mL) was added thionyl chloride (200 mL) at 0° C. After addition was complete, the mixture was heated at reflux and stirred overnight. The solution was concentrated in vacuo to provide the crude compound 4a as an oil that was used without further purification.

Step B—Synthesis of Intermediate Compound 4b

To a solution of BocNHNH2 (48 g, 0.64 mol) and triethylamine (110 mL, 0.72 mol) in anhydrous dichloromethane (600 mL) was added a solution of crude compound 4a (100 g, 0.53 mol) in anhydrous dichloromethane (1000 mL) at 0° C. After addition ws complete, the mixture was warmed up to room temperature and stirred for 2 hrs. The mixture was quenched by the addition of water (500 mL). The two phases were separated and the aqueous layer was extracted with dichloromethane (500 mL×2). The organic layer was washed with water (500 mL×4), brine, dried over anhydrous Na$_2$SO$_4$, and concentrated in vacuo to provide 4b as a solid.

Step C—Synthesis of Intermediate Compound 4c

A mixture of compound 4b (50 g, 0.19 mol) and Lawesson's reagent (105 g, 0.25 mol) in THF (600 mL) was allowed to stir at 50° C. for 2 hours. The mixture was then poured into 10% aqueous Na$_2$CO$_3$ (1 L) and extracted with ethyl acetate (1 L×3). The combined organic layer was washed with brine (500 mL), dried over anhydrous Na$_2$SO$_4$ and concentrated in vacuo to provide compound 4c as a solid.

Step D—Synthesis of Compound 4

The suspension of 4c (70 g, 23 mmol) in HCl/methanol (500 mL, 4N) was allowed to stir at room temperature for 1 hour. The mixture was filtered and the filtrate was concentrated in vacuo to provide 4 as the HCl salt. The solid was dissolved in water and the aqueous layer was adjusted to pH=10 with 10% of aqueous Na$_2$CO$_3$. The solution was extracted with EtOAc (200 mL*6). The combined organic phase was washed with brine (500 mL), dried over Na$_2$SO$_4$, and concentrated in vacuo to provide 4 as a solid. $^1$H NMR (400 MHz, CDCl$_3$) d 8.51 (br, 1H), 7.35-7.37 (d, 1H), 6.84-6.91 (m, 2H), 4.2 (br, 2H), 4.0 (s, 2H).

Example 5

Preparation of Compound 5

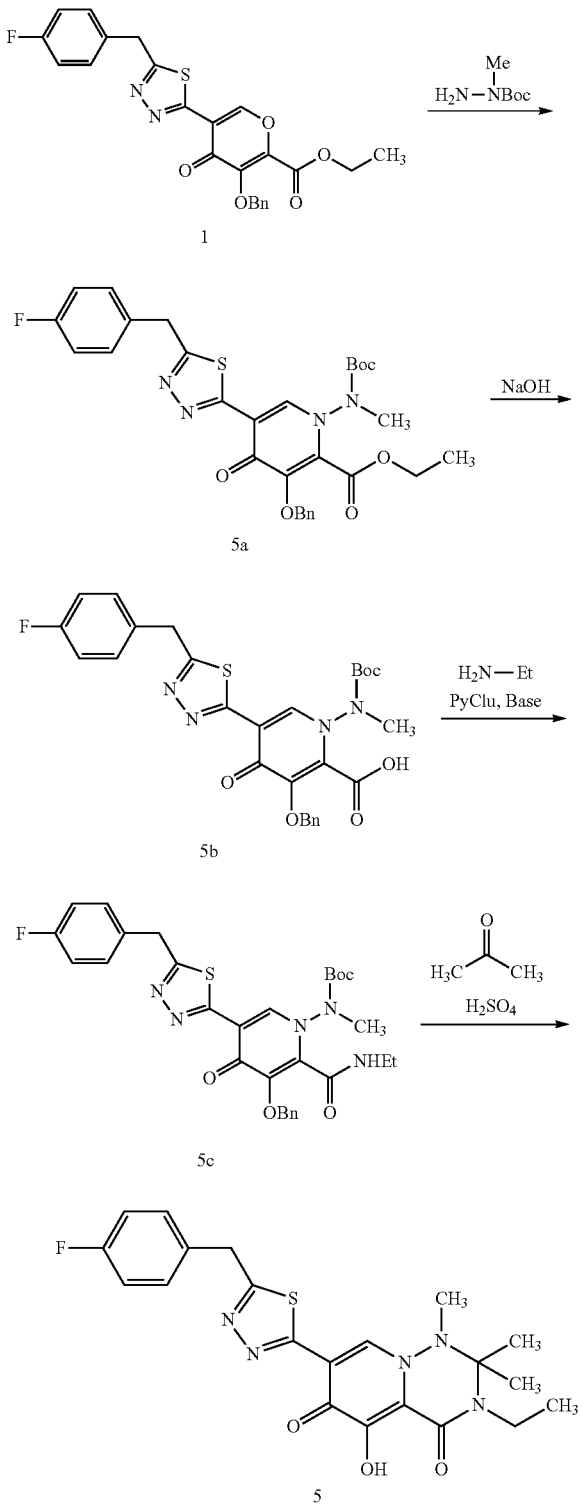

Step A—Synthesis of Intermediate Compound 5a

Compound 1 (3.0 g, 6.4 mmol) in ethanol (10 ml) was treated with tert-butyl 1-methylhydrazinecarboxylate (2.4 g, 16 mmol) and stirred at 80° C. for 4 hours. Aqueous HCl (2M, 3.2 ml, 6.4 mmol) was added and the solution stirred for 16 hours at 80° C. The solution was cooled to room temperature and concentrated in vacuo. The residue was taken up in dichloromethane and washed with saturated aqueous $NaHCO_3$. The organic layer was dried, concentrated in vacuo, and purified using flash column chromatography on silica gel (40% EtOAc/hexanes) to provide intermediate compound 5a. $^1$H NMR ($CDCl_3$, 400 MHz) 8.67 (s, 1H), 7.43-7.40 (m, 2H), 7.36-7.30 (m, 5H), 7.05-7.00 (m, 2H), 5.42-5.35 (bs, 1H), 5.31-5.26 (bs, 1H), 4.45 (s, 2H), 4.31-4.28 (m, 2H), 3.38 (s, 3H), 1.40 (s, 9H), 1.25 (t, 3H); LCMS (M+H)=595.0

Step B—Synthesis of Intermediate Compound 5b

Ethyl 3-(benzyloxy)-1-((tert-butoxycarbonyl)(methyl)amino)-5-(5-(4-fluorobenzyl)-1,3,4-thiadiazol-2-yl)-4-oxo-1,4-dihydropyridine-2-carboxylate 5a (0.10 g, 0.17 mmol) in THF (0.50 ml)/water (0.17 ml)/methanol (0.17 ml) was added sodium hydroxide (0.21 ml, 0.42 mmol) and stirred for 16 hours at 25° C. Neutralize with 2N HCl (0.21 ml) and concentrate. The solid was taken up in Dichloromethane/Methanol and filtered. The filtrate was concentrated in vacuo and the resulting residue was purified using RP-HPLC to provide intermediate compound 5b. $^1$H NMR (CDCl3, 400 MHz) 8.78 (s, 1H), 7.43-7.41 (m, 2H), 7.34-7.28 (m, 5H), 7.04-7.00 (m, 2H), 5.45 (s, 2H), 4.45 (s, 2H), 3.39 (s, 3H), 1.41 (s, 9H), LCMS (M+H)=567.1

Step C—Synthesis of Intermediate Compound 5c 3-(benzyloxy)-1-((tert-butoxycarbonyl)(methyl)amino)-5-(5-(4-fluorobenzyl)-1,3,4-thiadiazol-2-yl)-4-oxo-1,4-dihydropyridine-2-carboxylic acid 5b (0.16 g, 0.29 mmol) in dichloromethane (1.4 ml) was added 1-(chloro-1-pyrrolidinylmethylene)pyrrolidinium hexafluorophosphate (0.096 g, 0.29 mmol) followed by ethylamine (0.15 ml, 0.29 mmol) and N,N-diisopropylethylamine (0.20 ml, 1.2 mmol). The reaction stirred for 30 minutes and was added another equivalent of PyClu and ethylamine After stirring for an additional 1 hour the solution was extracted with dichloromethane and washed with saturated $NaHCO_3$. The organic layer was dried, concentrated in vacuo, and purified using RP-HPLC to provide intermediate compound 5c. $^1$H NMR ($CDCl_3$, 400 MHz) 8.68 (s, 1H), 7.38-7.29 (m, 7H), 7.04-7.00 (m, 2H), 5.85 (bs, 1H), 5.57 (d, 1H), 5.11 (d, 1H), 4.45 (s, 2H), 3.43 (s, 3H), 3.27-3.20 (m, 2H), 1.45 (s, 9H), 1.02 (t, 3H) LCMS (M+H)=594.1

Step D—Synthesis of Compound 5 (Method A)

tert-butyl (3-(benzyloxy)-2-(ethylcarbamoyl)-5-(5-(4-fluorobenzyl)-1,3,4-thiadiazol-2-yl)-4-oxopyridin-1(4H)-yl)(methyl)carbamate 5c (0.25 g, 0.42 mmol) in dioxane (2.1 ml) was added acetone (0.93 ml, 13 mmol) and sulfuric acid (0.045 ml, 0.84 mmol). The solution was heated at 105° C. for 90 minutes. The mixture was added another 15 equivalents of acetone and an equivalent of sulfuric acid. The solution was heated for an additional 2 hours. Cooled to room temperature, neutralized with saturated $NaHCO_3$ and extracted 3 times with EtOAc. The combined organics were dried and concentrated in vacuo. The residue was purified using RP-HPLC to provide compound 5. $^1$H NMR ($CDCl_3$, 400 MHz) 8.74 (s, 1H), 7.31-7.26 (m, 2H), 7.02-6.98 (m, 2H), 4.43 (s, 2H), 3.74-3.69 (m, 1H), 3.55-3.50 (m, 1H), 2.82 (s, 3H), 1.69 (s, 3H), 1.46 (s, 3H), 1.32 (t, 3H) LCMS (M+H)=444.0.

The compounds set forth in the table below were prepared using the method described above and substituting the appropriate reactants and reagents:

| No. | Compound | Stereo-chemistry | Exact Mass [M + H]+ |
|---|---|---|---|
| 217 | | racemate | 456 |
| 218 | | — | 469 |
| 219 | | racemate | 500 |
| 220 | | — | 416 |

Example 6

Preparation of Compound 6

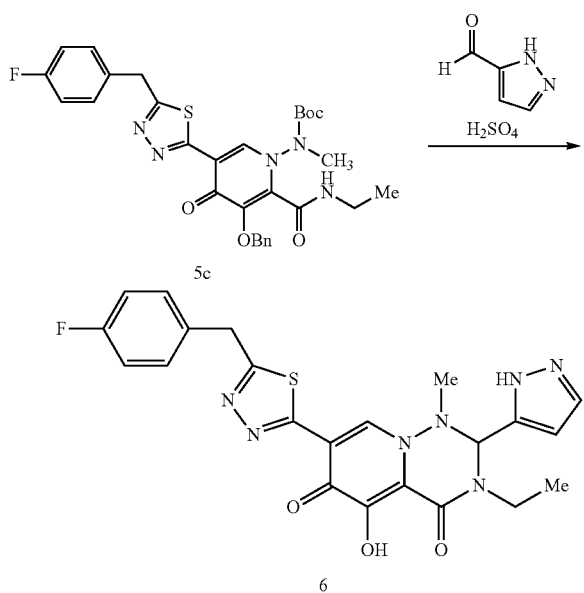

Synthesis of Compound 6 (Method B)

tert-butyl (3-(benzyloxy)-2-(ethylcarbamoyl)-5-(5-(4-fluorobenzyl)-1,3,4-thiadiazol-2-yl)-4-oxopyridin-1(4H)-yl)(methyl)carbamate 5c (12 mg, 0.020 mmol) in DCM (0.1 mL) and TFA (0.14 mL) stirred for 10 minutes at room temperature. To this solution was added 1H-pyrazole-5-carbaldehyde (49 mg, 0.51 mmol). The reaction was heated at 60° C. for 45 minutes allowing the DCM to evaporate from the reaction. Cooled to room temperature, diluted with methanol and DMSO and directly purified using RP-HPLC to provide compound 6. $^1$H NMR (500 MHz, DMSO): δ 8.56 (s, 1 H); 7.67 (d, J=2.5 Hz, 1 H); 7.38 (t, J=6.9 Hz, 2 H); 7.17 (t, J=8.7 Hz, 2 H); 6.27 (d, J=2.5 Hz, 1 H); 6.17 (s, 1 H); 4.46 (s, 2 H); 4.00-3.95 (m, 1 H); 3.17-3.21 (1 H, m); 3.10 (s, 3 H); 1.23 (t, J=7.2 Hz, 3 H); LCMS (M+H)=482.2

The compounds set forth in the table below were prepared using the method described above and substituting the appropriate reactants and reagents:

| No. | Compound | Stereo-chemistry | Exact Mass [M + H]+ |
|---|---|---|---|
| 221 | (structure) | — | 456 |
| 222 | (structure) | — | 484 |

-continued
| No. | Compound | Stereo-chemistry | Exact Mass [M + H]+ |
|---|---|---|---|
| 223 | 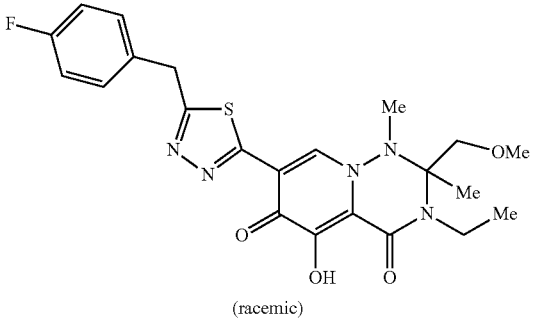 [SMILES: CCN1C(=O)c2c(O)c(=O)c(-c3nnc(Cc4ccc(F)cc4)s3)cn2N(C)C1(C)COC] (racemic) | racemate | 474 |
| 224 | 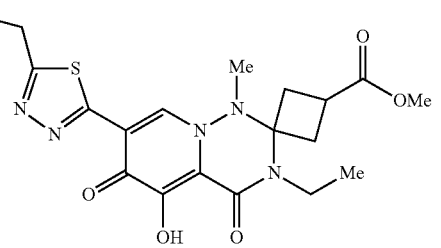 | mixture of diastereomers | 514 |
| 225 | 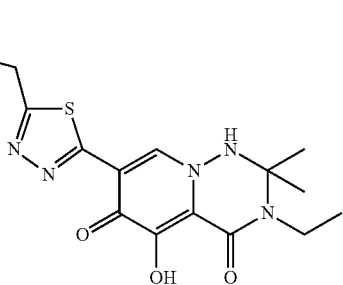 | — | 430 |
| 226 | 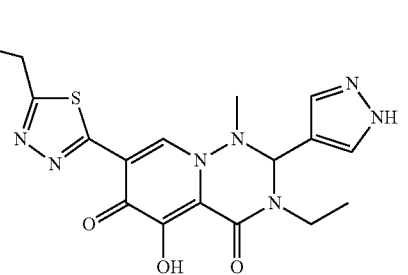 | racemate | 482 |

Example 7

Preparation of Compound 7

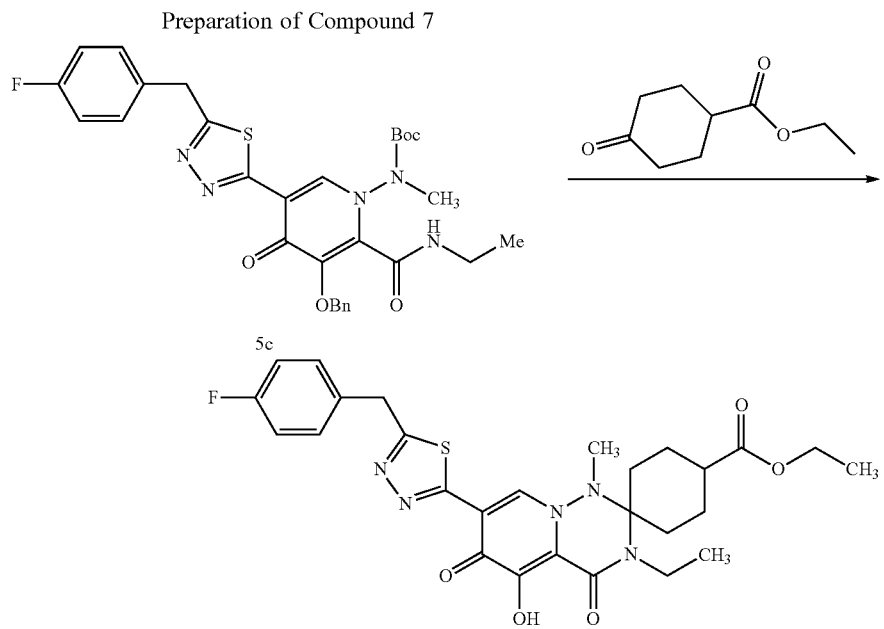

tert-butyl (3-(benzyloxy)-2-(ethylcarbamoyl)-5-(5-(4-fluorobenzyl)-1,3,4-thiadiazol-2-yl)-4-oxopyridin-1(4H)-yl)(methyl)carbamate (40 mg, 0.067 mmol) and ethyl 4-oxocyclohexanecarboxylate (57.3 mg, 0.337 mmol) were dissolved in dichloroacetic acid (1.0 ml). The mixture was heated at 100° C. for 2 hours. LCMS indicates SM and intermediate (m/z 404) consumed. Cooled to rt. Diluted with DMSO. Purification by preparative RP-HPLC afforded separate diastereomers of Compound 7, each of which are separate compounds of the present invention. (diastereomer A): LCMS (M+H)=556; $^1$H NMR (500 MHz, DMSO): δ 11.97 (s; 1 H); 8.76 (s; 1 H); 7.39 (dd; J=8.4; 5.5 Hz; 2 H); 7.17 (t; J=8.8 Hz; 2 H); 4.48 (s; 3 H); 4.08 (q; J=7.1 Hz; 3 H); 3.68-3.60 (m; 1 H); 3.50-3.56 (m; 1 H); 2.74 (s; 3 H); 2.16-2.21 (m; 2 H); 1.91 (bs; 1 H); 1.68-1.78 (m; 4 H); 1.19 (t; J=7.1 Hz; 6 H). (diastereomer B): LCMS (M+H)=556; $^1$H NMR (500 MHz, DMSO): δ 11.97 (s; 1 H); 8.81 (s; 1 H); 7.39 (t; J=6.6 Hz; 2 H); 7.17 (t; J=8.7 Hz; 2 H); 4.48 (s; 3 H); 4.12 (q; J=7.1 Hz; 3 H); 3.50-3.57 (m; 1 H); 2.74 (s; 3 H); 1.78-2.20 (m; 8 H); 1.20 (t; J=7.1 Hz; 3 H); 1.16 (t; J=7.0 Hz; 3 H).

Example 8

Preparation of Intermediate Compound 8-1 and Intermediate Compound 8-2

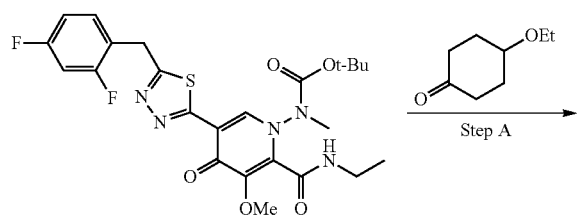

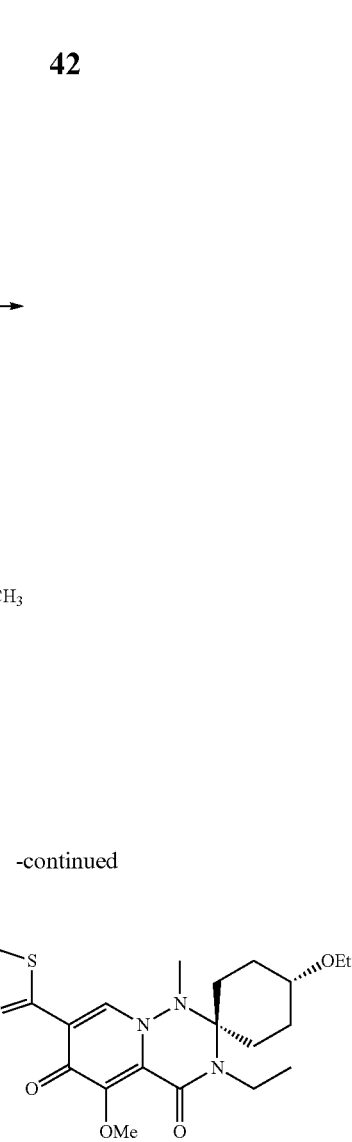

Step A—Synthesis of Intermediate Compound 8-1 and Intermediate Compound 8-2 (Method C)

tert-butyl (5-(5-(2,4-difluorobenzyl)-1,3,4-thiadiazol-2-yl)-2-(ethylcarbamoyl)-3-methoxy-4-oxopyridin-1(4H)-yl)(methyl)carbamate (500 mg, 0.934 mmol) and 4-ethoxycyclohexanone (670 mg, 4.71 mmol) were mixed in dichloroacetic acid (2 mL). The reaction mixture heated at 100° C. for 6 hours. The mixture was cooled to room temperature and diluted with DMSO. Purification by preparative reverse phase HPLC to provide separate diastereomers intermediate compound 8-1: LCMS (M+H)=560 and intermediate compound 8-2: LCMS (M+H)=560.

Example 9

Preparation of Compound 9

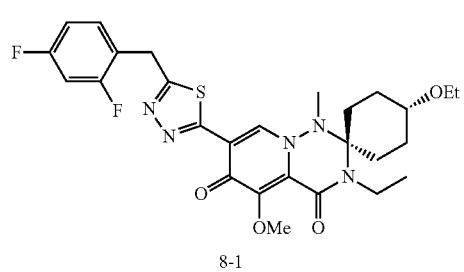

Step A—Synthesis of Compound 9

A mixture of 7'-(5-(2,4-difluorobenzyl)-1,3,4-thiadiazol-2-yl)-4-ethoxy-3'-ethyl-5'-methoxy-1'-methylspiro[cyclohexane-1,2'-pyrido[2,1-f][1,2,4]triazine]-4',6'(1'H,3'H)-dione 8-1 (332 mg, 0.593 mmol) and lithium chloride (252 mg, 5.93 mmol) in DMF (3 mL) were heated at 100° C. for 2 hours, cooled to room temperature and and diluted with DMSO. Direct purification by preparative RP-HPLC afforded compound 9. LCMS (M+H)=546; $^1$H NMR (500 MHz, DMSO): δ 8.80 (s; 1 H); 7.50-7.55 (m; 1 H); 7.26-7.30 (m; 1 H); 7.08-7.13 (m; 1 H); 4.50 (s; 2 H); 3.61-3.67 (m; 1 H); 3.36-3.56 (m; 4 H); 2.74 (s; 3 H); 2.15-2.17 (m; 2 H); 1.96-1.94 (m, 2 H); 1.70-1.76 (m; 3 H); 1.52-1.62 (m; 2 H); 1.18 (t; J=7.1 Hz; 3 H); 1.11 (t; J=7.0 Hz; 3 H).

Example 10

Preparation of Compound 10

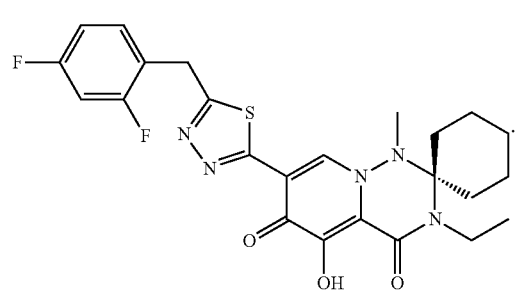

Step A—Synthesis of Compound 10

A mixture of 7'-(5-(2,4-difluorobenzyl)-1,3,4-thiadiazol-2-yl)-4-ethoxy-3'-ethyl-5'-methoxy-1'-methylspiro[cyclohexane-1,2'-pyrido[2,1-f][1,2,4]triazine]-4',6'(1'H,3'H)-dione 8-2 (376.9 mg, 0.673 mmol) and lithium chloride (286 mg, 6.73 mmol) in DMF (4 mL) were heated at 100° C. for 2 hours, cooled to room temperature and and diluted with DMSO. Direct purification by preparative RP-HPLC afforded compound 10. LCMS (M+H)=546; $^1$H NMR (500 MHz, DMSO): δ 8.81 (s; 1 H); 7.49-7.54 (m; 1 H); 7.25-7.29 (m; 1 H); 7.10 (t; J=8.7 Hz; 1 H); 4.49 (s; 2 H); 3.57-3.61 (m; 3 H); 3.38-3.46 (m; 2 H); 2.75 (s; 3 H); 2.26 (dd; J=15.0; 11.8 Hz; 1 H); 1.93 (d; J=13.8 Hz; 1 H); 1.74-1.84 (m; 5 H); 1.60 (d; J=12.6 Hz; 1 H); 1.49 (d; J=12.6 Hz; 1 H); 1.18 (t; J=7.1 Hz; 3 H); 1.13 (t; J=7.0 Hz; 3 H).

The compounds set forth in the table below were prepared using the methods described above and substituting the appropriate reactants and reagents:

| No. | Compound | Stereochemistry | Exact Mass [M + H]+ |
|---|---|---|---|
| 11 | ![structure] | diastereomer | 472 |

-continued
| No. | Compound | Stereo-chemistry | Exact Mass [M + H]+ |
|---|---|---|---|
| 12 | 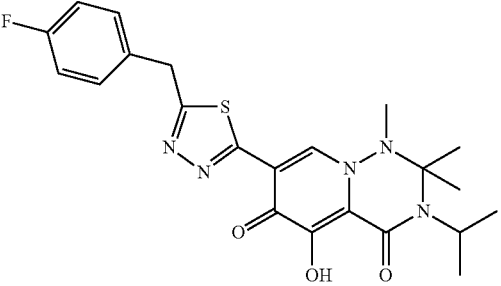 [SMILES: CC(C)N1C(=O)c2c(O)c(=O)c(-c3nnc(Cc4ccc(F)cc4)s3)cn2N(C)C1(C)C] | — | 458 |
| 13 | 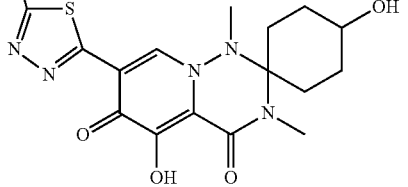 | diastereomer | 486 |
| 14 | 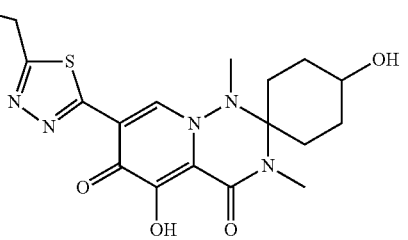 | diastereomer | 486 |
| 15 | 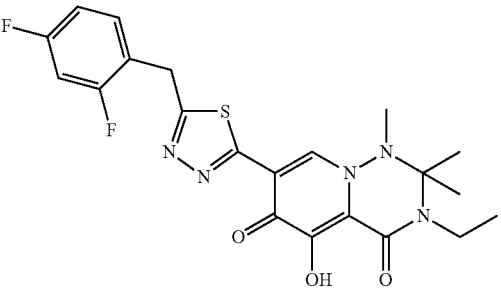 [SMILES: CCN1C(=O)c2c(O)c(=O)c(-c3nnc(Cc4ccc(F)cc4F)s3)cn2N(C)C1(C)C] | — | 462 |
| 16 | 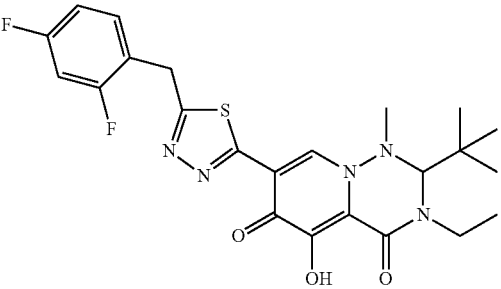 [SMILES: CCN1C(=O)c2c(O)c(=O)c(-c3nnc(Cc4ccc(F)cc4F)s3)cn2N(C)C1C(C)(C)C] | racemate | 490 |

-continued

| No. | Compound | Stereo-chemistry | Exact Mass [M + H]+ |
|---|---|---|---|
| 17 | | racemate | 488 |
| 18 | | racemate | 541 |
| 19 | | mixture of diastereomers | 546 |
| 20 | | mixture of diastereomers | 560 |
| 21 | | mixture of diastereomers | 574 |

-continued

| No. | Compound | Stereo-chemistry | Exact Mass [M + H]+ |
|---|---|---|---|
| 22 | | diastereomer | 571 |
| 23 | | diastereomer | 571 |
| 24 | | mixture of diastereomers | 595 |
| 25 | | mixture of diastereomers | 638 |
| 26 | | diastereomer | 532 |

-continued

| No. | Compound | Stereo-chemistry | Exact Mass [M + H]+ |
|---|---|---|---|
| 27 | | diastereomer | 532 |
| 28 | | diastereomer | 572 |
| 29 | | diastereomer | 572 |
| 30 | | diastereomer | 574 |
| 31 | | diastereomer | 574 |

-continued

| No. | Compound | Stereo-chemistry | Exact Mass [M + H]+ |
|---|---|---|---|
| 32 | | diastereomer | 574 |
| 33 | | diastereomer | 574 |
| 34 | | mixture of diastereomers | 586 |
| 35 | | mixture of diastereomers | 588 |
| 36 | | mixture of diastereomers | 600 |

-continued

| No. | Compound | Stereo-chemistry | Exact Mass [M + H]+ |
|---|---|---|---|
| 37 | | diastereomer | 624 |
| 38 | | diastereomer | 624 |
| 39 | | diastereomer | 500 |
| 40 | | racemate | 490 |
| 41 | | mixture of diastereomers | 492 |

| No. | Compound | Stereo-chemistry | Exact Mass [M + H]+ |
|---|---|---|---|
| 42 | | racemate | 556 |
| 43 | | racemate | 516 |
| 44 | | racemate | 530 |
| 45 | | mixture of diastereomers | 532 |

-continued

| No. | Compound | Stereo-chemistry | Exact Mass [M + H]+ |
|---|---|---|---|
| 46 | | diastereomer | 584 |
| 47 | | diastereomer | 584 |
| 48 | | racemate | 558 |
| 49 | | diastereomer | 570 |

-continued

| No. | Compound | Stereo-chemistry | Exact Mass [M + H]+ |
|---|---|---|---|
| 50 | | diastereomer | 570 |
| 51 | | diastereomer | 518 |
| 52 | | diastereomer | 518 |
| 53 | | diastereomer | 594 |

-continued

| No. | Compound | Stereo-chemistry | Exact Mass [M + H]+ |
|---|---|---|---|
| 54 | | diastereomer | 594 |
| 55 | | diastereomer | 532 |
| 56 | | — | 538 |
| 57 | | diastereomer | 598 |

-continued

| No. | Compound | Stereo-chemistry | Exact Mass [M + H]+ |
|---|---|---|---|
| 58 | | diastereomer | 598 |
| 59 | | diastereomer | 546 |
| 60 | | diastereomer | 560 |
| 61 | | diastereomer | 560 |
| 62 | | diastereomer | 560 |

-continued

| No. | Compound | Stereo-chemistry | Exact Mass [M + H]+ |
|---|---|---|---|
| 63 | | diastereomer | 560 |
| 64 | | diastereomer | 576 |
| 65 | | diastereomer | 576 |
| 66 | | diastereomer | 620 |
| 67 | | diastereomer | 620 |

-continued

| No. | Compound | Stereo-chemistry | Exact Mass [M + H]+ |
|---|---|---|---|
| 68 | | mixture of diastereomers | 614 |
| 69 | | diastereomer | 518 |
| 70 | | diastereomer | 518 |
| 71 | | racemate | 500 |
| 72 | | diastereomer | 532 |

-continued

| No. | Compound | Stereo-chemistry | Exact Mass [M + H]+ |
|---|---|---|---|
| 73 | | diastereomer | 532 |
| 74 | | diastereomer | 518 |
| 75 | | mixture of diastereomers | 503 |
| 76 | | | 502 |
| 77 | | mixture of diastereomers | 530 |

-continued

| No. | Compound | Stereo-chemistry | Exact Mass [M + H]+ |
|---|---|---|---|
| 78 | | racemate | 526 |
| 79 | | mixture of diastereomers | 490 |
| 80 | | diastereomer | 557 |
| 81 | | diastereomer | 557 |
| 82 | | mixture of diastereomers | 545 |

-continued

| No. | Compound | Stereo-chemistry | Exact Mass [M + H]+ |
|---|---|---|---|
| 83 | | diastereomer | 546 |
| 84 | | diastereomer | 546 |
| 85 | | diastereomer | 532 |
| 86 | | diastereomer | 532 |
| 87 | | diastereomer | 550 |

| No. | Compound | Stereo-chemistry | Exact Mass [M + H]+ |
|---|---|---|---|
| 88 | | diastereomer | 532 |
| 89 | | diastereomer | 532 |

Example 11

Preparation of Compound 90

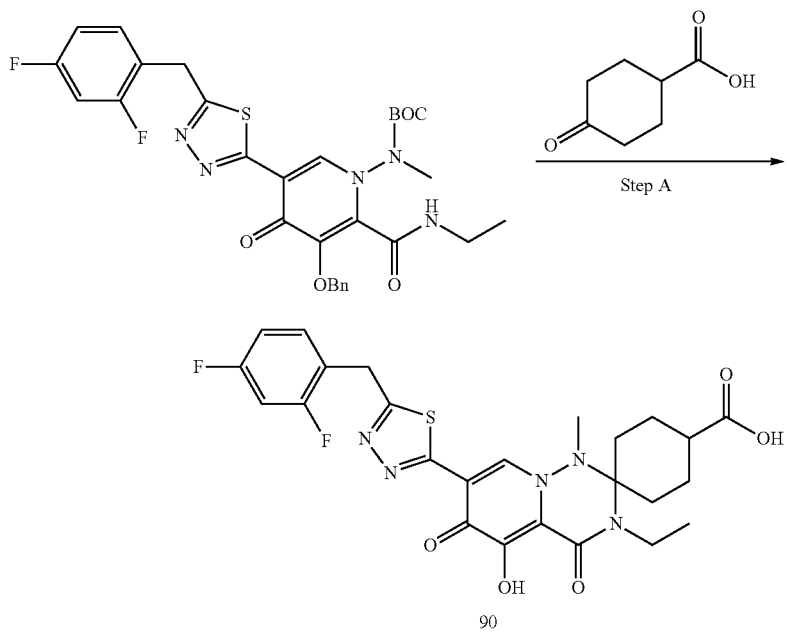

Step A—Synthesis of Compound 8 tert-butyl (3-(benzyloxy)-5-(5-(2,4-difluorobenzyl)-1,3,4-thiadiazol-2-yl)-2-(ethylcarbamoyl)-4-oxopyridin-1(4H)-yl)(methyl)carbamate (400 mg, 0.654 mmol) was stirred with 4-oxocyclohexanecarboxylic acid (465 mg, 3.27 mmol) in dichloroacetic acid (6 mL) at 100° C. for 4 hours. The reaction mixture was partitioned between saturated aqueous NaHCO₃ (20 mL) and EtOAc (100 mL) and the aqueous phase was extracted EtOAc (3×25 mL). The combined organic portion was concentrated and the resulting residue was purified using preparative RP-MPLC to provide intermediate compound 90 that was used without further purification. LCMS (M+H)=546.

Example 12

Preparation of Compound 91 and Compound 92

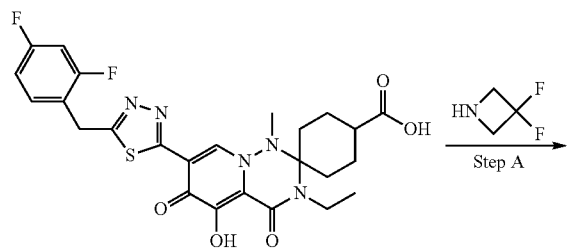

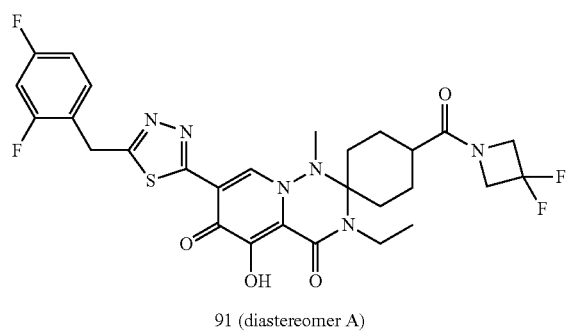

91 (diastereomer A)

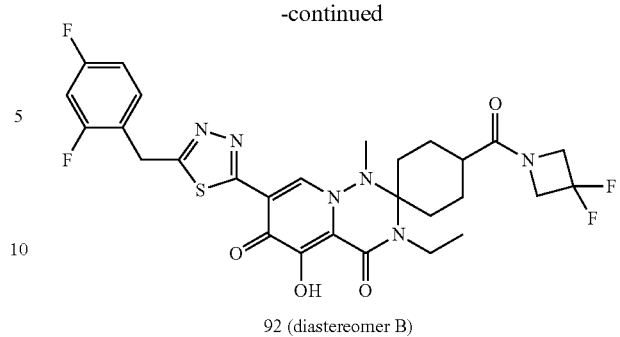

92 (diastereomer B)

A suspension of 7'-(5-(2,4-difluorobenzyl)-1,3,4-thiadiazol-2-yl)-3'-ethyl-5'-hydroxy-1'-methyl-4',6'-dioxo-1',3',4',6'-tetrahydrospiro[cyclohexane-1,2'-pyrido[2,1-f][1,2,4]triazine]-4-carboxylic acid 90 (50 mg, 0.092 mmol) and HATU (52.3 mg, 0.137 mmol) in DMF (1 mL) was treated with N,N-diisopropylethylamine (0.048 mL, 0.275 mmol) and 3,3-difluoroazetidinium hydrochloride (23.74 mg, 0.183 mmol). The reaction mixture was stirred at room temperature for 1 hourour. The mixture was treated with saturated aqueous $K_2CO_3$ (200 uL) and methanol (200 uL) and then stirred at room temperature for 16 hours. The reaction mixture was partioned between EtOAc (10 mL) and water (10 mL). The aqueous was extracted with EtOAc (3×2 mL). The combined organic portion was concentrated in vacuo. The residue was purified using preparative RP-HPLC (C18) to provide the early eluting diastereomer 91 LCMS (M+H)= 621 and the late eluting diastereomer 92 LCMS (M+H)= 621.

The compounds set forth in the table below were prepared using the method described above and substituting the appropriate reactants and reagents:

| No. | Compound | Stereochemistry | Exact Mass [M + H]+ |
|---|---|---|---|
| 93 | | diastereomer | 555 |
| 94 | | diastereomer | 555 |

-continued

| No. | Compound | Stereo-chemistry | Exact Mass [M + H]+ |
|---|---|---|---|
| 95 | | diastereomer | 567 |
| 96 | | diastereomer | 567 |
| 97 | | diastereomer | 569 |
| 98 | | diastereomer | 569 |
| 99 | | mixture of diastereomers | 555 |

| No. | Compound | Stereo-chemistry | Exact Mass [M + H]+ |
|---|---|---|---|
| 100 | | diastereomer | 573 |
| 101 | | diastereomer | 573 |
| 102 | | diastereomer | 641 |
| 103 | | diastereomer | 641 |
| 106 | | diastereomer | 531 |

-continued

| No. | Compound | Stereo-chemistry | Exact Mass [M + H]+ |
|---|---|---|---|
| 107 | | diastereomer | 531 |
| 108 | | Mixture of diastereomers | 627 |
| 109 | | diastereomer | 585 |
| 110 | | diastereomer | 585 |
| 111 | | diastereomer | 613 |

| No. | Compound | Stereo-chemistry | Exact Mass [M + H]+ |
|---|---|---|---|
| 112 | | diastereomer | 613 |
| 113 | | diastereomer | 585 |
| 114 | | diastereomer | 585 |
| 115 | | diastereomer | 585 |
| 116 | | diastereomer | 585 |

-continued

| No. | Compound | Stereo-chemistry | Exact Mass [M + H]+ |
|---|---|---|---|
| 117 | | diastereomer | 621 |
| 118 | | diastereomer | 621 |
| 119 | | diastereomer | 607 |
| 120 | | diastereomer | 607 |
| 121 | | diastereomer | 589 |

-continued

| No. | Compound | Stereo-chemistry | Exact Mass [M + H]+ |
|---|---|---|---|
| 122 | | diastereomer | 589 |
| 123 | | diastereomer | 601 |
| 124 | | diastereomer | 601 |
| 125 | | diastereomer | 602 |
| 126 | | diastereomer | 602 |

| No. | Compound | Stereo-chemistry | Exact Mass [M + H]+ |
|---|---|---|---|
| 127 | 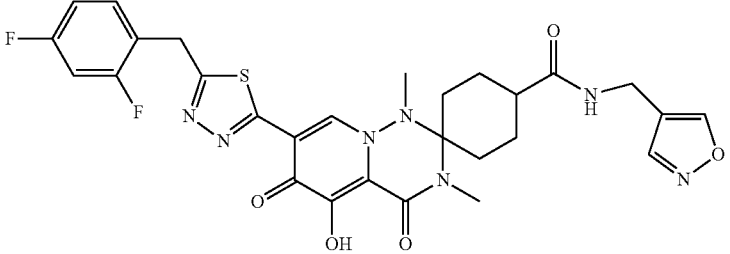 [SMILES: CN1C(=O)c2c(O)c(=O)c(-c3nnc(Cc4ccc(F)cc4F)s3)cn2N(C)C12CCC(C(=O)NCc1cnoc1)CC2] | diastereomer | 612 |
| 128 | 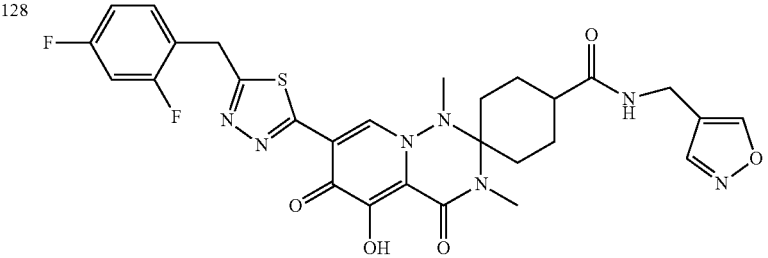 | diastereomer | 612 |
| 129 | 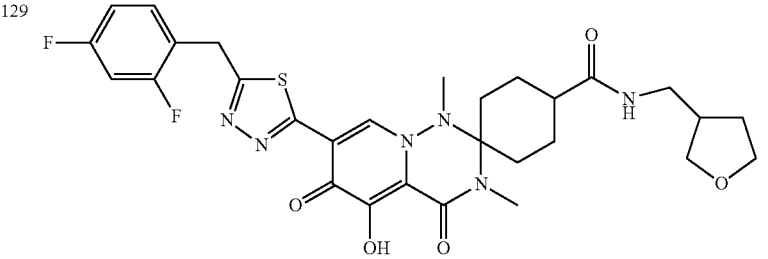 | diastereomer | 615 |
| 130 | 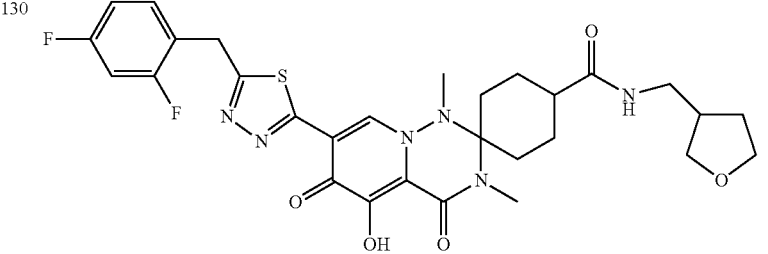 | diastereomer | 615 |
| 131 | 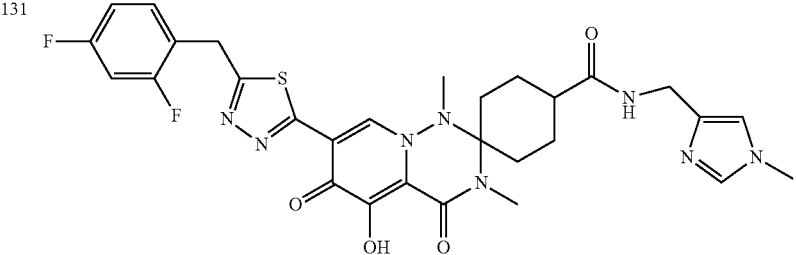 | diastereomer | 625 |

-continued
| No. | Compound | Stereo-chemistry | Exact Mass [M + H]+ |
|---|---|---|---|
| 132 | 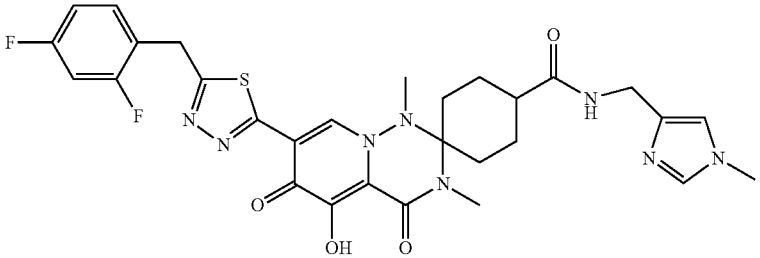 [SMILES: CN1C(=O)c2c(O)c(=O)c(-c3nnc(Cc4ccc(F)cc4F)s3)cn2N(C)C12CCC(C(=O)NCc1cn(C)cn1)CC2] | diastereomer | 625 |
| 133 | 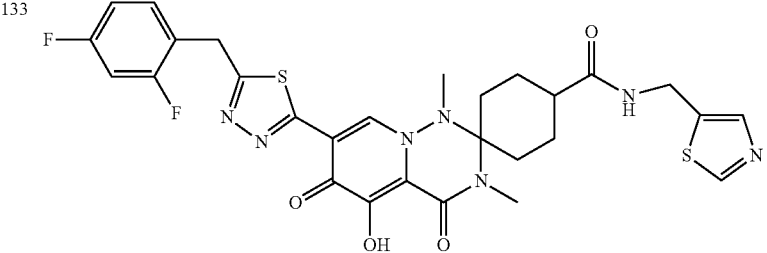 | diastereomer | 628 |
| 134 | 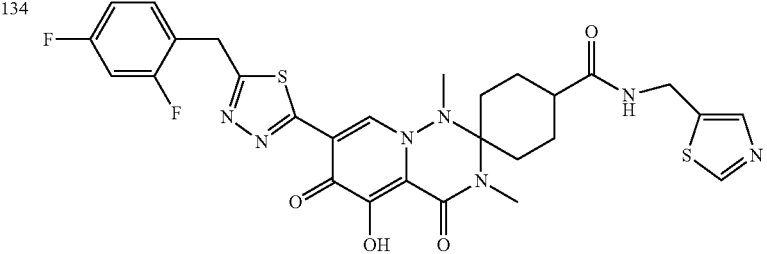 | diastereomer | 628 |
| 135 | 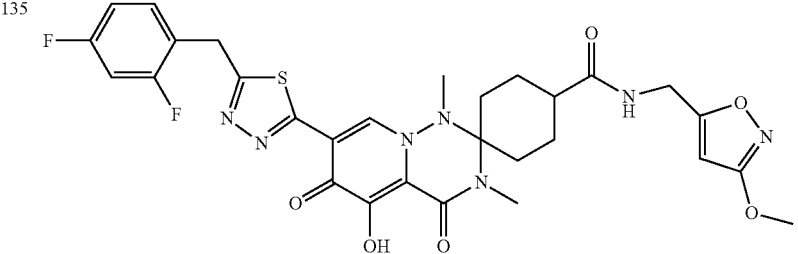 | diastereomer | 642 |
| 136 | 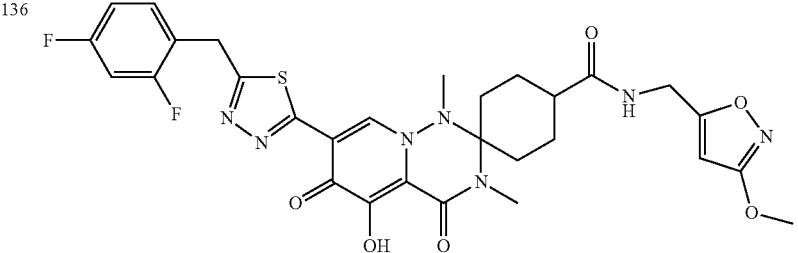 | diastereomer | 642 |

| No. | Compound | Stereo-chemistry | Exact Mass [M + H]+ |
|---|---|---|---|
| 137 | 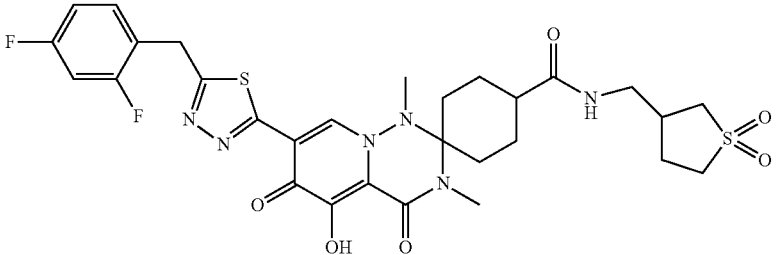 [SMILES: CN1C(=O)c2c(O)c(=O)c(-c3nnc(Cc4ccc(F)cc4F)s3)cn2N(C)C12CCC(C(=O)NCC1CCS(=O)(=O)C1)CC2] | diastereomer | 663 |
| 138 | 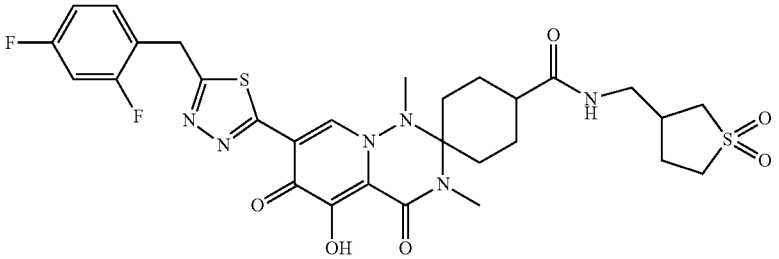 [SMILES: CN1C(=O)c2c(O)c(=O)c(-c3nnc(Cc4ccc(F)cc4F)s3)cn2N(C)C12CCC(C(=O)NCC1CCS(=O)(=O)C1)CC2] | diastereomer | 663 |
| 139 | 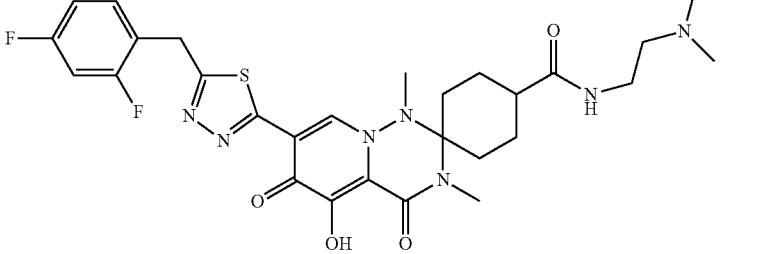 | diastereomer | 688 |
| 140 | 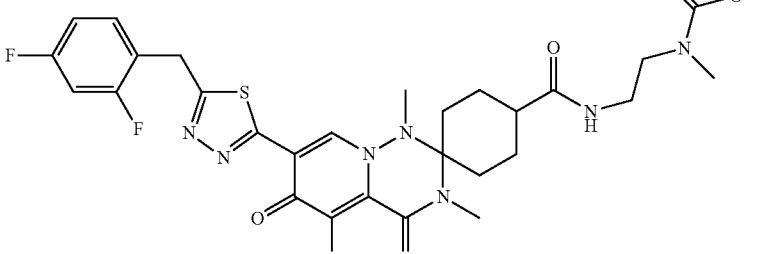 | diastereomer | 688 |
| 141 | 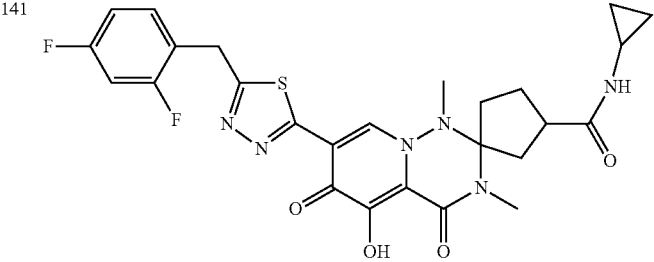 | diastereomer | 557 |

| No. | Compound | Stereo-chemistry | Exact Mass [M + H]+ |
|---|---|---|---|
| 142 | 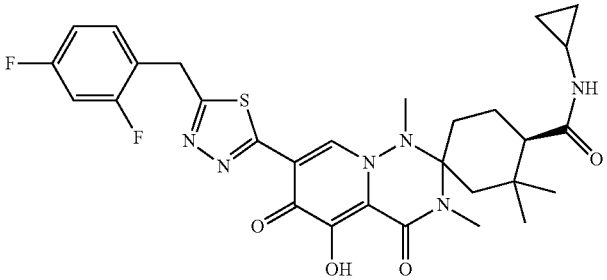 [SMILES: CN1C(=O)c2c(O)c(=O)c(-c3nnc(Cc4ccc(F)cc4F)s3)cn2N(C)C12CC[C@@H](C(=O)NC1CC1)C(C)(C)C2] | diastereomer | 599 |
| 143 | 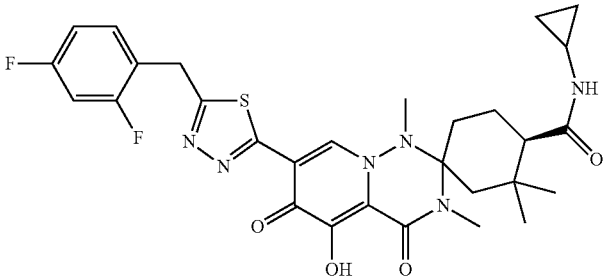 [SMILES: CN1C(=O)c2c(O)c(=O)c(-c3nnc(Cc4ccc(F)cc4F)s3)cn2N(C)C12CC[C@@H](C(=O)NC1CC1)C(C)(C)C2] | diastereomer | 599 |
| 144 | 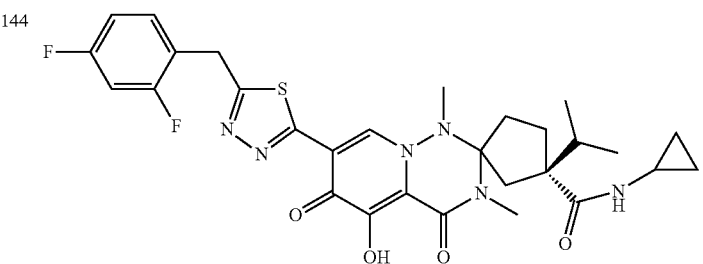 | diastereomer | 599 |
| 145 | 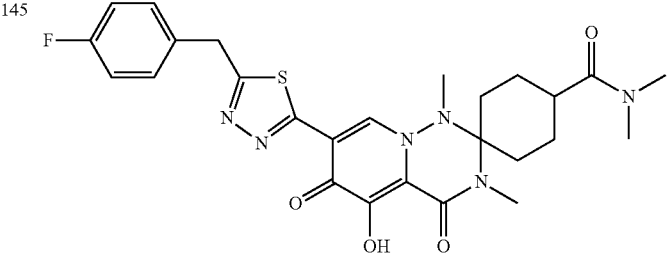 | diastereomer | 541 |
| 146 | 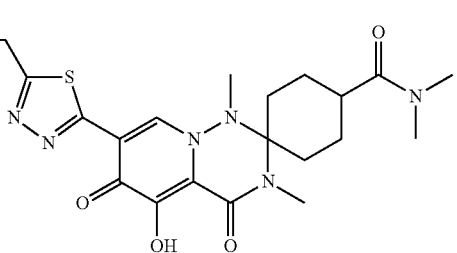 | diastereomer | 541 |

-continued

| No. | Compound | Stereo-chemistry | Exact Mass [M + H]+ |
|---|---|---|---|
| 147 | | diastereomer | 555 |
| 148 | | diastereomer | 555 |
| 149 | | Mixture of diastereomers | 555 |
| 150 | | diastereomer | 555 |
| 151 | | diastereomer | 513 |

-continued
| No. | Compound | Stereo-chemistry | Exact Mass [M + H]+ |
|---|---|---|---|
| 152 | 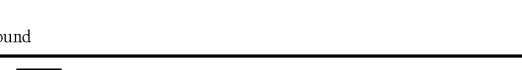 | diastereomer | 513 |
Example 13
Preparation of Compound 153 and Compound 154
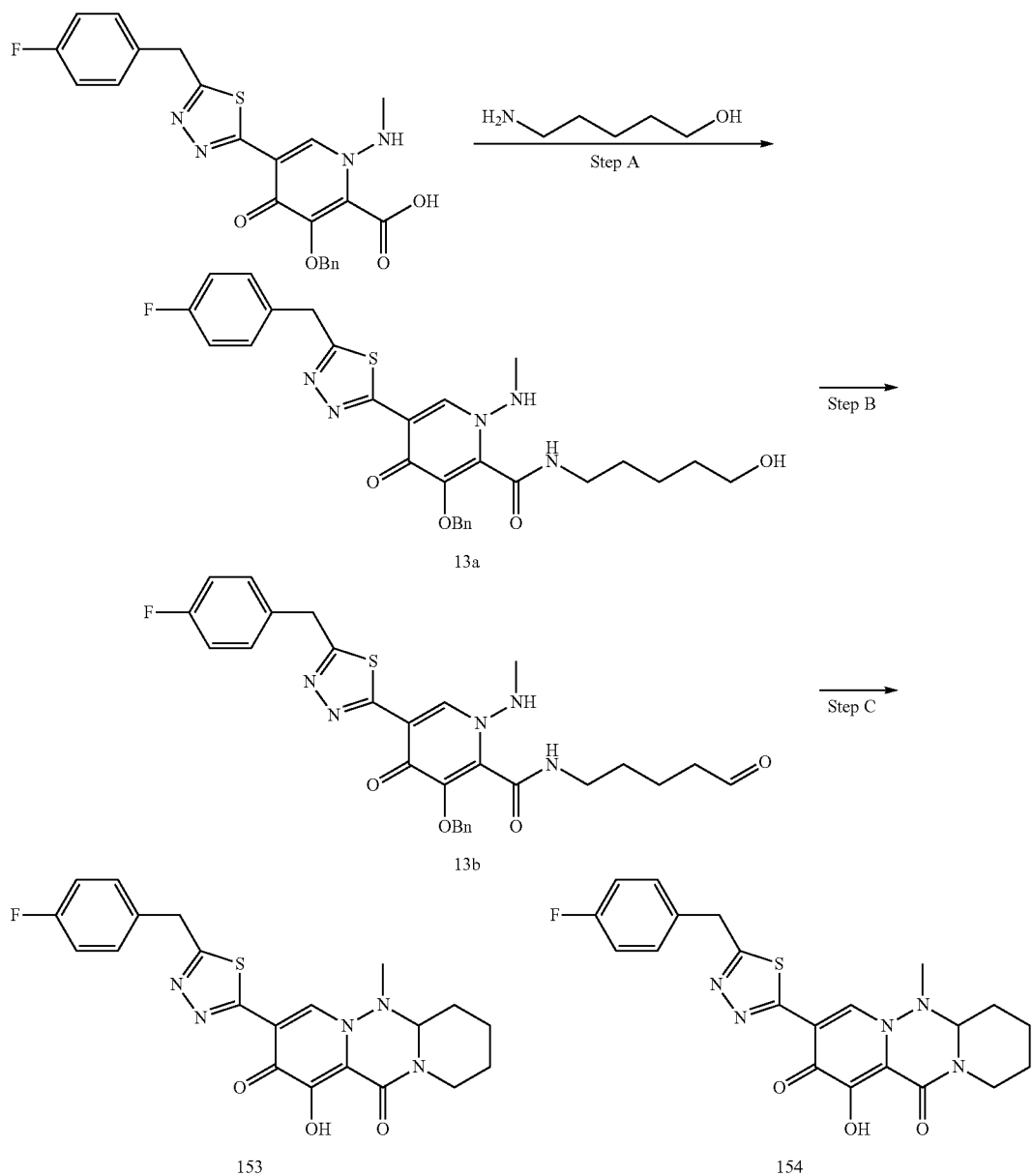

Step A—Synthesis of Intermediate Compound 13a 3-(benzyloxy)-5-(5-(4-fluorobenzyl)-1,3,4-thiadiazol-2-yl)-1-(methylamino)-4-oxo-1,4-dihydropyridine-2-carboxylic acid (88 mg, 0.189 mmol) in DMF (2 mL) was treated at room temperature with HATU (108 mg, 0.283 mmol) and 5-amino-1-pentanol (41.0 mg, 0.377 mmol) and N,N-diisopropylethylamine (0.099 mL, 0.566 mmol). The mixture was allowed to stir at room temperature 2 hours. The reaction mixture was partitioned between dichloromethane (10 mL) and LiCl (0.1M, 10 mL) and the aqueous was extracted with dichloromethane (3×5 mL). The combined organic portion was dried over anhydrous $Na_2SO_4$, filtered and the filtrate was concentration to provide 13a that was used without further purification. LCMS (M+H)=552.

Step B—Synthesis of Intermediate Compound 13b

Compound 13a (104 mg, 0.189 mmol) in dichloromethane (2 mL) was treated with Dess-Martin periodinane (120 mg, 0.283 mmol) and stirred for 2 hours. The reaction mixture was partitioned between dichloromethane (10 mL) and saturated aqueous $NaHCO_3$ and the aqueous was extracted with dichloromethane (3×2 mL). The combined organic portion was dried over anhydrous $Na_2SO_4$, filtered and the filtrate was concentrated in vacuo. The residue was purified using flash column chromatography on silica gel (0 to 10% Methanol/dichloromethane) afford intermediate compound 13b as an oil. LCMS (M+H)=550

Step C—Synthesis of Intermediate Compound 153 and Compound 154

Compound 13b (104 mg, 0.189 mmol) in TFA (10 mL, 130 mmol) was allowed to stir at room temperature for 2 hours. The reaction mixture was diluted with DMSO (4 mL) and water (1 mL). Direct purification by preparative reverse phase HPLC followed by resolution of the enantiomers was accomplished by SFC [4.6×250 mm Chiralcel OD, 2.1 mL/min, 100 Bar, 40% (2:1 IPA: ACN+0.3% DEA), 35C] to provide the separate enantiomers. Compound 153: LCMS (M+H)=442; $^1$H NMR (500 MHz, DMSO): δ 13.01 (br s; 1 H); 9.23 (s; 1 H); 7.96 (t; J=6.7 Hz; 2 H); 7.67 (t; J=8.6 Hz; 2 H); 5.15 (d; J=10.6 Hz; 1 H); 5.08 (d; J=13.5 Hz; 1 H); 5.00 (s; 2H); 3.54 (s; 3 H); 3.47-3.56 (m, 1H); 2.25 (t; J=13.5 Hz; 4 H); 1.85 (s; 2 H). Compound 154: LCMS (M+H)=442; $^1$H NMR (500 MHz, DMSO): δ 13.00 (br s; 1 H); 9.23 (s; 1 H); 7.96 (s; 2 H); 7.66 (t; J=8.4 Hz; 2 H); 5.15 (d; J=10.8 Hz; 1 H); 5.07 (d; J=13.5 Hz; 1 H); 5.00 (s; 3 H); 3.54 (s; 4 H); 3.48-3.52 (m; 1 H); 2.25 (s; 2 H); 1.85 (s; 2 H).

The compounds set forth in the table below were prepared using the method described above in Example 13 and substituting the appropriate reactants and reagents:

| No. | Structure | Stereochemistry | Exact Mass [M + H]+ |
|---|---|---|---|
| 155 | 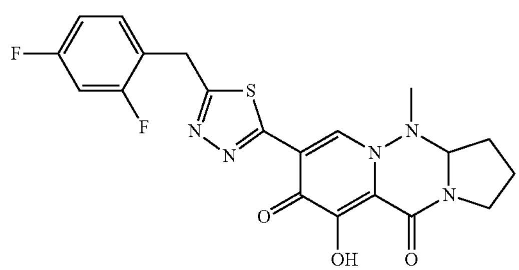 [SMILES: CN1C2CCCN2C(=O)c2c(O)c(=O)c(-c3nnc(Cc4ccc(F)cc4F)s3)cn21] | racemate | 446 |
| 156 | 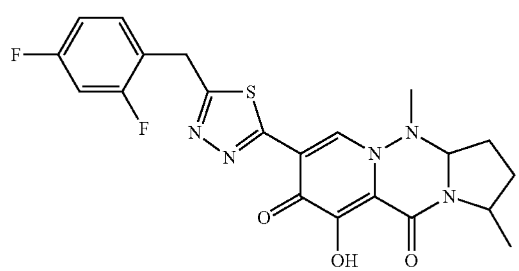 [SMILES: CC1CCC2N1C(=O)c1c(O)c(=O)c(-c3nnc(Cc4ccc(F)cc4F)s3)cn1N2C] | Mixture of diastereomers | 460 |
| 157 | 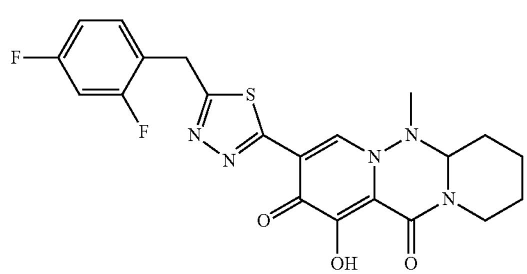 [SMILES: CN1C2CCCCN2C(=O)c2c(O)c(=O)c(-c3nnc(Cc4ccc(F)cc4F)s3)cn21] | enantiomer | 460 |

-continued
| No. | Structure | Stereo-chemistry | Exact Mass [M + H]+ |
|---|---|---|---|
| 158 | 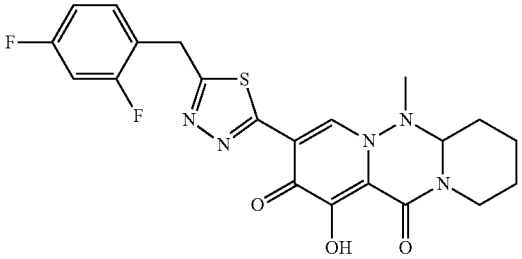 [SMILES: CN1C2CCCCN2C(=O)c2c(O)c(=O)c(-c3nnc(Cc4ccc(F)cc4F)s3)cn21] | enantiomer | 460 |
| 159 | 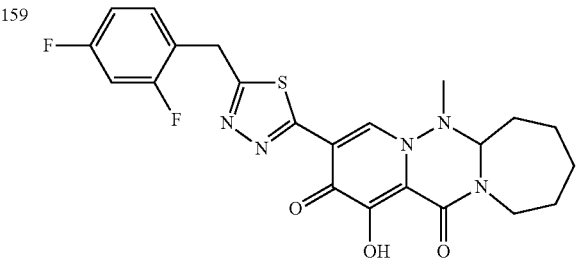 | racemate | 474 |
| 160 | 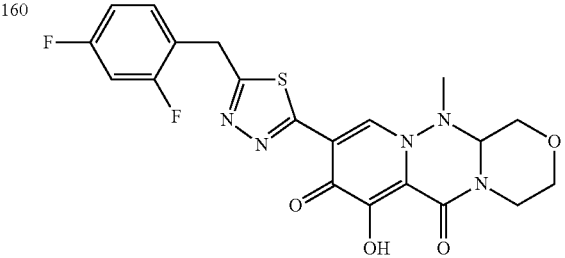 | racemate | 462 |
| 161 | 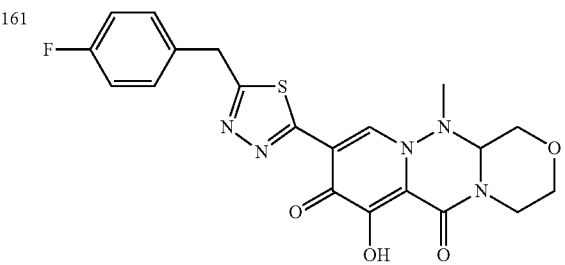 | enantiomer | 444 |
| 162 | 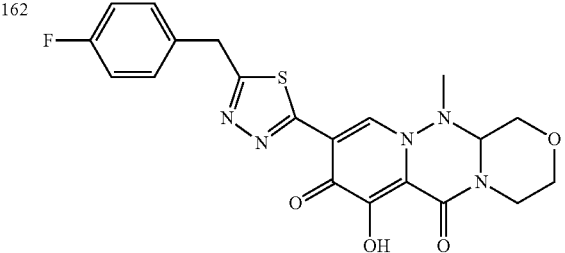 | enantiomer | 444 |

-continued

| No. | Structure | Stereo-chemistry | Exact Mass [M + H]+ |
|---|---|---|---|
| 163 | 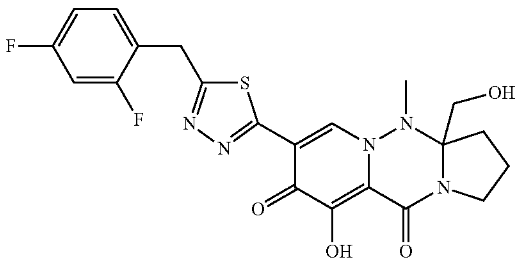 [SMILES: CN1n2cc(-c3nnc(Cc4ccc(F)cc4F)s3)c(=O)c(O)c2C(=O)N2CCCC21CO] | racemate | 476 |
| 164 | 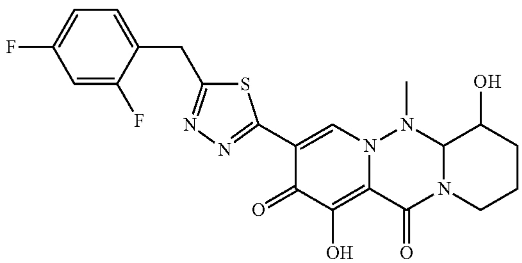 [SMILES: CN1C2C(O)CCCN2C(=O)c2c(O)c(=O)c(-c3nnc(Cc4ccc(F)cc4F)s3)cn21] | enantiomer | 476 |
| 165 | 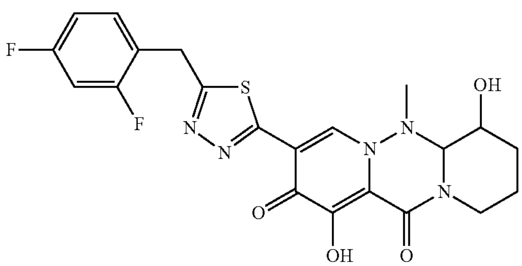 [SMILES: CN1C2C(O)CCCN2C(=O)c2c(O)c(=O)c(-c3nnc(Cc4ccc(F)cc4F)s3)cn21] | enantiomer | 476 |
| 166 | 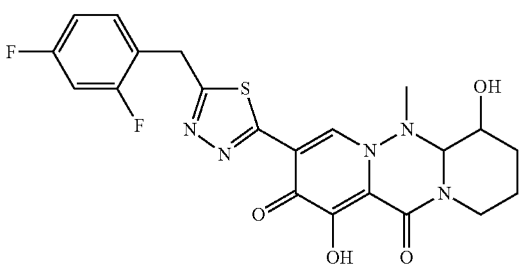 [SMILES: CN1C2C(O)CCCN2C(=O)c2c(O)c(=O)c(-c3nnc(Cc4ccc(F)cc4F)s3)cn21] | enantiomer | 476 |
| 167 | 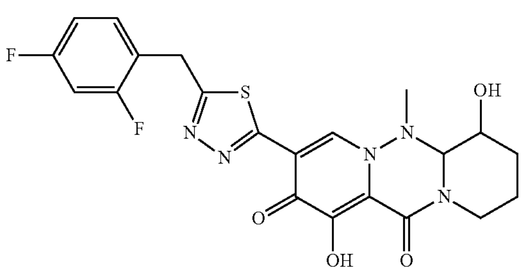 [SMILES: CN1C2C(O)CCCN2C(=O)c2c(O)c(=O)c(-c3nnc(Cc4ccc(F)cc4F)s3)cn21] | enantiomer | 476 |

Example 14

Preparation of Compound 168

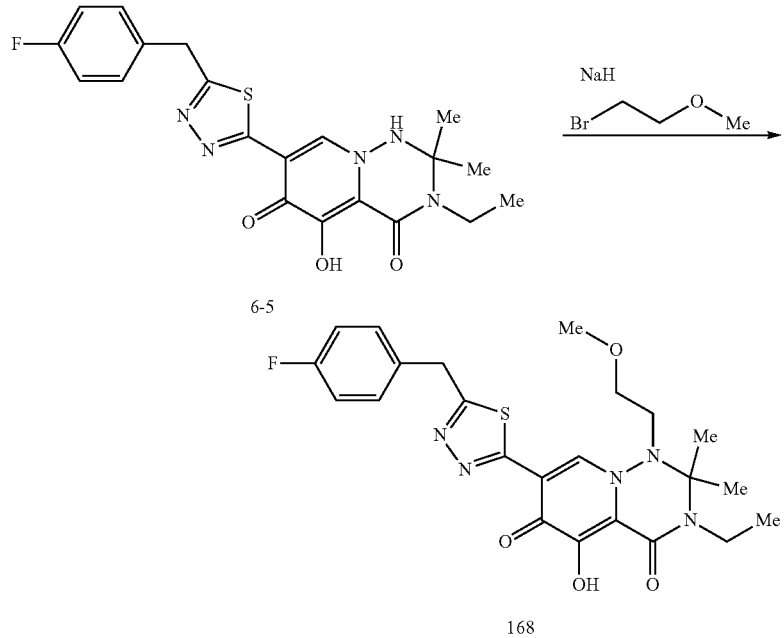

In a flame dried flask, under an atmosphere of nitrogen, 3-ethyl-7-(5-(4-fluorobenzyl)-1,3,4-thiadiazol-2-yl)-5-hydroxy-2,2-dimethyl-2,3-dihydro-1H-pyrido[2,1-f][1,2,4]triazine-4,6-dione 6-5 (25 mg, 0.058 mmol) was dissolved in anhydrous DMF (1 mL). To this was added sodium hydride ((95%), 6 mg, 0.25 mmol). The reaction was allowed to stir for 10 minutes and then 1-bromo-2-methoxyethane (16 uL, 0.18 mmol) was added. The reaction was allowed to stir for 30 minutes and then quenched with aq. 1N HCl until slightly acidic. It was then diluted with Methanol and purified using gradient elution on reverse phase (30×150 mm (5 um) Sunfire Prep C18; 25-75% $CH_3CN$/water w/0.1% TFA modifier over 18 min) to provide the title compound. $^1$H NMR (400 MHz, DMSO-$d_6$): δ 12.04 (s, 1 H); 8.62 (s, 1 H); 7.41 (dd, J=8.6, 5.5 Hz, 2 H); 7.18 (t, J=8.9 Hz, 2 H); 4.47 (s, 2 H); 3.66-3.41 (m, 4 H); 3.20-3.13 (m, 1 H); 3.11 (s, 3H); 2.89-2.81 (m, 1H); 1.72 (s, 3H); 1.41 (s, 3H); 1.21 (t, J=7.1 Hz, 3H). LCMS anal. calcd. for $C_{23}H_{26}FN_5O_4S$: 487.2. Found: 488.2 (M+1)$^+$ The following compounds of the present invention were prepared using the method described in the Example above using the appropriate reactants and reagents.

| No. | Structure | Exact Mass [M + H]+ |
|---|---|---|
| 169 | 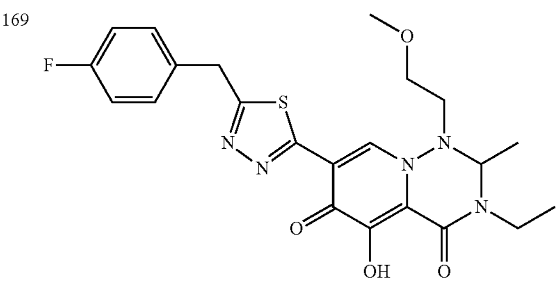 | 474 |
| 171 | 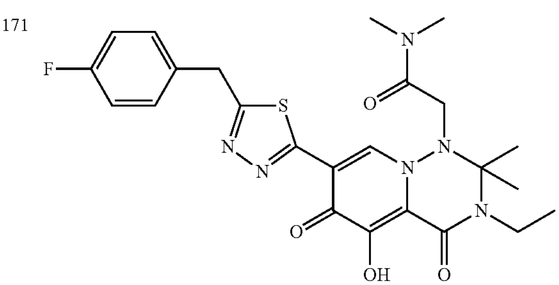 | 515 |

| No. | Structure | Exact Mass [M + H]+ |
|---|---|---|
| 172 | 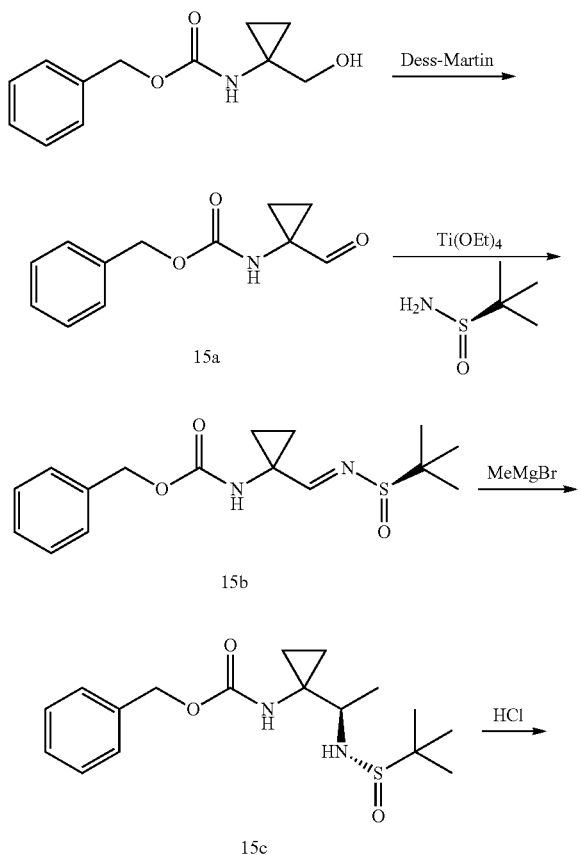 | 472 |
| 173 | 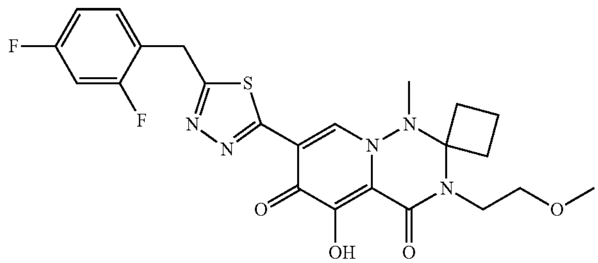 [SMILES: COCCN1C(=O)c2c(O)c(=O)c(-c3nnc(Cc4ccc(F)cc4F)s3)cn2N(C)C12CCC2] | — |

Example 15

Preparation of Intermediate Compound 15f

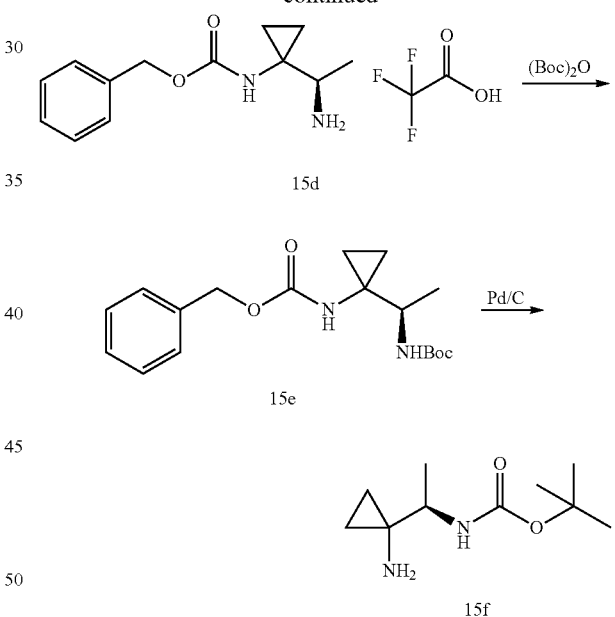

Step A—Synthesis of Intermediate Compound 15a

To a stirred solution of benzyl (1-(hydroxymethyl)cyclopropyl)carbamate (5.0 g, 22.60 mmol) in 200 mL of DCM was added Dess-Martin periodinane (11.50 g, 27.1 mmol). The mixture was allowed to stir at room temperature for 1 hour. It was diluted with 200 mL of DCM and 200 mL of $Na_2CO_3$ (aq). The organic was separated and dried over $Na_2SO_4$. It was concentrated and the resulting residue was purified using a silica-gel column eluting with 30% EtOAc/hexane to provide intermediate compound 15a as a white solid. $^1H$ NMR (400 MHz, $CDCl_3$): δ 9.18 (s, 1H), 7.26-7.28 (m, 5H), 5.55 (br, 1H), 5.08 (s, 2H), 1.58 (m, 2H), 1.39 (m, 2H). LCMS (M+H)=220.0.

Step B—Synthesis of Intermediate Compound 15b

To a stirred solution of intermediate compound 15a (2 g, 9.12 mmol) in 40 mL of THF at room temperature, was added (R)-2-methylpropane-2-sulfinamide (1.327 g, 10.95 mmol) and tetraethoxytitanium (4.16 g, 18.25 mmol). After stirred at room temperature for 8 h, the reaction mixture was added brine, the precipitate was filtered off, the filter cake was washed with EtOAc. The organic layer from the combined filtrate was separated, dried and concentrated in vacuo. The crude oil residue was purified using a silica gel column eluting with 20% EtOAc/DCM to provide intermediate compound 15b as a colorless oil. $^1$H NMR (400 MHz, CDCl$_3$): δ 7.26-7.28 (m, 5H), 5.59 (br, 1H), 5.55 (s, 2H), 1.52 (m, 2H), 1.40 (m, 2H), 1.18 (s, 9H). LCMS (M+H) =323.09.

Step C—Synthesis of Intermediate Compound 15c

To a stirred solution of intermediate compound 15b (2.9 g, 8.99 mmol) in 100 mL of DCM at 0° C. was added methylmagnesium bromide (3 M in Et$_2$O) (8.99 ml, 27.0 mmol). After stirred at 0° C. for 30 min., it was diluted with 200 mL of DCM. The organic was washed with NH$_4$Cl, brine, dried and then concentrated in vacuo. The residue oil was purified using a silica gel column (120 g) eluting with 10% MeOH/DCM to provide intermediate compound 15c as a colorless gel. LCMS (M+H)=339.09.

Step D—Synthesis of Intermediate 15d

To a solution of intermediate compound 15c in 80 mL of MeOH was added 4 N hydrogen chloride in dioxane (6.43 ml, 25.7 mmol). After stirred at room temperature for 1 hour, it was concentrated in vacuo. The residue was added 3 mL DMSO and purified using a C18 reverse phase column (120 mg, 12 run lengths, 5% ACN/H$_2$O-100% ACN/H$_2$O with 0.1% TFA) to provide intermediate compound 15d as a colorless gel. $^1$H NMR (CD$_3$OD, 400 MHz): δ 7.29-7.38 (m, 5H), 5.13 (d, J=5.6 Hz, 1H), 5.06 (d, J=5.6 Hz, 1H), 2.86 (m, 1H), 1.36 (d, J=5.2 Hz, 3H), 1.08 (m, 1H), 1.00 (m, 1H), 0.90 (m, 1H), 0.88 (m, 1H). LCMS (M+H)=235.14.

Step E—Synthesis of Intermediate 15e

To a stirred solution of intermediate compound 15d (1.9 g, 5.45 mmol) in 50 mL of DCM, was added di-tert-butyl dicarbonate (1.016 g, 4.66 mmol) and triethylamine (1.656 g, 16.36 mmol). The mixture was allowed to stir at room temperature overnight. At completion, it was diluted with 150 mL of DCM and 200 mL of 0.5 N HCl (aq.). The organic was separated, dried over Na$_2$SO$_4$ and concentrated in vacuo. The residue was purified using a silica gel column (120 g) eluting with 30% EtOAc/hexane to provide intermediate compound 15e as a white solid. $^1$H NMR (400 MHz, CDCl$_3$): δ 7.33-7.40 (m, 5H), 5.94 (br, 1H), 5.25 (br, 1H), 5.13 (d, J=9.6 Hz, 1H), 5.08 (d, J=9.6 Hz, 1H), 3.20 (m, 1H), 1.47 (s, 9H), 1.23 (d, J=4.4 Hz, 3H), 0.99 (m, 1H), 0.93 (m, 1H), 0.83 (m, 1H), 0.76 (m, 1H). LCMS (M+H)=335.19.

Step F—Synthesis of Intermediate 15f

To a suspension of intermediate compound 15e (1.5 g, 4.49 mmol) in 50 mL of MeOH was added 10% wt. palladium on Carbon (477 mg, 0.449 mmol). The reaction mixture was allowed to stir at room temperature under a balloon of H$_2$ overnight. The reaction mixture was filtered and the solvents was removed in vacuo to provide intermediate compound 15f as a white solid. $^1$H NMR (400 MHz, CDCl$_3$): δ 4.83 (br, 1H), 3.23 (br, 1H), 1.47 (s, 9H), 1.70 (d, J=5.6 Hz, 3H), 0.71-0.75 (m, 1H), 0.53-0.60 (m, 2H), 0.48-0.52 (m, 1H). LCMS (M+H)=201.18.

Example 16

Preparation of Intermediate Compound 16e

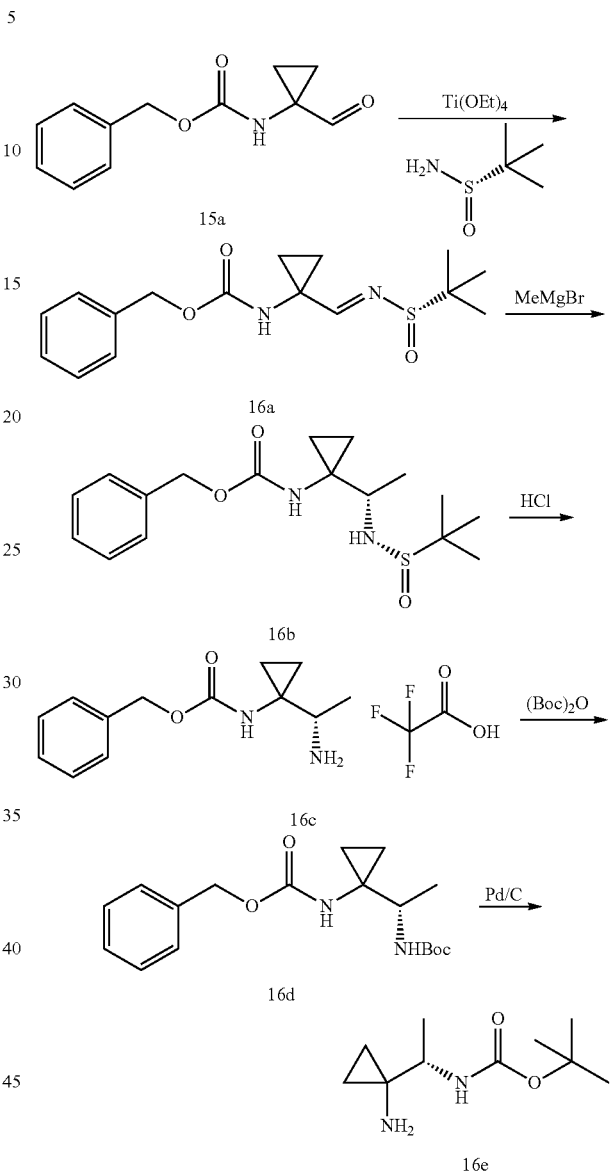

Step A—Synthesis of Intermediate Compound 2c

To a stirred solution of intermediate compound 15a (2 g, 9.12 mmol) in 40 mL of THF at room temperature, was added (S)-2-methylpropane-2-sulfinamide (1.327 g, 10.95 mmol) and tetraethoxytitanium (4.16 g, 18.25 mmol). After stirred at room temperature for 8 h, the reaction mixture was added brine, the precipitate was filtered off, the filter cake was washed with EtOAc. The organic layer from the combined filtrate was separated, dried and concentrated in vacuo. The crude oil residue was purified using a silica gel column eluting with 20% EtOAc/DCM to provide intermediate compound 16a as a colorless oil. $^1$H NMR (400 MHz, CDCl$_3$): δ 7.30-7.36 (m, 5H), 5.66 (br, 1H), 5.13 (d, J=9.6 Hz, 1H), 5.10 (d, J=9.6 Hz, 1H), 1.46 (m, 2H), 1.42 (m, 2H), 1.26 (s, 9 H). LCMS (M+H)=323.09.

Step C—Synthesis of Intermediate Compound 16b

To a stirred solution of intermediate compound 16a (2.88 g, 8.93 mmol) in 100 mL of DCM at 0° C., was added methylmagnesium bromide (3 M in Et₂O) (8.99 ml, 27.0 mmol). After stirred at 0° C. for 30 min., it was diluted with 200 mL of DCM. The organic was washed with NH₄Cl, brine, dried and then concentrated in vacuo. The residue oil was purified using a silica gel column (120 g) eluting with 10% MeOH/DCM to provide intermediate compound 16b as a colorless gel. LCMS (M+H)=339.09.

Step D—Synthesis of Intermediate 16c

To a solution of intermediate compound 16b in 80 mL of MeOH was added 4 N hydrogen chloride in dioxane (6.43 ml, 25.7 mmol). After stirred at room temperature for 1 hour, it was concentrated in vacuo. The residue was added 3 mL DMSO and purified using a C18 reverse phase column (120 g, 12 run lengths, 5% ACN/H₂O-100% ACN/H₂O with 0.1% TFA) to provide intermediate compound 16c as a colorless gel. ¹H NMR (CD₃OD, 400 MHz): δ 7.29-7.36 (m, 5H), 5.13 (d, J=9.6 Hz, 1H), 5.06 (d, J=9.6 Hz, 1H), 2.89 (m, 1H), 1.36 (d, J=5.2 Hz 3H), 1.08 (m, 1H), 0.99 (m, 1H), 0.90 (m, 1H), 0.88 (m, 1H). LCMS (M+H)=235.14.

Step E—Synthesis of Intermediate 16d

To a stirred solution of intermediate compound 16c (2.0 g, 5.74 mmol) in 50 mL of DCM, was added di-tert-butyl dicarbonate (1.069 g, 4.90 mmol)) and triethylamine (1.743 g, 17.23 mmol). The mixture was allowed to stir at room temperature overnight. At completion, it was diluted with 150 mL of DCM and 200 mL of 0.5 N HCl (aq.). The organic was separated, dried over anhydrous Na₂SO₄ and concentrated in vacuo. The residue was purified using a silica gel column (120 g) eluting with 30% EtOAc/hexane to provide intermediate compound 16d as a white solid. ¹H NMR (400 MHz, CDCl₃): δ 7.34-7.40 (m, 5H), 5.94 (br, 1H), 5.21 (br, 1H), 5.13 (d, J=9.6 Hz, 1H), 5.08 (d, J=9.6 Hz, 1H), 3.20 (m, 1H), 1.47 (s, 9H), 1.20 (d, J=5.6 Hz 3H), 0.98-1.02 (m, 1H), 0.84-0.94 (m, 1H), 0.80-0.83 (m, 1H), 0.75-0.79 (m, 1H). LCMS (M+H)=335.19.

Step F—Synthesis of Intermediate 16e

To a suspension of intermediate compound 16d (1.5 g, 4.49 mmol) in 50 mL of MeOH was added 10% wt. palladium on carbon (541 mg, 0.508 mmol). The reaction mixture was allowed to stir at room temperature under a hydrogen balloon overnight. The reaction mixture was filtered and the solvents removed in vacuo to provide intermediate compound 16e as a white solid. ¹H NMR (400 MHz, CDCl₃): δ 4.83 (br, 1H), 3.23 (br, 1H), 1.47 (s, 9H), 1.70 (d, J=5.6 Hz, 3H), 0.73-0.75 (m, 1H), 0.53-0.60 (m, 2H), 0.48-0.51 (m, 1H). LCMS (M+H)=201.18.

Example 17

Preparation of Compound 174

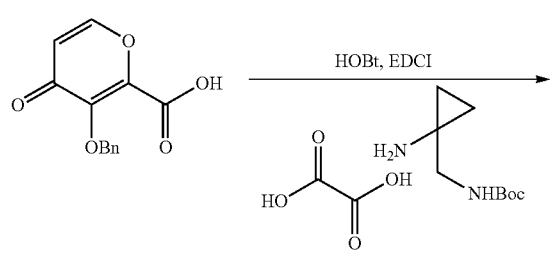

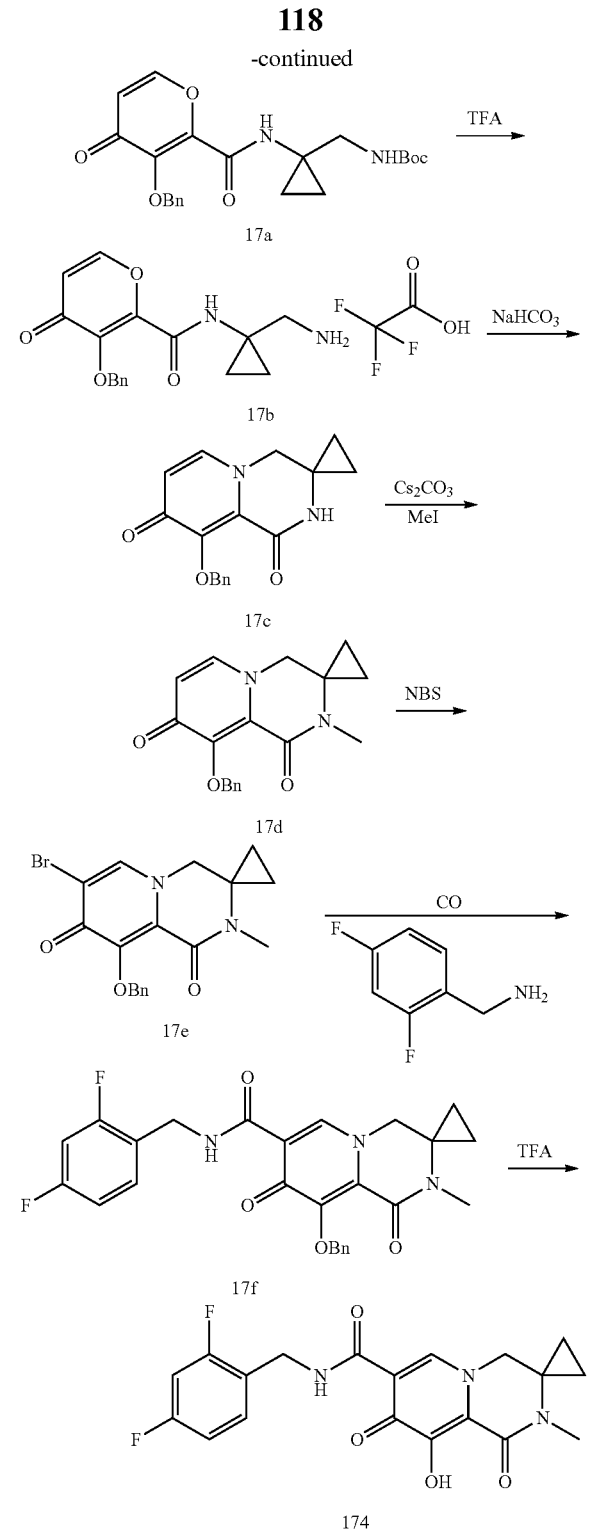

Step A—Synthesis of Intermediate Compound 17a

To a solution of 3-(benzyloxy)-4-oxo-4H-pyran-2-carboxylic acid (1100 mg, 3.98 mmol) in 20 mL of DCM, was added tert-butyl ((1-aminocyclopropyl)methyl)carbamate oxalate (1100 mg, 3.98 mmol), N1-((ethylimino)methylene)-N3,N3-dimethylpropane-1,3-diamine hydrochloride (1526 mg, 7.96 mmol), 1H-benzo[d][1,2,3]triazol-1-ol hydrate (122 mg, 0.796 mmol) and 4-methylmorpholine (2014 mg, 19.91 mmol) sequentially at room temperature.

The reaction mixture was allowed to stir at room temperature for 12 hours. At completion, the reaction solution was directly loaded on a silica gel column (120 g) eluting with 40% EtOAc/DCM to provide intermediate compound 17a as a white solid. $^1$H NMR (400 MHz, CDCl$_3$): δ 7.99 (br, 1H), 7.86 (d, J=4.4 Hz, 1H), 7.41-7.45 (m, 5H), 6.52 (d, J=4.4 Hz, 1H), 5.45 (s, 2H), 5.36 (br, 1H), 3.25 (d, J=3.6 Hz, 2H), 1.46 (s, 3H), 0.82 (m, 2H), 0.56 (m, 2H). LCMS (M+H)=415.12.

Step B—Synthesis of Intermediate Compound 17b

To a solution of intermediate compound 17a (2.5 g, 6.03 mmol) in 40 mL of DCM was added TFA (10.00 ml) and the reaction was allowed to stir at room temperature for 2 hours. The mixture was then concentrated in vacuo to provide intermediate compound 17b as a yellow oil. LCMS (M+H)=315.06.

Step C—Synthesis of Intermediate Compound 17c

A solution of intermediate compound 17b (1.80 g, 4.20 mmol) in sodium bicarbonate (sat. aq) (20 ml, 4.20 mmol) was heated at 90° C. for 3 hours. The solvent was removed in vacuo. To the resulting residue was added 2 mL of DCM and 2 mL of MeOH. The resulting mixturet was filtered. The filtrate was concentrated in vacuo. It was dissolved in 3 mL DMSO and the resulting solution was purified using a C18 reverse phase column (120 g, 12 run lengths, 5% ACN/H$_2$O-100% ACN/H$_2$O with 0.1% TFA) to provide intermediate compound 17c as a light yellow solid. $^1$H NMR (CD$_3$OD, 400 MHz): δ 7.64 (d, J=5.6 Hz, 1H), 7.46 (m, 2H), 7.27-7.30 (m, 3H), 6.54 (d, J=5.6 Hz, 1H), 5.23 (s, 2H), 4.10 (s, 2H), 0.89 (m, 2H), 0.87 (m, 2H). LCMS (M+H)=297.08.

Step D—Synthesis of Intermediate Compound 17d

A mixture of intermediate compound 17c (500 mg, 1.687 mmol), iodomethane (479 mg, 3.37 mmol) and Cs$_2$CO$_3$ (1649 mg, 5.06 mmol) in 5 mL of DMF was heated at 50° C. for 2 hours. At completion, it was cooled to room temperature and diluted with 0.5 mL of water. The mixture was loaded onto a C18 reverse phase column (40 g, 12 run lengths, 5% ACN/H$_2$O-100% ACN/H$_2$O with 0.1% TFA) to provide intermediate compound 17d as a light yellow solid. $^1$H NMR (400 MHz, CDCl$_3$): δ 7.85 (d, J=5.6 Hz, 1H), 7.58-7.62 (m, 2H), 7.32-7.42 (m, 5H), 5.26 (s, 2H), 4.22 (s, 2H), 2.98 (s, 3H), 1.05 (m, 2H), 0.99 (m, 2H). LCMS (M+H)=311.08.

Step E—Synthesis of Intermediate Compound 17e

To a solution of intermediate compound 17d (400 mg, 1.289 mmol) in 10 mL of DCM was added 1-bromopyrrolidine-2,5-dione (275 mg, 1.547 mmol). The reaction was allowed to stir at room temperature for 3 hours. The solvent was removed in vacuo. The residue was purified using a silica gel column eluting with 6% MeOH/DCM to provide intermediate compound 17e as a white solid. $^1$H NMR (400 MHz, CDCl$_3$): δ 7.65-7.67 (m, 2H), 7.62 (s, 1H), 7.28-7.36 (m, 3H), 5.35 (s, 2H), 3.89 (s, 2H), 2.94 (s, 3H), 1.20 (m, 2H), 0.92 (m, 2H). LCMS (M+H)=389.08.

Step F—Synthesis of Intermediate Compound 17f

A mixture of intermediate compound 17e (130 mg, 0.334 mmol), (2,4-difluorophenyl)methanamine (105 mg, 0.735 mmol), N-ethyl-N-isopropylpropan-2-amine (129 mg, 1.002 mmol) and Pd(tetrakis) (77 mg, 0.067 mmol) in 3 mL of DMSO was degassed and heated at 90° C. under a CO bolloon for 6 hours. After cooled to room temperature, the reaction mixture was purified using a C18 reverse phase column (40 g, 12 run lengths, 5% ACN/H$_2$O-100% ACN/H$_2$O with 0.1% TFA) to provide intermediate compound 17f contaminated with triphenylphosphine oxide. The mixture was moved to next step without further purification. LCMS (M+H)=480.25.

Step G—Synthesis of Compound 174

A solution of intermediate compound 17f (170 mg, 0436 mmol) in 3 mL of TFA was allowed to stir at room temperature for 2 hours. The solvent was removed in vacuo. The residue was dissolved in 5 mL of DMSO and purified using RP-HPLC. The product containing fractions was combined. The solvent was removed under a lyophilizer to provide compound 174 as a solid. $^1$H NMR (CD$_3$OD, 400 MHz): δ 8.35 (s, 1H), 7.41-7.46 (m, 1H), 6.92-6.99 (m, 2H), 4.63 (s, 2H), 4.31 (s, 2H), 2.97 (s, 3H), 1.34-1.39 (m, 2H), 1.03-1.34 (m, 2H). LCMS (M+H)=390.03.

Example 18

Preparation of Compound 175

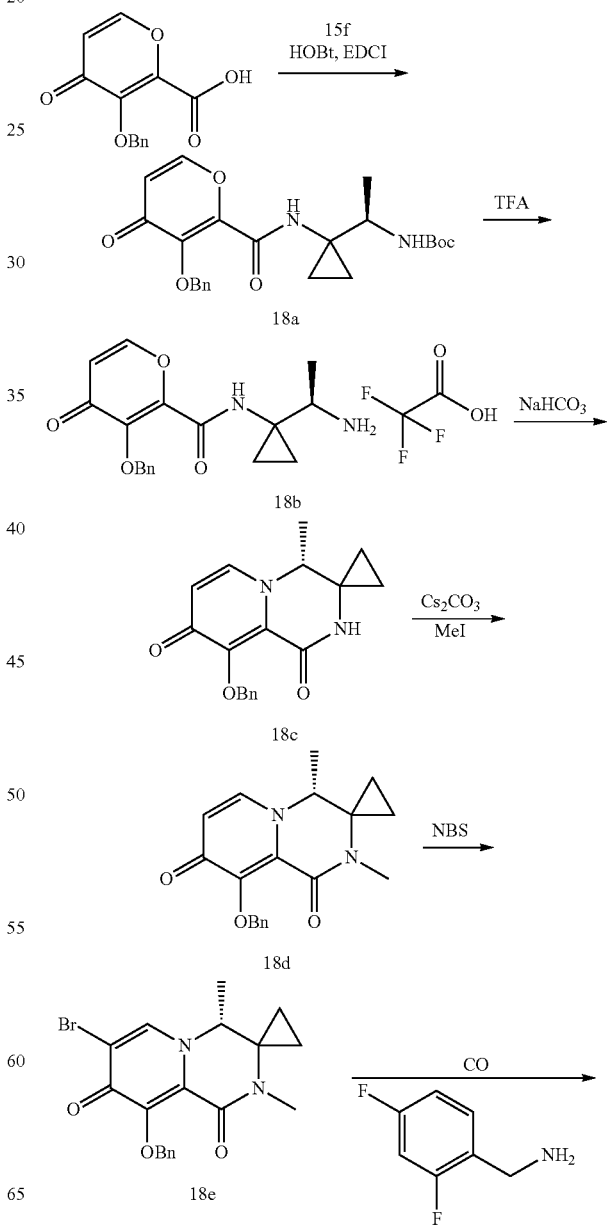

-continued

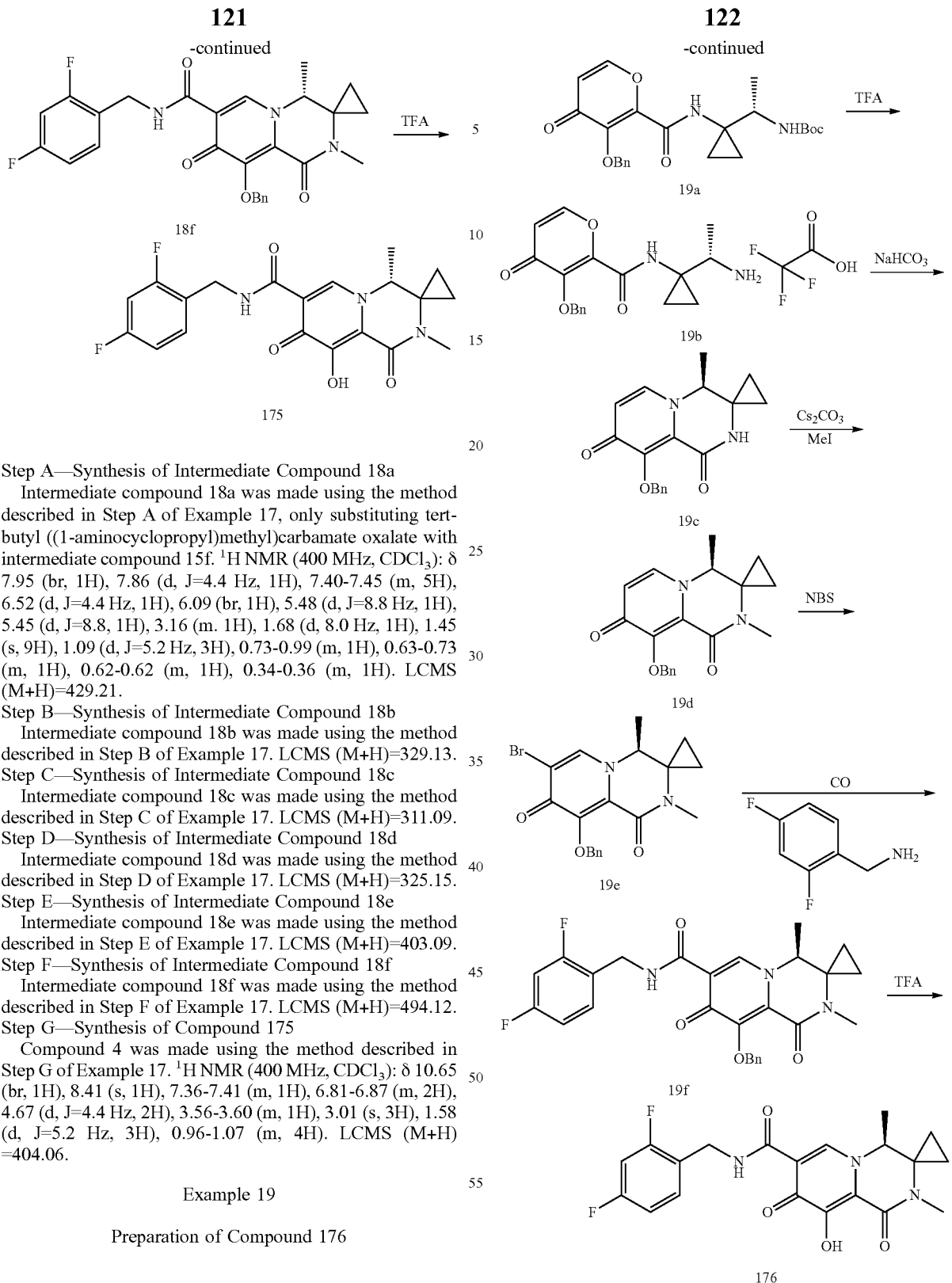

Step A—Synthesis of Intermediate Compound 18a

Intermediate compound 18a was made using the method described in Step A of Example 17, only substituting tert-butyl ((1-aminocyclopropyl)methyl)carbamate oxalate with intermediate compound 15f. $^1$H NMR (400 MHz, CDCl$_3$): δ 7.95 (br, 1H), 7.86 (d, J=4.4 Hz, 1H), 7.40-7.45 (m, 5H), 6.52 (d, J=4.4 Hz, 1H), 6.09 (br, 1H), 5.48 (d, J=8.8 Hz, 1H), 5.45 (d, J=8.8, 1H), 3.16 (m. 1H), 1.68 (d, 8.0 Hz, 1H), 1.45 (s, 9H), 1.09 (d, J=5.2 Hz, 3H), 0.73-0.99 (m, 1H), 0.63-0.73 (m, 1H), 0.62-0.62 (m, 1H), 0.34-0.36 (m, 1H). LCMS (M+H)=429.21.

Step B—Synthesis of Intermediate Compound 18b

Intermediate compound 18b was made using the method described in Step B of Example 17. LCMS (M+H)=329.13.

Step C—Synthesis of Intermediate Compound 18c

Intermediate compound 18c was made using the method described in Step C of Example 17. LCMS (M+H)=311.09.

Step D—Synthesis of Intermediate Compound 18d

Intermediate compound 18d was made using the method described in Step D of Example 17. LCMS (M+H)=325.15.

Step E—Synthesis of Intermediate Compound 18e

Intermediate compound 18e was made using the method described in Step E of Example 17. LCMS (M+H)=403.09.

Step F—Synthesis of Intermediate Compound 18f

Intermediate compound 18f was made using the method described in Step F of Example 17. LCMS (M+H)=494.12.

Step G—Synthesis of Compound 175

Compound 4 was made using the method described in Step G of Example 17. $^1$H NMR (400 MHz, CDCl$_3$): δ 10.65 (br, 1H), 8.41 (s, 1H), 7.36-7.41 (m, 1H), 6.81-6.87 (m, 2H), 4.67 (d, J=4.4 Hz, 2H), 3.56-3.60 (m, 1H), 3.01 (s, 3H), 1.58 (d, J=5.2 Hz, 3H), 0.96-1.07 (m, 4H). LCMS (M+H)=404.06.

Example 19

Preparation of Compound 176

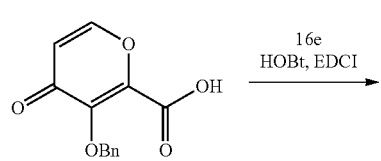

Step A—Synthesis of Intermediate Compound 19a

Intermediate compound 19a was made using the method described in Step A of Example 17, only substituting tert-butyl ((1-aminocyclopropyl)methyl)carbamate oxalate with intermediate compound 16e. LCMS (M+H)=429.21.

Step B—Synthesis of Intermediate Compound 19b

Intermediate compound 19b was made using the method described in Step B of Example 17. LCMS (M+H)=329.12.

Step C—Synthesis of Intermediate Compound 19c

Intermediate compound 19c was made using the method described in Step C of Example 17. LCMS (M+H)=311.10.

Step D—Synthesis of Intermediate Compound 19d

Intermediate compound 19d was made using the method described in Step D of Example 17. LCMS (M+H)=325.15.

Step E—Synthesis of Intermediate Compound 19e

Intermediate compound 19e was made using the method described in Step E of Example 17. LCMS (M+H)=403.09.

Step F—Synthesis of Intermediate Compound 19f

Intermediate compound 19f was made using the method described in Step F of Example 17. LCMS (M+H)=494.18.

Step G—Synthesis of Compound 176

Compound 176 was made using the method described in Step G of Example 17. $^1$H NMR (400 MHz, CDCl$_3$): δ 10.66 (br, 1H), 8.43 (s, 1H), 7.36-7.40 (m, 1H), 6.81-6.87 (m, 2H), 4.67 (d, J=4.4 Hz, 2H), 3.57-3.62 (m, 1H), 3.01 (s, 3H), 1.58 (d, J=5.2 Hz, 3H), 0.96-1.07 (m, 4H). LCMS (M+H)= 404.09.

The following compounds of the present invention were prepared using the method described in the Example above using the appropriate reactants and reagents.

| No. | Structure | Exact Mass [M + H]+ |
|---|---|---|
| 177 | 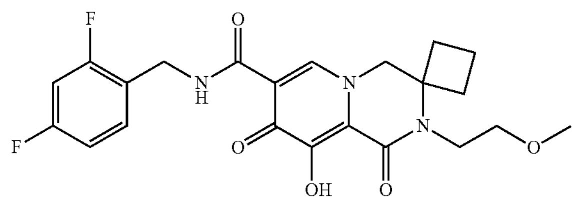 [SMILES: COCCN1C(=O)c2c(O)c(=O)c(C(=O)NCc3ccc(F)cc3F)cn2CC12CCC2] | 448 |
| 178 | 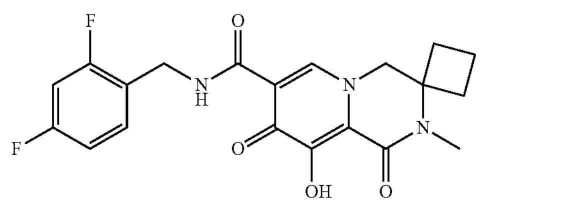 [SMILES: CN1C(=O)c2c(O)c(=O)c(C(=O)NCc3ccc(F)cc3F)cn2CC12CCC2] | 404 |
| 179 | 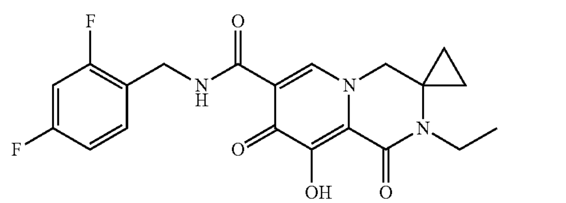 [SMILES: CCN1C(=O)c2c(O)c(=O)c(C(=O)NCc3ccc(F)cc3F)cn2CC12CC2] | 404 |
| 180 | 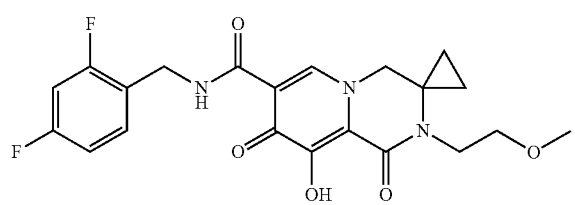 [SMILES: COCCN1C(=O)c2c(O)c(=O)c(C(=O)NCc3ccc(F)cc3F)cn2CC12CC2] | 434 |
| 181 | 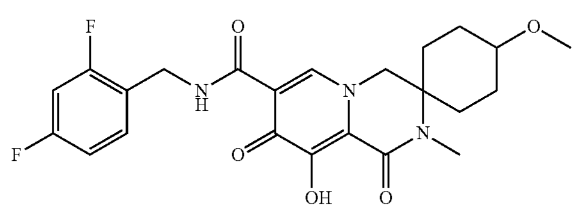 [SMILES: COC1CCC2(CC1)Cn1cc(C(=O)NCc3ccc(F)cc3F)c(=O)c(O)c1C(=O)N2C] | 462 |
| 182 | 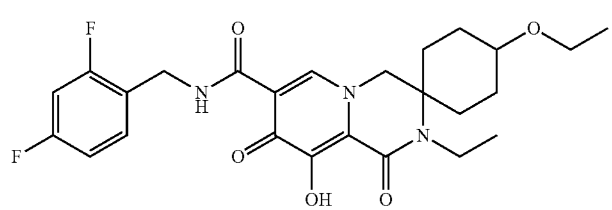 [SMILES: CCOC1CCC2(CC1)Cn1cc(C(=O)NCc3ccc(F)cc3F)c(=O)c(O)c1C(=O)N2CC] | 490 |

| No. | Structure | Exact Mass [M + H]+ |
|---|---|---|
| 183 | 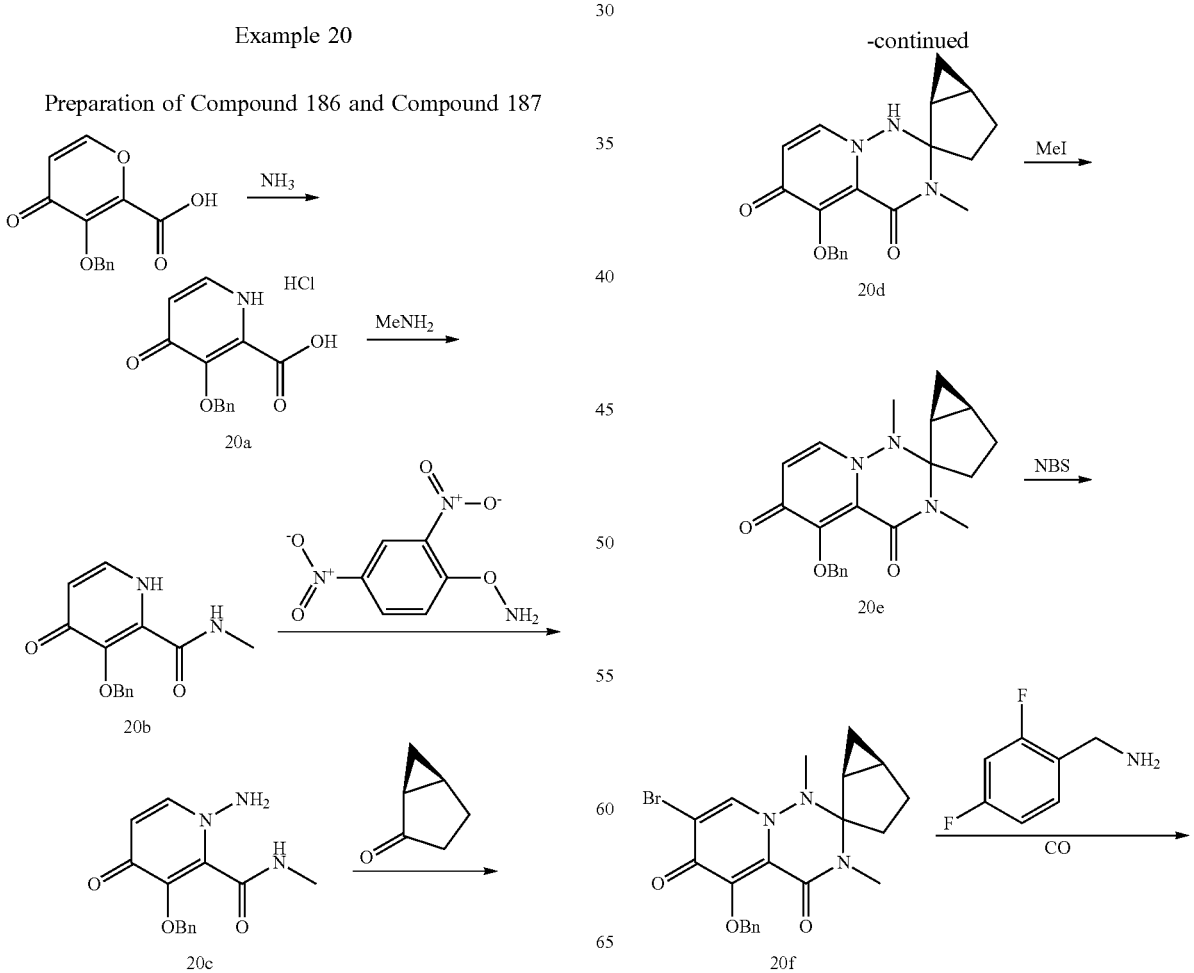 | 448 |
| 184 | 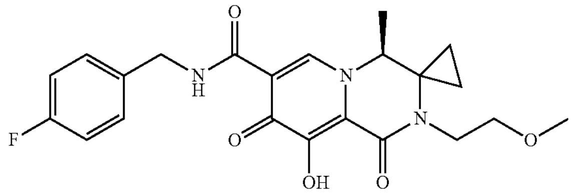 [SMILES: COCCN1C(=O)c2c(O)c(=O)c(C(=O)NCc3ccc(F)cc3)cn2[C@@H](C)C12CC2] | 430 |
| 185 | 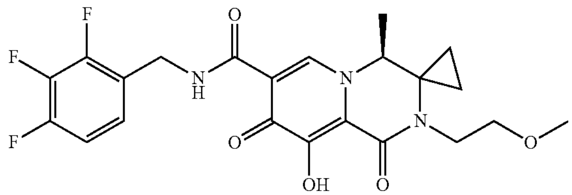 [SMILES: COCCN1C(=O)c2c(O)c(=O)c(C(=O)NCc3ccc(F)c(F)c3F)cn2[C@@H](C)C12CC2] | 466 |
Example 20
Preparation of Compound 186 and Compound 187

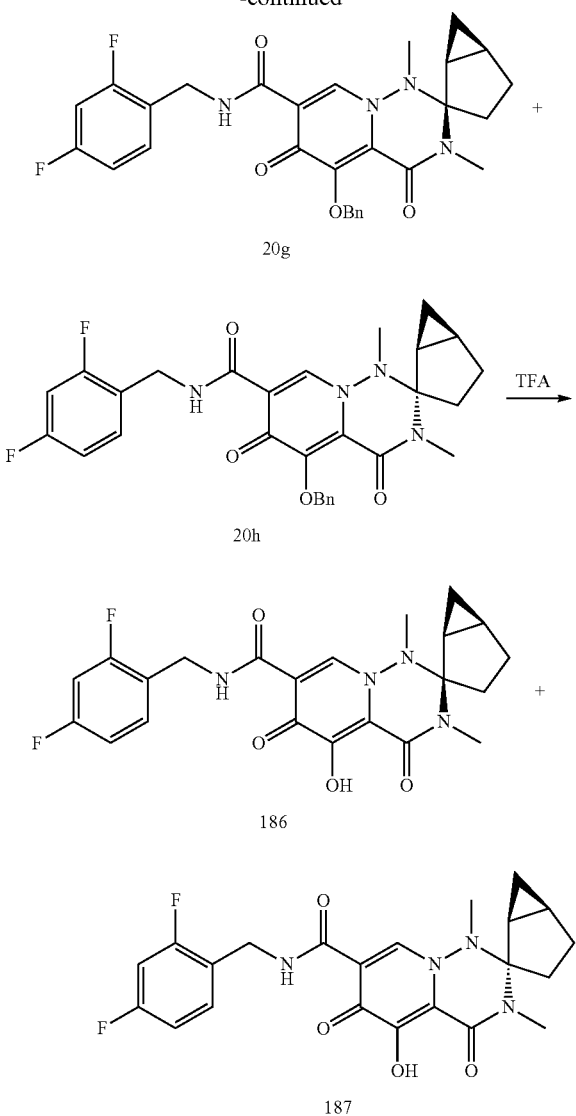

Step A—Synthesis of Intermediate Compound 20a

The intermediate compound 3-(benzyloxy)-4-oxo-4H-pyran-2-carboxylic acid (1800 mg, 7.31 mmol) was added ammonia in H$_2$O (2223 mg, 36.6 mmol). The mixture was allowed to stir at room temperature for overnight. At completion, it was concentrated in vacuo. To the resulting residue was added 10 mL of 2 N HCl (aq.). The solid preciptate was collected by filtration and washed with water to provide intermediate compound 20a as a white solid. LCMS (M+H)=246.08.

Step B—Synthesis of Intermediate Compound 20b

To a mixture of intermediate compound 20a (400 mg, 1.420 mmol), 1-(3-dimethylaminopropyl)-3-ethylcabodiimide (331 mg, 2.130 mmol) in 20 mL of DCM, was added 4-methylmorpholine (718 mg, 7.10 mmol) and 4-hydroxybenzotriazole (192 mg, 1.420 mmol). The reaction mixture was allowed to stir at room temperature overnight. The solvent was removed in vacuo. The residue was purified using a C18 reverse phase column (120 g, 12 run lengths, 5% ACN/H$_2$O-100% ACN/H$_2$O with 0.1% TFA) to provide intermediate compound 20b as a light yellow solid. LCMS (M+H)=259.05.

Step C—Synthesis of Intermediate Compound 20c

A mixture of intermediate compound 20b (320 mg, 1.058 mmol) and potassium carbonate (439 mg, 3.18 mmol) in 10 mL of DMF was allowed to stir at room temperature for 15 min. To the resulting mixture was added O-(2,4-dinitrophenyl)hydroxylamine (316 mg, 1.588 mmol). The mixture was allowed to stir at room temperature overnight. The resulting solution was purified using a C18 reverse phase column (120 mg, 12 run lengths, 5% ACN/H$_2$O-100% ACN/H$_2$O with 0.1% TFA) to provide intermediate compound 20c as a white solid. LCMS (M+H)=274.10.

Step D—Synthesis of Intermediate Compound 20d

A mixture of 20c (280 mg, 1.025 mmol), (1S,5R)-bicyclo[3.1.0]hexan-2-one (492 mg, 5.12 mmol) and p-toluenesulfonic acid monohydrate (97 mg, 0.512 mmol) was heated at 90° C. for 1 hour. The reaction mixture was cooled to room temperature and purified using a silica-gel column eluting with 6% MeOH/DCM to provide intermediate compound 20d as a white foam. LCMS (M+H)=352.22.

Step E—Synthesis of Intermediate Compound 20e

Intermediate compound 20e was made using the method described in Step D of Example 17. LCMS (M+H)=366.12.

Step F—Synthesis of Intermediate Compound 20f

Intermediate compound 18f was made using the method described in Step E of Example 17. LCMS (M+H)=444.06.

Step G—Synthesis of Intermediate Compound 20g, 20h

Racemic intermediate compound 20g+20h was made using the method described in Step F of Example 178. The product was further purified using a chiral IA column to provide 20g and 20h. LCMS (M+H)=535.17.

Step H—Synthesis of Compound 186 and Compound 187

Compound 186 was made using the method described in Step G of Example 17. $^1$H NMR (400 MHz, CDCl$_3$): δ 10.52 (br, 1H), 8.49 (s, 1H), 7.35-7.40 (m, 1H), 6.79-6.86 (m, 2H), 4.66 (m, 2H), 3.26 (s, 3H), 2.93 (s, 3H), 2.01-2.08 (m, 1H), 1.70-1.80 (m, 1H), 1.56-1.70 (m, 1H), 1.50-1.54 (m, 1H), 1.30-1.33 (m, 1H), 0.98-1.03 (m, 1H), 0.73-0.76 (s, 1H). LCMS (M+H)=445.26.

Compound 187 was made using the method described in Step G of Example 17. $^1$H NMR (400 MHz, CDCl$_3$): δ 10.56 (br, 1H), 8.55 (s, 1H), 7.35-7.41 (m, 1H), 6.80-6.89 (m, 2H), 4.66 (m, 2H), 3.33 (s, 3H), 2.95 (s, 3H), 2.03-1.99 (m, 1H), 1.89-1.94 (m, 1H), 1.74-1.83 (m, 1H), 1.65-1.69 (m, 1H), 1.60-1.61 (m, 1H), 0.90-0.95 (m, 1H), 0.81-0.83 (s, 1H). LCMS (M+H)=445.26.

The following compounds of the present invention were prepared using the method described in the Example above using the appropriate reactants and reagents.

| No. | Structure | Exact Mass [M + H]+ |
|---|---|---|
| 188 | 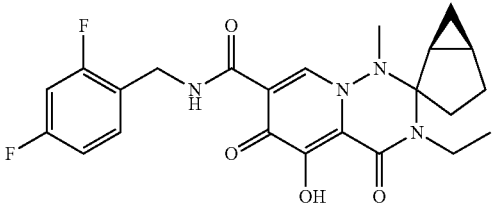 [SMILES: CCN1C(=O)c2c(O)c(=O)c(C(=O)NCc3ccc(F)cc3F)cn2N(C)C12CC[C@@H]1C[C@@H]12] | 459 |
| 189 | 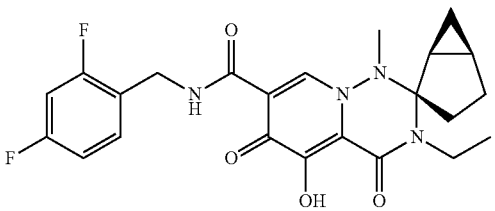 [SMILES: CCN1C(=O)c2c(O)c(=O)c(C(=O)NCc3ccc(F)cc3F)cn2N(C)[C@@]12CC[C@@H]1C[C@@H]12] | 459 |
| 190 | 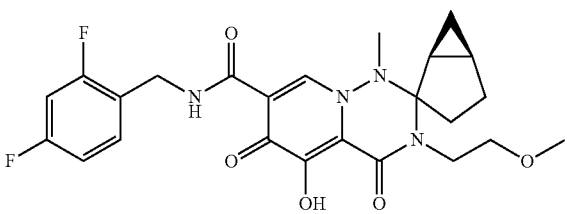 [SMILES: COCCN1C(=O)c2c(O)c(=O)c(C(=O)NCc3ccc(F)cc3F)cn2N(C)C12CC[C@@H]1C[C@@H]12] | 489 |
| 191 | 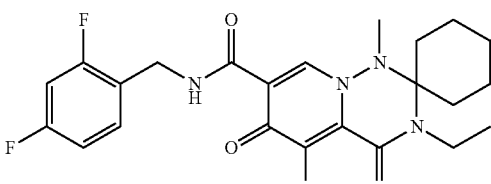 | 505 |
| 192 | 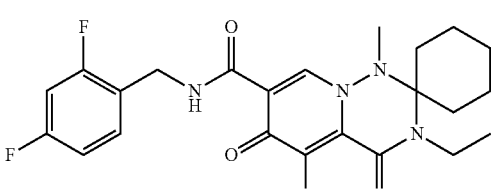 | 505 |
| 193 | 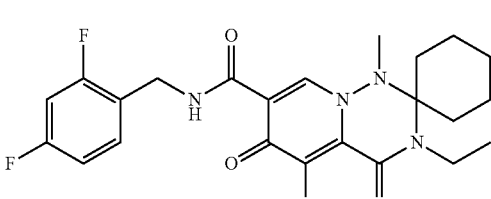 | 519 |
| 194 | 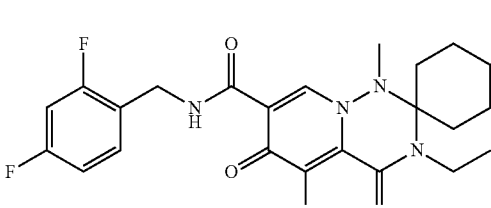 | 519 |

Example 21
Preparation of Compound 195
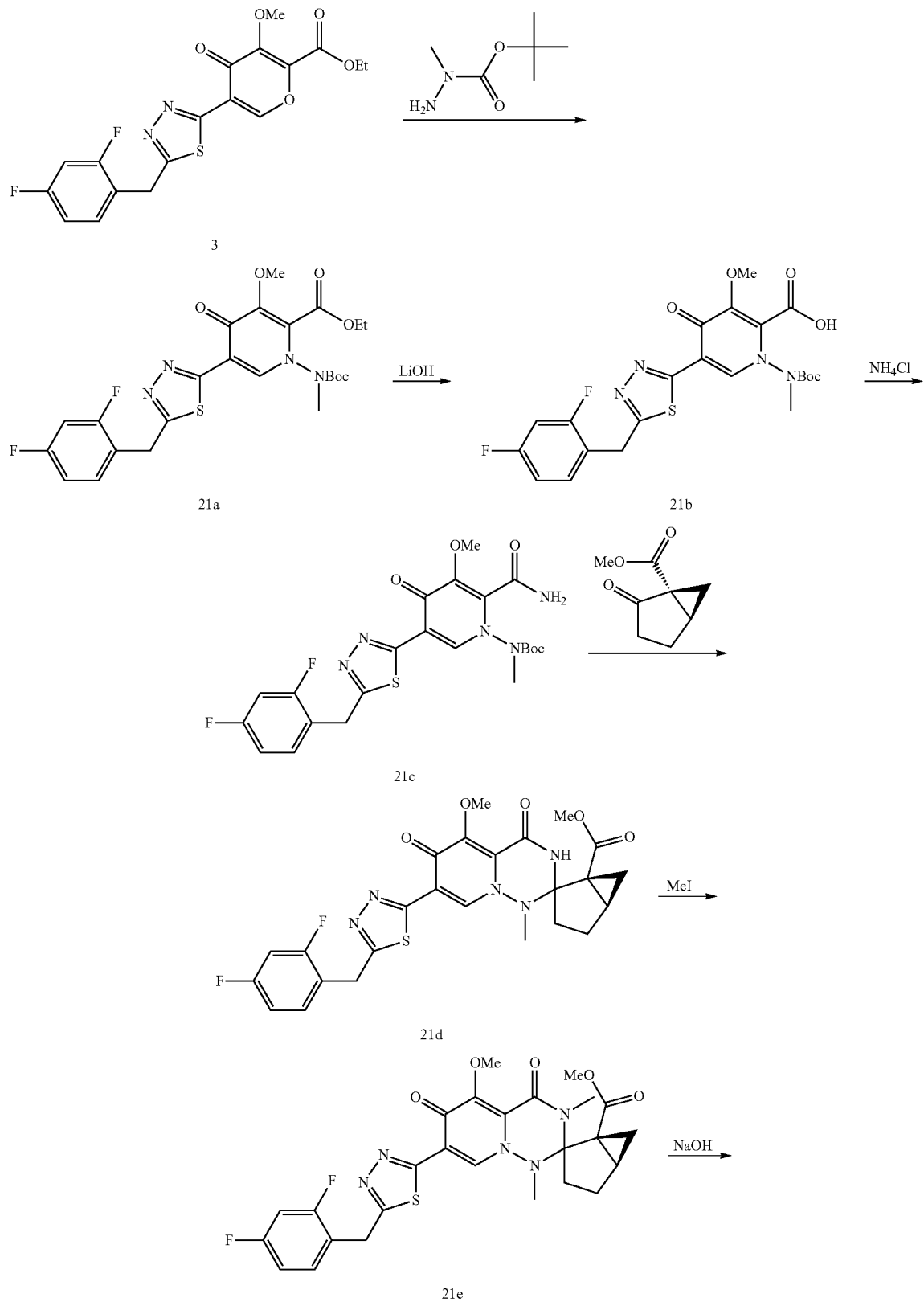

-continued

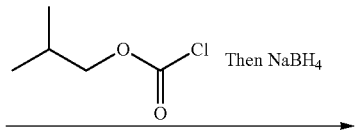
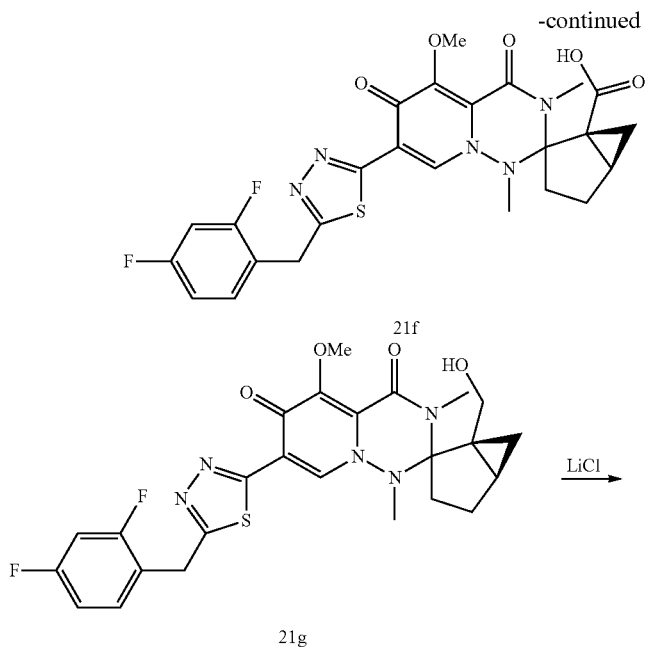
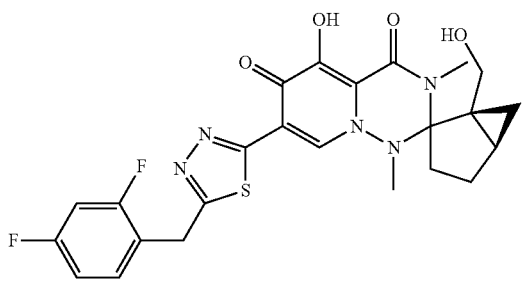

Step A—Synthesis of Intermediate Compound 21a

To a solution of 3 (2000 mg, 4.13 mmol) in 1-methylimidazole (20 ml) was added tert-butyl 1-methylhydrazinecarboxylate (603 mg, 4.13 mmol). The reaction mixture was allowed to stir at 60° C. for 5 hours. At completion, it was cooled to room temperature and diluted with 200 mL of 80% EtOAc/hexane. It was washed with water (2×150 mL) and brine. The organic layer was dried over anhydrous $Na_2SO_4$. After filtration, the filtrate was concentrated in vacuo. The residue was purification by a silica gel column (220 g) eluting with 50% EtOAc/hexane to provideed 21a as a yellow oil. LCMS (M+H)=537.20.

Step B—Synthesis of Intermediate Compound 21b

The compound 21a (2100 mg, 3.43 mmol) in 10 mL of EtOH was treated at room temperature with aqueous 2 M lithium hydroxide solution (4.28 ml, 8.57 mmol). The reaction was allowed to stir at 45° C. for 20 hours. At completion, the reaction was poured into water. The pH was adjusted to 3-4 with aq 2 M $NaHSO_4$ (aq.). The aqueous was extracted with EtOAc. The combined organic layers were washed with brine, dried over anhydrous $Na_2SO_4$, and then concentrated in vacuo. The residue was purified using a C18 reverse phase column (120 g, 12 run lengths, 5% ACN/$H_2O$-100% ACN/$H_2O$ with 0.1% TFA) to provide 21b as a solid. LCMS (M+H)=509.09.

Step C—Synthesis of Intermediate Compound 21c

To a solution of 21b (1200 mg, 2.053 mmol) in DMF (10 ml), was added ((6-chloro-1H-benzo[d][1,2,3]triazol-1-yl)oxy)tri(pyrrolidin-1-yl)phosphonium hexafluorophosphate (V) (1139 mg, 2.053 mmol) and N-ethyl-N-isopropylpropan-2-amine (1326 mg, 10.26 mmol), followed by ammonium chloride (329 mg, 6.16 mmol). The reaction was allowed to stir at room temperature overnight. To the content was added 10 mL of 2 N HCl (aq.), followed by 120 mL of water. The mother liquor was extracted with 100 mL of EtOAc. The organic was concentrated in vacuo. The residue was purified using a C18 column (120 g) eluting with 0.05% TFA in water/0.05% TFA in ACN (from 10% to 90% over 15 column volume) to provide 21c as a solid. LCMS (M+H)=508.05.

Step D—Synthesis of Intermediate Compound 21d

The mixture of 21c (600 mg, 1.241 mmol), 4-methylbenzenesulfonic acid hydrate (70.8 mg, 0.372 mmol) and (1R, 5R)-methyl 2-oxobicyclo[3.1.0]hexane-1-carboxylate (957 mg, 6.20 mmol) in 6 mL of 1,2-dichloroethane was heated at 90° C. for 1 hour. Additional 0.3 equivalent 4-methylbenzenesulfonic acid hydrate was added. The mixture was then stirred for 30 min more. This process of adding 4-methylbenzenesulfonic acid hydrate and stirring was repeated one more time. The reaction mixture was cooled down and purified using a silica-gel column eluting with 7% MeOH/DCM to provide 21d as a solid. LCMS (M+H)=544.17.

Step E—Synthesis of Intermediate Compound 21e

The mixture of 21d (290 mg, 0.468 mmol), iodomethane (133 mg, 0.936 mmol) and cesium carbonate (457 mg, 1.404 mmol) in 5 mL of DMF was allowed to stir at room temperature for 1.5 hours. The resulting mixture was filtered. The filtrate was directly purified using a C18 reverse phase column (120 g, 12 run lengths, 5% ACN/$H_2O$-100% ACN/$H_2O$ with 0.1% TFA) to provide 21e as a solid. LCMS (M+H)=558.27.

Step F—Synthesis of Intermediate Compound 21f

The solution of 21e (450 mg, 0.807 mmol) in MeOH (8.0 ml) was added 2 N NaOH (aq.) (4.04 ml, 8.07 mmol). The mixture was allowed to stir at 60° C. overnight. At completion, it was concentrated to remove most of MeOH. To the resulting residue was added 100 mL of EtOAc and 100 mL of 2 N HCl. The organic was separated, dried over anhydrous $Na_2SO_4$ and then concentrated in vacuo. The residue was purified using a C18 reverse phase column (120 mg, 12 run lengths, 5% ACN/$H_2O$-100% ACN/$H_2O$ with 0.1% TFA) to provide 21f as a solid. LCMS (M+H)=544.20.

Step G—Synthesis of Intermediate Compound 21g

A solution of 21f (400 mg, 0.736 mmol) in 7 mL of THF at 0° C. was added triethylamine (298 mg, 2.94 mmol), followed by adding isobutyl chloroformate (251 mg, 1.840 mmol). The mixture was allowed to stir at this temperature for 15 min. At completion, it was filtered. The solid cake was washed with 5 mL of THF. The combined organic was then cooled to −78° C. and sodium borohydride (52.7 mg, 1.472 mmol) was added. To the mixture was added 1 mL MeOH. The reaction was slowly warmed up to 0° C. and stirred for 15 min. It was diluted with 50 mL of DCM and 20 mL of 1.2 N HCl aqueous solution. The organic was separated, dried over anhydrous Na$_2$SO$_4$ and concentrated in vacuo. The residue was purified using a silica gel column (120 g) eluting with 7% MeOH/DCM to provide 21g as a solid. LCMS (M+H)=530.16.

Step H—Synthesis of Compound 195

To a solution of 21g (120 mg, 0.227 mmol) in 3 mL of DMF was added lithium chloride (192 mg, 4.53 mmol). The mixture was allowed to stir at 100° C. for 1 hour. It was cooled down and added 0.4 mL of H$_2$O. The resulting solution was purified using a C18 reverse phase column (120 g, 12 run lengths, 5% ACN/H$_2$O-100% ACN/H$_2$O with 0.1% TFA) to provide 195 as a solid that was a single racemate. $^1$H NMR (CDCl$_3$, 400 MHz) δ 8.79 (s, 1H), 7.36-7.40 (m, 1H), 6.90-6.93 (m, 2H), 4.75 (s, 2H), 4.47 (s, 2H), 3.32 (m, 2H), 3.20 (s, 3H), 3.03 (m, 2H), 2.86 (s, 3H), 2.26-2.32 (m, 1H), 2.13-2.18 (m, 1H), 1.94-2.03 (m, 2H), 1.64-1.68 (m, 1H), 0.92-0.94 (m, 1H), 0.78-0.81 (m, 1H). LCMS (M+H)=516.17.

Example 22

Preparation of Compound 196

Step B—Synthesis of Compound 196

To a solution of 22a (13 mg, 0.023 mmol) in 1 mL of DCM was added 0.5 mL of TFA. The reaction was allowed to stir at room temperature for 1 hour. The solvent was removed in vacuo. The residue was purified using RP-HPLC to provide compound 196 (9 mg, 0.015 mmol, 66.4% yield) as a white solid. $^1$H NMR (CDCl$_3$, 400 MHz) δ 8.90 (s, 1H), 7.31-7.51 (m, 1H), 6.86-6.90 (m, 2H), 4.52 (s, 2H), 3.04 (s, 3H), 1.94-2.15 (m, 2H), 1.63-1.89 (m, 2H), 1.28-1.48 (m, 2H), 0.68-0.91 (m, 2H). LCMS (M+H)=472.11.

Example 23

Preparation of Compound 197 and Compound 198

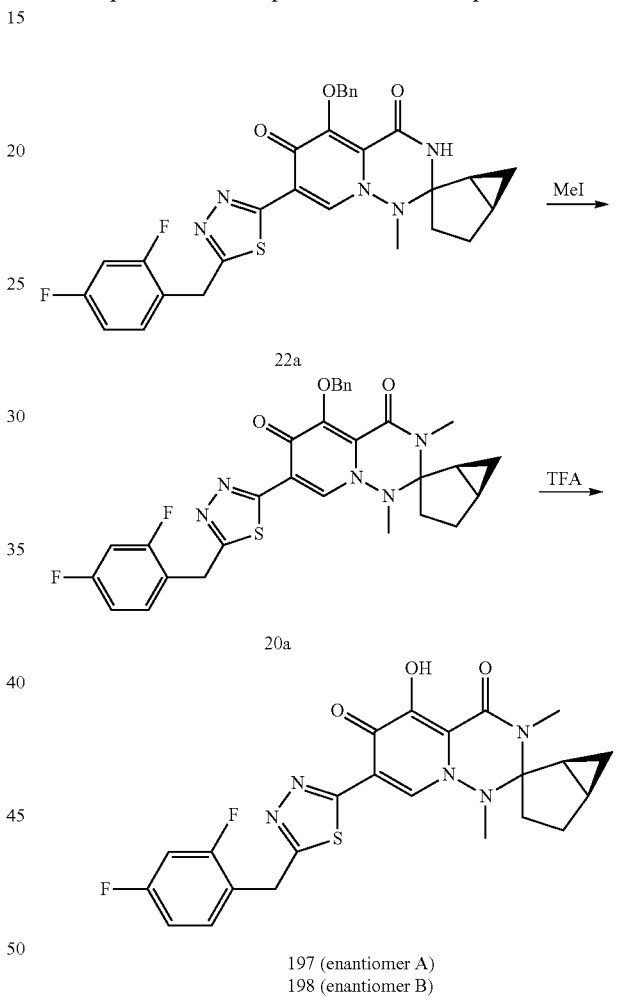

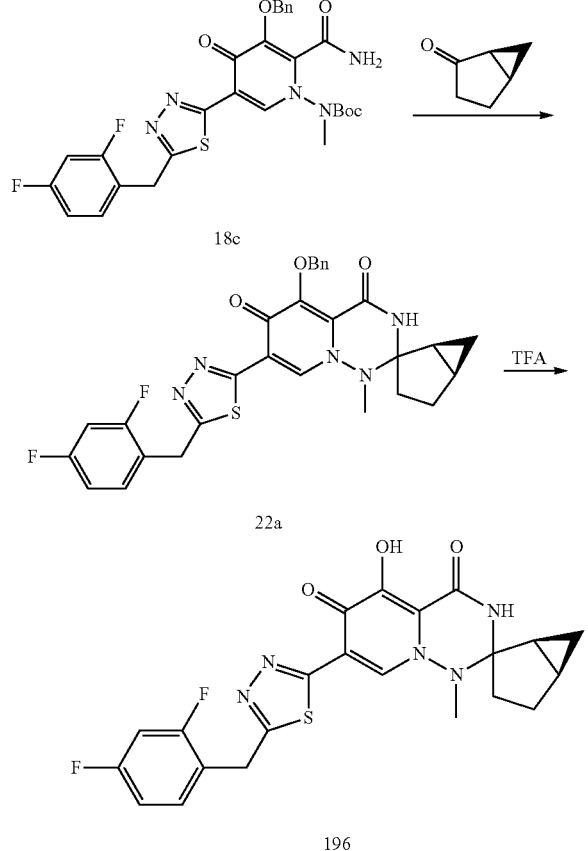

Step A—Synthesis of Intermediate Compound 22a

The compound 22a was made using the method described in Step D of Example 21. LCMS (M+H)=562.20.

Step A—Synthesis of Intermediate Compound 23a

To a stirred solution of intermediate compound 22a (200 mg, 0.356 mmol) in 3 mL of DMF was added iodomethane (111 mg, 0.783 mmol) and cesium carbonate (348 mg, 1.068 mmol)). The resulting mixture was then stirred at this temperature for 30 min. It was filtered and the filtrate was purified using a C18 reverse phase column (120 g, 12 run lengths, 5% ACN/H$_2$O-100% ACN/H$_2$O with 0.1% TFA) to provide intermediate compound 23a as a white solid compound. LCMS (M+H)=576.39.

Step B—Synthesis of Compound 197 and Compound 198

The compounds 197 and 198 was made using the method described in Step B of Example 22. The compound was separated by chiral AS column to provide two diasteromers 197 and 198. Compound 197: ¹H NMR (CDCl₃, 400 MHz) δ 8.79 (s, 1H), 7.29-7.34 (m, 1H), 6.86-6.89 (m, 2H), 4.50 (s, 2H), 3.34 (s, 3H), 2.99 (s, 3H), 1.99-2.19 (m, 3H), 1.88-1.95 (m, 1H), 1.81-1.87 (m, 1H), 1.72-1.76 (m, 1H), 1.60-1.63 (m, 1H), 0.92-0.97 (m, 1H), 0.82-0.85 (m, 1H). LCMS (M+H)=486.09. Compound 198: ¹H NMR (CDCl₃, 400 MHz)) 8.77 (s, 1H), 7.29-7.35 (m, 1H), 6.85-6.89 (m, 2H), 4.50 (s, 2H), 3.29 (s, 3H), 2.99 (s, 3H), 2.06-2.13 (m, 1H), 1.80-1.84 (m, 1H), 1.70-1.75 (m, 1H), 1.60-1.65 (m, 1H), 1.55-1.57 (m, 1H), 1.27-1.36 (m, 1H), 1.01-1.05 (m, 1H), 0.76-0.79 (m, 1H). LCMS (M+H)=486.10.

The following compounds of the present invention were prepared using the method described in the Example above using the appropriate reactants and reagents.

| No. | Structure | Exact Mass [M + H]+ |
|---|---|---|
| 199 | (mixture of diastereomers) | 544 |
| 200 | (mixture of diastereomers) | 516 |
| 201 | (mixture of diastereomers) | 472 |
| 202 | (mixture of diastereomers) | 530 |

| No. | Structure | Exact Mass [M + H]+ |
|---|---|---|
| 203 | (mixture of diastereomers) | 530 |
| 204 | (mixture of diastereomers) | 530 |

Example 24

Preparation of Compound 205

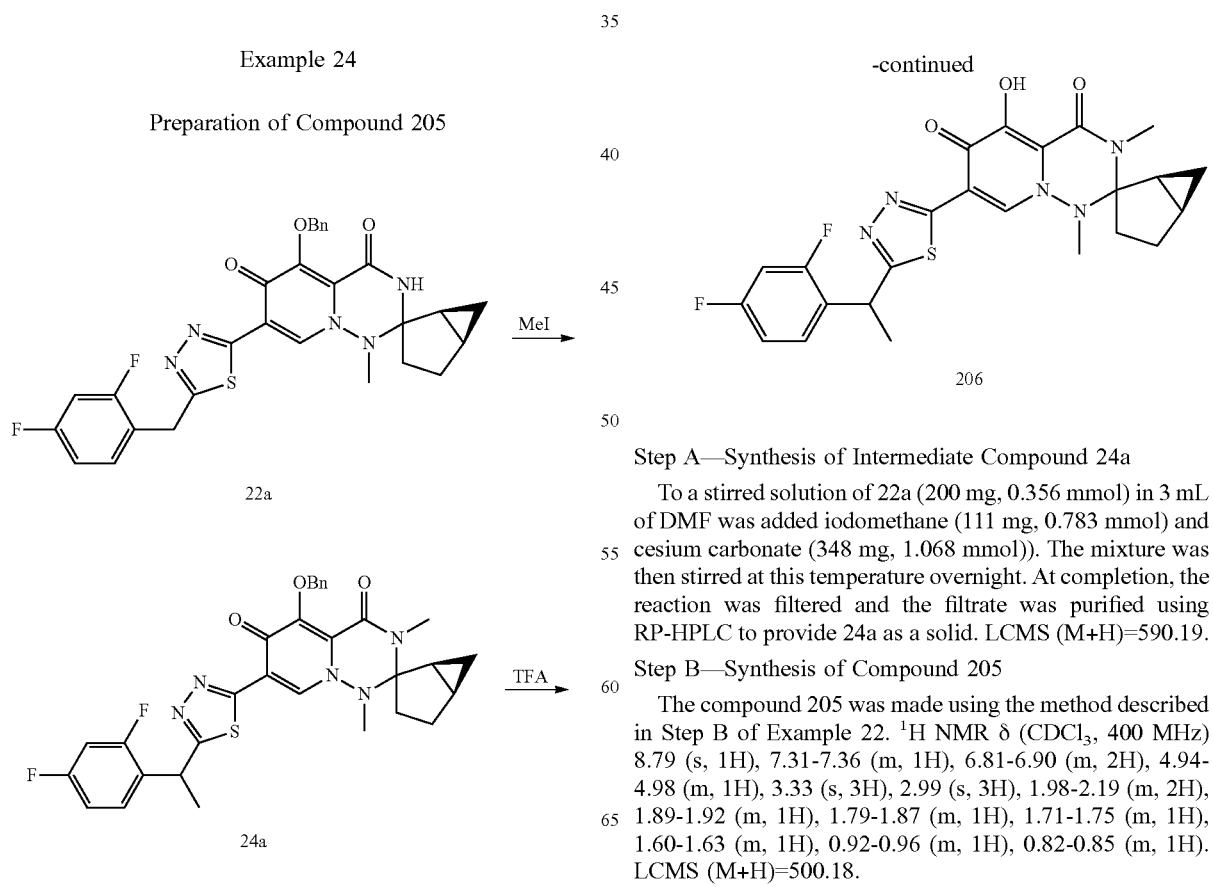

Step A—Synthesis of Intermediate Compound 24a

To a stirred solution of 22a (200 mg, 0.356 mmol) in 3 mL of DMF was added iodomethane (111 mg, 0.783 mmol) and cesium carbonate (348 mg, 1.068 mmol)). The mixture was then stirred at this temperature overnight. At completion, the reaction was filtered and the filtrate was purified using RP-HPLC to provide 24a as a solid. LCMS (M+H)=590.19.

Step B—Synthesis of Compound 205

The compound 205 was made using the method described in Step B of Example 22. $^1$H NMR δ (CDCl$_3$, 400 MHz) 8.79 (s, 1H), 7.31-7.36 (m, 1H), 6.81-6.90 (m, 2H), 4.94-4.98 (m, 1H), 3.33 (s, 3H), 2.99 (s, 3H), 1.98-2.19 (m, 2H), 1.89-1.92 (m, 1H), 1.79-1.87 (m, 1H), 1.71-1.75 (m, 1H), 1.60-1.63 (m, 1H), 0.92-0.96 (m, 1H), 0.82-0.85 (m, 1H). LCMS (M+H)=500.18.

The following compounds of the present invention were prepared using the method described in the Example above using the appropriate reactants and reagents.
| No. | Structure | Exact Mass [M + H]+ |
|---|---|---|
| 206 | 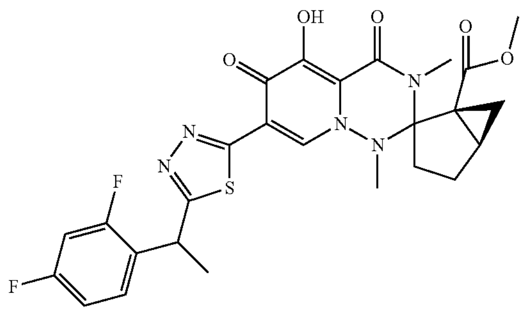 [SMILES: COC(=O)[C@]12C[C@H]1CCC21N(C)C(=O)c2c(O)c(=O)c(-c3nnc(C(C)c4ccc(F)cc4F)s3)cn2N1C] | 558 |
| 207 | 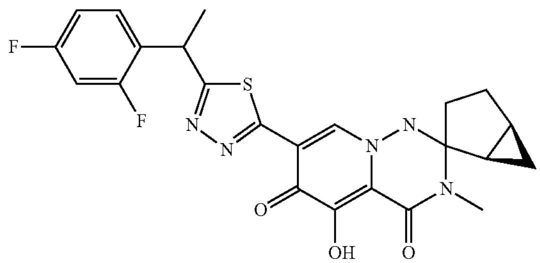 [SMILES: CC(c1nnc(-c2cn3c(c(O)c2=O)C(=O)N(C)C2(CC[C@H]4C[C@H]42)N3)s1)c1ccc(F)cc1F] | 500 |
Example 25
Preparation of Compound 208 and Compound 209
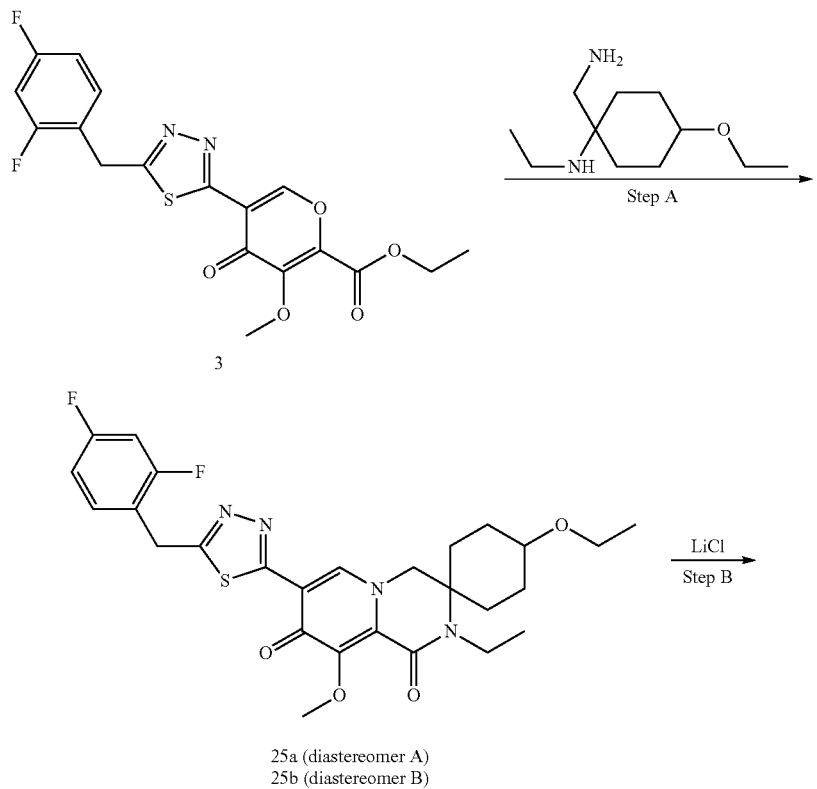
25a (diastereomer A)
25b (diastereomer B)

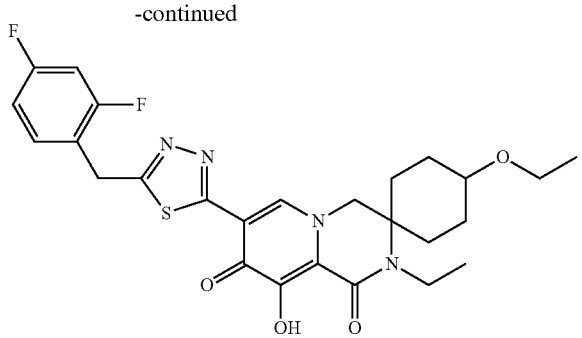

208 (diastereomer A)
209 (diastereomer B)

Step A—Synthesis of Intermediate Compound 25a and Intermediate Compound 25b

Ethyl 5-(5-(2,4-difluorobenzyl)-1,3,4-thiadiazol-2-yl)-3-methoxy-4-oxo-4H-pyran-2-carboxylate 3 (71 mg, 0.174 mmol) and 1-(aminomethyl)-4-ethoxy-N-ethylcyclohexanamine (34.8 mg, 0.174 mmol) were stirred in N-methylimidazole (2 mL) at 65° C. for overnight. After dilution with DMSO, the mixture was directly purified using preparative RP-HPLC to provide as the separated diastereomers: 22a (diastereomer A) LCMS (M+H)=545, 22b (diastereomer B) LCMS (M+H)=545.

Step B—Synthesis of Compound 208 and 209

Intermediate compound 25a (56.4 mg, 0.104 mmol) and lithium chloride (43.9 mg, 1.036 mmol) were stirred in DMF (1 mL) at 100° C. for 3 hours. After dilution with DMSO and ACN, The residue was purified using preparative RP-HPLC to provide compound 208 as a solid. LCMS (M+H)=531; $^1$H NMR (500 MHz, DMSO): δ 12.64 (s; 1 H); 9.11 (s; 1 H); 7.50-7.55 (m; 1 H); 7.29 (td; J=9.8; 2.6 Hz; 1 H); 7.11 (td; J=8.5; 2.6 Hz; 1 H); 4.63 (s; 2 H); 4.49 (s; 2 H); 3.55-3.59 (m; 2 H); 3.45-3.49 (m; 3 H); 1.88-1.95 (m; 4 H); 1.69 (d; J=12.9 Hz; 2 H); 1.48-1.56 (m; 2 H); 1.16 (t; J=7.0 Hz; 3 H); 1.11 (t; J=7.0 Hz; 3 H).

Identical conditions using 25b afforded 209. LCMS (M+H)=531; $^1$H NMR (500 MHz, DMSO): δ 12.67 (s; 1 H); 9.01 (s; 1 H); 7.50-7.55 (m; 1 H); 7.27-7.31 (m; 1 H); 7.09-7.13 (m; 1 H); 4.59 (s; 2 H); 4.49 (s; 2 H); 3.53-3.56 (m; 2 H); 3.42 (q; J=7.0 Hz; 2 H); 2.04 (dd; J=15.0; 11.6 Hz; 2 H); 1.82 (d; J=13.9 Hz; 3 H); 1.68 (t; J=14.1 Hz; 2 H); 1.46 (d; J=12.9 Hz; 2 H); 1.19 (t; J=7.0 Hz; 3 H); 1.14 (t; J=7.0 Hz; 3 H)

The following compounds of the present invention were prepared using the method described in the Example above using the appropriate reactants and reagents.

| No. | Structure | Exact Mass [M + H]+ |
|---|---|---|
| 210 | 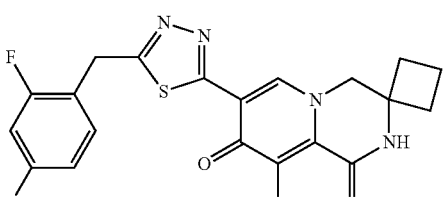 | 431 |
| 211 | 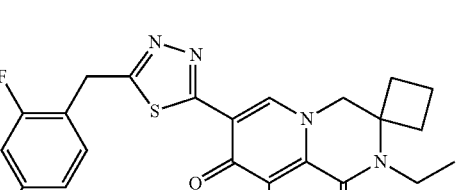 | 459 |

-continued

| No. | Structure | Exact Mass [M + H]+ |
|---|---|---|
| 212 | 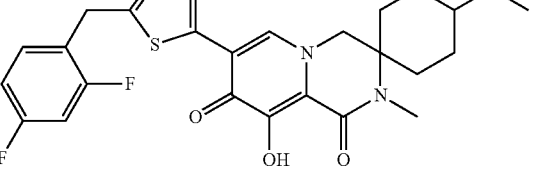 (diastereomer) | 503 |
| 213 | 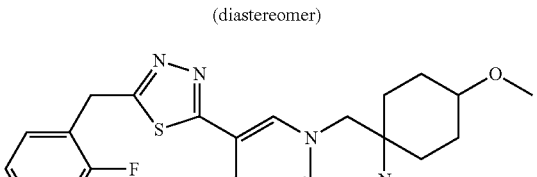 (diastereomer) | 503 |
| 214 | 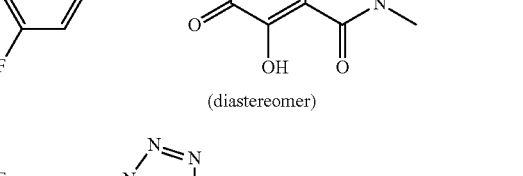 | 472 |
| 215 | 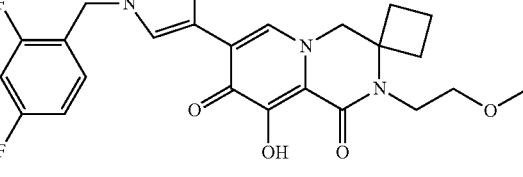 | 428 |
| 216 | 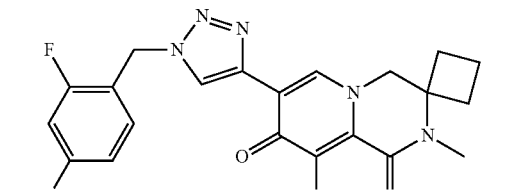 | 442 |

Example 26

Assay for inhibition of HIV replication

MT4-GFP cells (250,000 cells/ml) were bulk-infected with HIV-1 (NL4-3 strain) at low multiplicity of infection (MOI) in RPMI+10% FBS for 24 hours. Cells were then washed once in RPMI+10% FBS and resuspended RPMI+ 10% or 50% normal human serum (NHS). Test compounds were serial-diluted in DMSO on ECHO. The infected MT4-GFP cells were added to a 384-well poly-D-lysine coated black plate with clear bottom in which the diluted test compounds were placed. The cells were seeded at 8,000 cells per well and the final DMSO concentration was 0.4%. The infected cells (Green GFP cells) were quantified at both 24 and 48 hours post incubation using Acumen eX3. Viral reproductive ratio ($R_0$) was determined using the number of infected cells at 48 hours divided by the number of infected cells at 24 hours. Percent viral growth inhibition was calculated by $[1-(R-R_{tripledrug})/(R_{DMSO}-R_{tripledrug})]*100$. Compound potency IP or IC50 was determined by a 4-parameter dose response curve analysis.

| Compound No. | ViKinG IP (nM) with 0% NHS | ViKinG IP (nM) with 10% NHS | ViKinG IP (nM) with 100% NHS |
|---|---|---|---|
| 5 | NA | 30.96 | 936.5 |
| 6 | NA | 30.79 | 357.4 |

| Compound No. | ViKinG IP (nM) with 0% NHS | ViKinG IP (nM) with 10% NHS | ViKinG IP (nM) with 100% NHS |
|---|---|---|---|
| 7 (diastereomer A) | NA | 32.74 | 523.3 |
| 7 (diastereomer B) | NA | 19.99 | 404.6 |
| 9 | 5.061 | NA | 140.9 |
| 10 | 10.99 | NA | 161.1 |
| 11 | NA | 230.9 | 4202 |
| 13 | 23.76 | 86.86 | 862.4 |
| 14 | 5.373 | 18.77 | 197.9 |
| 15 | 3.489 | 57.89 | 970.9 |
| 16 | NA | 56.96 | 1026 |
| 17 | NA | 138.4 | 4069 |
| 18 | NA | 38.69 | 1193 |
| 19 | NA | 22.78 | 314.2 |
| 20 | NA | 28.74 | 218.5 |
| 21 | NA | 31.8 | NA |
| 22 | NA | 291.5 | NA |
| 23 | NA | 466.2 | NA |
| 24 | NA | 185.2 | 1035 |
| 25 | NA | 40.48 | NA |
| 26 | 2.831 | 9.224 | 115.2 |
| 27 | 9.244 | 11.46 | 191.1 |
| 28 | NA | 11.99 | NA |
| 29 | NA | 15.36 | NA |
| 30 | NA | 13.05 | NA |
| 31 | NA | 32.21 | NA |
| 32 | NA | 21.14 | NA |
| 33 | NA | 29 | NA |
| 34 | NA | 23.63 | 179.7 |
| 35 | NA | 100.2 | NA |
| 36 | NA | 52.59 | NA |
| 37 | NA | 18.18 | 186.1 |
| 38 | NA | 95.42 | NA |
| 39 | 0.2135 | 77.68 | NA |
| 40 | 2.529 | 374.5 | NA |
| 41 | 3.145 | 73.23 | NA |
| 42 | 92.49 | 320.7 | NA |
| 43 | 40.72 | 275.1 | NA |
| 44 | 4.364 | NA | 239.6 |
| 45 | 4.069 | NA | 121.8 |
| 46 | 6.782 | NA | 138.6 |
| 47 | 11.56 | NA | 186.2 |
| 48 | 19.59 | NA | 415.8 |
| 49 | 19.78 | NA | 406.2 |
| 50 | 25.56 | NA | 5383 |
| 51 | 8.501 | NA | 203.7 |
| 52 | 2.33 | NA | 130.1 |
| 53 | 15.71 | NA | 1029 |
| 54 | 82.84 | NA | 1466 |
| 55 | 6.455 | NA | 278.7 |
| 56 | 11.97 | NA | 1978 |
| 57 | 18.06 | NA | 145.3 |
| 58 | 14.06 | NA | 227.9 |
| 59 | 8.66 | NA | 124.5 |
| 60 | 10.79 | NA | 226.2 |
| 61 | 23.75 | NA | 221 |
| 62 | 8.109 | NA | 159.2 |
| 63 | 27.59 | NA | 390.9 |
| 64 | 3.3 | NA | 77.15 |
| 65 | 6.268 | NA | 122.8 |
| 66 | 12.03 | NA | 93.89 |
| 67 | 12.54 | NA | 160.1 |
| 68 | NA | 10.54 | NA |
| 69 | 22.62 | 84.65 | NA |
| 70 | 9.897 | 39.13 | NA |
| 71 | 16.12 | 49.53 | NA |
| 72 | 6.074 | 9.932 | NA |
| 73 | 7.044 | 11.86 | NA |
| 74 | 6.839 | 23.62 | NA |
| 75 | 5.016 | 35.26 | NA |
| 76 | 17.33 | 23.62 | 760.8 |
| 77 | 12.76 | 57.96 | NA |
| 78 | 10.67 | 93.01 | NA |
| 79 | 3.107 | 40.88 | NA |
| 80 | 50.14 | NA | 915.2 |
| 81 | 37.49 | NA | 1610 |
| 82 | 63.68 | NA | 2565 |
| 83 | 151.1 | 755.1 | NA |
| 84 | 51.49 | 209.1 | NA |
| 85 | 12.49 | 29.49 | 149.5 |
| 86 | 6.339 | 94.29 | 184.6 |
| 87 | 626.5 | NA | 2893 |
| 88 | 1279 | 4202 | NA |
| 89 | 44.88 | 321.5 | NA |
| 91 | 10.47 | NA | 117.6 |
| 92 | 3.573 | NA | 65.27 |
| 93 | NA | 254.8 | NA |
| 94 | NA | 9.83 | 130.2 |
| 96 | 8.634 | 16.19 | 170.7 |
| 97 | NA | 23.4 | 133.2 |
| 98 | NA | 32.17 | 167.8 |
| 99 | NA | 34.91 | 122.5 |
| 100 | 7.507 | 6.473 | 111.2 |
| 101 | NA | 37.46 | NA |
| 102 | 12.22 | NA | 169.9 |
| 103 | 6.883 | NA | 142.9 |
| 106 | 186 | 812.1 | NA |
| 107 | 4.965 | 46.4 | NA |
| 108 | 23.98 | 16.08 | 477.5 |
| 109 | 12.07 | 18.24 | NA |
| 110 | 5.821 | 10.69 | NA |
| 111 | 26.55 | 193 | NA |
| 112 | 3.357 | 11.05 | NA |
| 113 | 22.18 | 72.21 | NA |
| 114 | 4.693 | 9.074 | NA |
| 115 | 16.45 | 39.49 | NA |
| 116 | 3.937 | 15.18 | NA |
| 117 | 20.45 | 42.68 | NA |
| 118 | 14.4 | 8.428 | NA |
| 119 | 5.259 | 35.57 | 189.2 |
| 120 | 5.51 | 11.67 | 516.2 |
| 121 | 102.2 | 240.5 | NA |
| 122 | 5.513 | 18.43 | NA |
| 123 | 47.12 | 102.8 | NA |
| 124 | 11.35 | 22.6 | NA |
| 125 | 373.9 | 542.9 | NA |
| 126 | 24.31 | 82.21 | NA |
| 127 | 111.8 | 375.5 | NA |
| 128 | 81.85 | 100.9 | NA |
| 129 | 67.69 | 1076 | NA |
| 130 | 13.73 | 33.87 | NA |
| 131 | 459.3 | 641.5 | NA |
| 132 | 108.8 | 173 | NA |
| 133 | 190.1 | 547.7 | NA |
| 134 | 20.86 | 122.2 | NA |
| 135 | 76.35 | 289.5 | NA |
| 136 | 30.8 | 151 | NA |
| 137 | 108 | 706.8 | NA |
| 138 | 445.2 | 1184 | NA |
| 139 | 54.3 | 186.1 | NA |
| 140 | 61.61 | 28.25 | NA |
| 141 | 59.66 | NA | 1994 |
| 142 | 5.629 | NA | 557.7 |
| 143 | 7.477 | NA | 817.4 |
| 144 | 10.69 | NA | 205.1 |
| 145 | NA | 101.9 | NA |
| 146 | NA | 9.015 | 188.2 |
| 147 | NA | 15.07 | 117.4 |
| 148 | NA | 8.596 | 119 |
| 149 | NA | 43.7 | NA |
| 150 | 13.28 | 18.91 | 221.2 |
| 153 | NA | 16.48 | 1431 |
| 154 | NA | 33.92 | 1593 |
| 155 | NA | 48.67 | 304.4 |
| 156 | NA | 26.71 | 988.9 |
| 157 | NA | 14.15 | 612.9 |
| 158 | NA | 17.7 | 502.9 |
| 159 | NA | 121 | NA |
| 160 | NA | 22.57 | 298.2 |
| 161 | NA | 41.1 | 464.6 |
| 162 | NA | 10.83 | 186 |
| 163 | 8.22 | NA | 499.4 |

-continued

| Compound No. | ViKinG IP (nM) with 0% NHS | ViKinG IP (nM) with 10% NHS | ViKinG IP (nM) with 100% NHS |
|---|---|---|---|
| 164 | 3.477 | NA | 82.19 |
| 165 | 5.124 | NA | 54.03 |
| 166 | 8.997 | NA | 162 |
| 167 | 2.521 | NA | 41.87 |
| 169 | NA | 90 | 1512 |
| 171 | NA | 21.03 | 672.8 |
| 173 | 6.999 | NA | 526.2 |
| 174 | 2.865 | NA | 125.1 |
| 175 | 1.539 | NA | 37.12 |
| 176 | 2.122 | NA | 38.96 |
| 177 | 5.029 | NA | 4787 |
| 178 | 2.735 | NA | 232.8 |
| 179 | 2.86 | NA | 1356 |
| 180 | 1.804 | NA | 611.4 |
| 181 | 2.483 | NA | 28.87 |
| 182 | 4.019 | NA | 45.48 |
| 183 | 3.166 | NA | 188 |
| 184 | 2.659 | NA | 177.7 |
| 185 | 2.197 | NA | 211.7 |
| 186 | 1.742 | NA | 282.8 |
| 187 | 3.642 | NA | 501.5 |
| 188 | 1.485 | NA | 405.5 |
| 189 | 3.615 | NA | 626.1 |
| 190 | 28.97 | NA | 2907 |
| 191 | 6.738 | NA | 239 |
| 192 | 3.661 | NA | 67.19 |
| 193 | 8.245 | NA | 84.83 |
| 194 | 24.98 | NA | 399.9 |
| 195 | 2.016 | NA | 190.1 |
| 196 | 1.613 | NA | 307.4 |
| 197 | 2.327 | NA | 162.4 |
| 198 | 4.58 | NA | 318.7 |
| 199 | 5.417 | 13.95 | 201.8 |
| 200 | 2.035 | NA | 66.67 |
| 201 | 3.822 | NA | 575.2 |
| 202 | 8.356 | 1185 | NA |
| 203 | 1.579 | 14.12 | 231.1 |
| 204 | 2.81 | 9.045 | 145.7 |
| 205 | 6.683 | NA | 778.7 |
| 206 | 15.43 | 62.4 | NA |
| 207 | 15.43 | 79.99 | NA |
| 208 | 14.27 | 10.31 | 125.2 |
| 209 | 25.45 | NA | 257.5 |
| 210 | 4.111 | 68.4 | NA |
| 211 | 10.29 | NA | 2798 |
| 212 | 3.492 | NA | 90.67 |
| 213 | 5.895 | NA | 35.79 |
| 214 | 24.42 | NA | 205.2 |
| 215 | 9.93 | NA | 76.13 |
| 216 | 13.19 | NA | 332.2 |
| 217 | NA | 65.97 | 1020 |
| 219 | NA | 26.95 | NA |
| 222 | 1.281 | NA | NA |
| 223 | NA | NA | 368.9 |
| 224 | NA | 49.27 | 361.1 |

NA = not available

Treatment or Prevention of HIV Infection

The 4-Pyridinonetriazine Derivatives are useful in the inhibition of HIV, the inhibition of HIV integrase, the treatment of HIV infection and/or reduction of the likelihood or severity of symptoms of HIV infection and the inhibition of HIV viral replication and/or HIV viral production in a cell-based system. For example, the 4-Pyridinonetriazine Derivatives are useful in treating infection by HIV after suspected past exposure to HIV by such means as blood transfusion, exchange of body fluids, bites, accidental needle stick, or exposure to subject blood during surgery or other medical procedures.

Accordingly, in one embodiment, the invention provides methods for treating HIV infection in a subject, the methods comprising administering to the subject an effective amount of at least one 4-Pyridinonetriazine Derivative or a pharmaceutically acceptable salt thereof. In a specific embodiment, the amount administered is effective to treat or prevent infection by HIV in the subject. In another specific embodiment, the amount administered is effective to inhibit HIV viral replication and/or viral production in the subject. In one embodiment, the HIV infection has progressed to AIDS.

The 4-Pyridinonetriazine Derivatives are also useful in the preparation and execution of screening assays for antiviral compounds. For example the 4-Pyridinonetriazine Derivatives are useful for identifying resistant HIV cell lines harboring mutations, which are excellent screening tools for more powerful antiviral compounds. Furthermore, the 4-Pyridinonetriazine Derivatives are useful in establishing or determining the binding site of other antivirals to the HIV Integrase.

The compositions and combinations of the present invention can be useful for treating a subject suffering from infection related to any HIV genotype.

Combination Therapy

In another embodiment, the present methods for treating or preventing HIV infection can further comprise the administration of one or more additional therapeutic agents which are not 4-Pyridinonetriazine Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: (i) at least one 4-Pyridinonetriazine Derivative (which may include two or more different 4-Pyridinonetriazine Derivatives), or a pharmaceutically acceptable salt thereof, and (ii) at least one additional therapeutic agent that is other than a 4-Pyridinonetriazine Derivative, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a 4-Pyridinonetriazine Derivative and an additional therapeutic agent may be present in fixed amounts (dosage amounts) in a single dosage unit (e.g., a capsule, a tablet and the like).

In one embodiment, the at least one 4-Pyridinonetriazine Derivative is administered during a time when the additional therapeutic agent(s) exert their prophylactic or therapeutic effect, or vice versa.

In another embodiment, the at least one 4-Pyridinonetriazine Derivative and the additional therapeutic agent(s) are administered in doses commonly employed when such agents are used as monotherapy for treating a viral infection.

In another embodiment, the at least one 4-Pyridinonetriazine Derivative and the additional therapeutic agent(s) are administered in doses lower than the doses commonly employed when such agents are used as monotherapy for treating a viral infection.

In still another embodiment, the at least one 4-Pyridinonetriazine Derivative and the additional therapeutic agent(s) act synergistically and are administered in doses lower than the doses commonly employed when such agents are used as monotherapy for treating a viral infection.

In one embodiment, the at least one 4-Pyridinonetriazine Derivative and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HIV infection.

In another embodiment, the viral infection is AIDS.

The at least one 4-Pyridinonetriazine Derivative and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one 4-Pyridinonetriazine Derivative and the additional therapeutic agent(s) may inhibit the resistance of a viral infection to these agents.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, imunomodulators, antiinfectives, or vaccines useful for treating HIV infection or AIDS. Suitable HIV antivirals for use in combination with the compounds of the present invention include, for example, those listed in Table A as follows:

TABLE A

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| Dolutegravir | InI |

TABLE A-continued

| Name | Type |
|---|---|
| efavirenz, EFV, Sustiva ®, Stocrin ® | nnRTI |
| efavirenz + emtricitabine + tenofovir DF, Atripla ® | nnRTI + nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| raltegravir, MK-0518, Isentress ® | InI |
| rilpivirine, TMC-278 | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor.
Some of the drugs listed in the table are used in a salt form; e.g., abacavir sulfate, indinavir sulfate, atazanavir sulfate, nelfinavir mesylate.

In one embodiment, the one or more anti-HIV drugs are selected from raltegravir, lamivudine, abacavir, ritonavir, dolutegravir, darunavir, atazanavir, emtricitabine, tenofovir, elvitegravir, rilpivirine and lopinavir.

In another embodiment, the compound of formula (I) is used in combination with a single anti-HIV drug which is raltegravir.

In another embodiment, the compound of formula (I) is used in combination with a single anti-HIV drug which is lamivudine.

In still another embodiment, the compound of formula (I) is used in combination with a single anti-HIV drug which is atazanavir.

In another embodiment, the compound of formula (I) is used in combination with a single anti-HIV drug which is darunavir.

In another embodiment, the compound of formula (I) is used in combination with a single anti-HIV drug which is rilpivirine.

In yet another embodiment, the compound of formula (I) is used in combination with a single anti-HIV drug which is dolutegravir.

In another embodiment, the compound of formula (I) is used in combination with a single anti-HIV drug which is elvitegravir.

In one embodiment, the compound of formula (I) is used in combination with two anti-HIV drugs which are lamivudine and abacavir.

In another embodiment, the compound of formula (I) is used in combination with two anti-HIV drugs which are darunavir and raltegravir.

In another embodiment, the compound of formula (I) is used in combination with two anti-HIV drugs which are emtricitabine and tenofovir.

In still another embodiment, the compound of formula (I) is used in combination with two anti-HIV drugs which are atazanavir and raltegravir.

In another embodiment, the compound of formula (I) is used in combination with two anti-HIV drugs which are ritonavir and lopinavir.

In another embodiment, the compound of formula (I) is used in combination with two anti-HIV drugs which are lamivudine and raltegravir.

In one embodiment, the compound of formula (I) is used in combination with three anti-HIV drug which are abacavir, lamivudine and raltegravir.

In another embodiment, the compound of formula (I) is used in combination with three anti-HIV drug which are lopinavir, ritonavir and raltegravir.

In one embodiment, the present invention provides pharmaceutical compositions comprising (i) a compound of formula (I) or a pharmaceutically acceptable salt thereof; (ii) a pharmaceutically acceptable carrier; and (iii) one or more additional anti-HIV agents selected from lamivudine, abacavir, ritonavir and lopinavir, or a pharmaceutically acceptable salt thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt thereof and (ii) one or more additional anti-HIV agents selected from lamivudine, abacavir, ritonavir and lopinavir, or a pharmaceutically acceptable salt thereof, wherein the amounts administered of components (i) and (ii) are together effective for the treatment or prophylaxis of infection by HIV or for the treatment, prophylaxis, or delay in the onset or progression of AIDS in the subject in need thereof It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, 57$^{th}$ edition (2003), the 58$^{th}$ edition (2004), the 59$^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection can be determined by the attending clinician, taking into consideration the approved doses and dosage regimen in the package insert; the age, sex and general health of the subject; and the type and severity of the viral infection or related disease or disorder. When administered in combination, the 4-Pyridinonetriazine Derivative(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Compositions and Administration

When administered to a subject, the 4-Pyridinonetriazine Derivatives can be administered as a component of a composition that comprises a pharmaceutically acceptable carrier or vehicle. The present invention provides pharmaceutical compositions comprising an effective amount of at least one 4-Pyridinonetriazine Derivative and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more 4-Pyridinonetriazine Derivatives are administered orally.

In another embodiment, the one or more 4-Pyridinonetriazine Derivatives are administered intravenously.

In one embodiment, a pharmaceutical preparation comprising at least one 4-Pyridinonetriazine Derivative is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the 4-Pyridinonetriazine Derivative(s) by weight or volume. In various embodiments, the present compositions can contain, in one embodiment, from about 1% to about 70% or from about 5% to about 60% of the 4-Pyridinonetriazine Derivative(s) by weight or volume.

The compounds of Formula I can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the 4-Pyridinonetriazine Derivatives will be regulated according to the judgment of the attending clinician considering such factors as age, condition and size of the subject as well as severity of the symptoms being treated. The compositions of the invention can further comprise one or more additional therapeutic agents, selected from those listed above herein.

Kits

In one aspect, the present invention provides a kit comprising a therapeutically effective amount of at least one 4-Pyridinonetriazine Derivative, or a pharmaceutically acceptable salt or prodrug of said compound and a pharmaceutically acceptable carrier, vehicle or diluent.

In another aspect the present invention provides a kit comprising an amount of at least one 4-Pyridinonetriazine Derivative, or a pharmaceutically acceptable salt or prodrug of said compound and an amount of at least one additional therapeutic agent listed above, wherein the amounts of the two or more active ingredients result in a desired therapeutic effect. In one embodiment, the one or more 4-Pyridinonetriazine Derivatives and the one or more additional therapeutic agents are provided in the same container. In one embodiment, the one or more 4-Pyridinonetriazine Derivatives and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound having the formula:

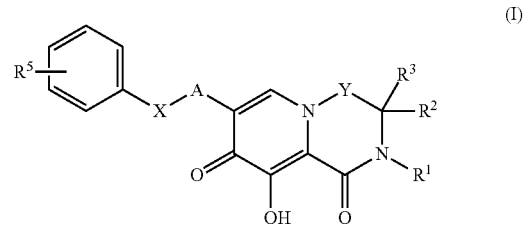

(I)

or a pharmaceutically acceptable salt thereof, wherein:

A is —NHC(O)— or 5 or 6-membered monocyclic heteroaryl;

X is $C_1$-$C_3$ alkylene;

Y is O, —C($R^8$)$_2$— or —N($R^4$)—;

$R^1$ is $C_1$-$C_6$ alkyl, $C_3$-$C_7$ cycloalkyl or —($C_1$-$C_4$ alkylene)-O—($C_1$-$C_6$ alkyl);

$R^2$ is selected from H, $C_1$-$C_6$ alkyl, $C_1$-$C_6$ hydroxyalkyl, —($C_1$-$C_6$ alkylene)$_p$-C(O)O$R^6$, —($C_1$-$C_6$ alkylene)$_p$-C(O)$R^6$, —($C_1$-$C_6$ alkylene)$_p$-C(O)N($R^9$)$_2$, $C_3$-$C_7$ cycloalkyl, 5 or 6-membered monocyclic heterocycloalkyl, 5 or 6-membered monocyclic heteroaryl and —($C_1$-$C_4$ alkylene)-O—($C_1$-$C_6$ alkyl), wherein said $C_3$-$C_7$ cycloalkyl group, said 5 or 6-membered monocyclic heteroaryl group and said 5 or 6-membered monocyclic heterocycloalkyl group can be optionally substituted with $R^7$;

$R^3$ is selected from H, $C_1$-$C_6$ alkyl, $C_3$-$C_7$ cycloalkyl, 5 or 6-membered monocyclic heterocycloalkyl and —($C_1$-$C_4$ alkylene)-O—($C_1$-$C_6$ alkyl), wherein said $C_3$-$C_7$ cycloalkyl group and said 5 or 6-membered monocyclic heterocycloalkyl group can be optionally substituted with one or more groups selected from $R^7$, or $R^2$ and $R^3$, together with the common carbon atom to which they are both attached, can optionally join to form a spirocyclic $C_3$-$C_7$ cycloalkyl group or a spirocyclic $C_3$-$C_7$ cycloalkenyl group, wherein said spirocyclic $C_3$-$C_7$ cycloalkyl group and said spirocyclic $C_3$-$C_7$ cycloalkenyl group can be optionally substituted with one or more groups selected from $R^7$, and wherein said spirocyclic $C_3$-$C_7$ cycloalkyl group can be fused to another ring, selected from $C_3$-$C_7$ cycloalkyl, 3 to 8-membered monocyclic heterocycloalkyl and 5 or 6-membered monocyclic heteroaryl, and wherein said spirocyclic $C_3$-$C_7$ cycloalkyl group can form a spirocyclic ring system with a $C_3$-$C_7$ cycloalkyl group or a 3 to 8-membered monocyclic heterocycloalkyl group, or $R^1$ and $R^3$, together with the carbon atoms to which they are attached, can optionally join to form a 3 to 8-membered monocyclic heterocycloalkyl group, which can be optionally substituted with one or more groups selected from $R^7$;

$R^4$ is selected from H, $C_1$-$C_6$ alkyl, —$SO_2R^6$, —$C(O)R^6$, —($C_1$-$C_6$ alkylene)$_p$-$C(O)N(R^9)_2$, and —($C_2$-$C_4$ alkylene)-O—($C_1$-$C_6$ alkyl);

$R^5$ represents up to 3 optional substitutents, each independently selected from halo, $C_1$-$C_6$ alkyl, —O—($C_1$-$C_6$ alkyl) and $C_1$-$C_6$ haloalkyl; and each occurrence of $R^6$ is independently selected from $C_1$-$C_6$ alkyl, $C_1$-$C_6$ haloalkyl, $C_3$-$C_7$ cycloalkyl, phenyl, 3 to 8-membered monocyclic heterocycloalkyl or 6-membered monocyclic heteroaryl and 8 to 10-membered bicyclic heteroaryl, wherein said $C_3$-$C_7$ cycloalkyl group, said phenyl group, said 5 or 6-membered monocyclic heteroaryl group and said 8 to 10-membered bicyclic heteroaryl group can be optionally substituted with $R^7$;

each occurrence of $R^7$ is independently selected from halo, $C_1$-$C_6$ alkyl, $C_1$-$C_6$ haloalkyl, 3 to 8-membered monocyclic heterocycloalkyl, 6 to 10-membered bicyclic heterocycloalkyl, —O—($C_1$-$C_6$ alkyl), —O—($C_6$-$C_{10}$ aryl), —O—($C_1$-$C_6$ alkylene)-O—($C_1$-$C_6$ alkyl), —O—($C_1$-$C_6$ haloalkyl), —O—($C_1$-$C_6$ alkylene)-O—($C_1$-$C_6$ alkylene)-O—($C_1$-$C_6$ alkyl), —$NH_2$, —NH($C_1$-$C_6$ alkyl), —N($C_1$-$C_6$ alkyl)$_2$, —$S(O)_2$—($C_1$-$C_6$ alkyl), —$NHS(O)_2$—($C_1$-$C_6$ alkyl), —OC(O)—($C_1$-$C_6$ haloalkyl), —($C_1$-$C_6$ alkylene)$_p$-C(O)OR$^6$, —($C_1$-$C_6$ alkylene)$_p$-C(O)R$^6$, —($C_1$-$C_6$ alkylene)$_p$-C(O)N(R$^9$)$_2$, $C_1$-$C_6$ hydroxyalkyl, —$P(O)(OR^{11})_2$, and —CN;

each occurrence of $R^8$ is independently selected from H, $C_1$-$C_6$ alkyl, $C_3$-$C_7$ cycloalkyl, 3 to 8-membered monocyclic heterocycloalkyl and 5 or 6-membered monocyclic heteroaryl;

each occurrence of $R^9$ is independently selected from H, $C_1$-$C_6$ alkyl, $C_3$-$C_7$ cycloalkyl, —($C_1$-$C_6$ alkylene)-N(R$^9$)$_2$, $C_1$-$C_6$ haloalkyl, —C(O)O($C_1$-$C_6$ alkyl), —($C_1$-$C_6$ alkylene)$_p$-R$^{10}$ and —($C_1$-$C_6$ alkylene)-O—($C_1$-$C_6$ alkyl);

each occurrence of $R^{10}$ is independently selected from H, $C_1$-$C_6$ alkyl, $C_3$-$C_7$ cycloalkyl, 5 or 6-membered monocyclic heteroaryl and 3 to 8-membered monocyclic heterocycloalkyl;

each occurrence of $R^{11}$ is independently selected from H and $C_1$-$C_6$ alkyl; and each occurrence of p is independently 0 or 1.

2. The compound of claim 1, wherein Y is O, or a pharmaceutically acceptable salt thereof.

3. The compound of claim 1, wherein Y is —CHR$^8$— or —N(R$^4$)—; or a pharmaceutically acceptable salt thereof.

4. The compound of claim 1, wherein A is —NH—C(O)—, or a pharmaceutically acceptable salt thereof.

5. The compound of claim 1, wherein A is 5 or 6-membered monocyclic heteroaryl, or a pharmaceutically acceptable salt thereof.

6. The compound of claim 1 having the formula (Ia):

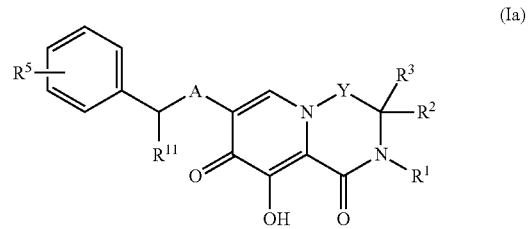

(Ia)

or a pharmaceutically acceptable salt thereof,
wherein:
A is —NHC(O)— or 5-membered heteroaryl;
Y is selected from O, —NHR$^4$, —$CH_2$— or —CH(CH$_3$)—;
$R^1$ is $C_1$-$C_6$ alkyl or —$CH_2CH_2OCH_3$;
$R^2$ is selected from H, $C_1$-$C_6$ alkyl, and —($C_1$-$C_4$ alkylene)-O—($C_1$-$C_6$ alkyl);
$R^3$ is selected from $C_1$-$C_6$ alkyl, $C_3$-$C_7$ cycloalkyl, 5 or 6-membered monocyclic heterocycloalkyl and —($C_1$-$C_4$ alkylene)-O—($C_1$-$C_6$ alkyl), or $R^2$ and $R^3$, together with the common carbon atom to which they are both attached, join to form a spirocyclic $C_3$-$C_7$ cycloalkyl group which can be optionally substituted as set forth in claim 1, or $R^1$ and $R^3$, together with the atoms o which they are attached, join to form a 3 to 8-membered heterocycloalkyl group, which can be optionally substituted as set forth above for the compounds of formula (I);
$R^4$ is selected from H, $C_1$-$C_6$ alkyl and —($C_2$-$C_4$ alkylene)-O—($C_1$-$C_6$ alkyl);
$R^5$ represents up to 2 optional substitutents, each independently selected from halo; and
$R^{11}$ is H or methyl.

7. The compound of claim 1 having the formula (Ib):

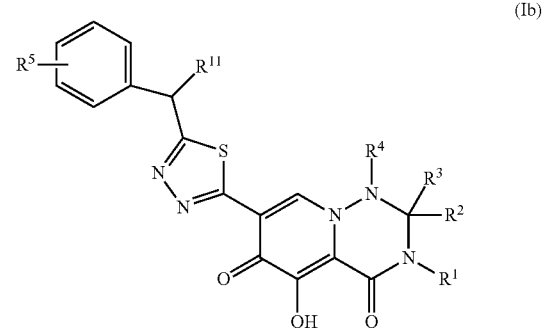

(Ib)

or a pharmaceutically acceptable salt thereof,
wherein:
$R^1$ is $C_1$-$C_6$ alkyl;
$R^2$ is selected from H, $C_1$-$C_6$ alkyl, and —($C_1$-$C_4$ alkylene)-O—($C_1$-$C_6$ alkyl);
$R^3$ is selected from $C_1$-$C_6$ alkyl, $C_3$-$C_7$ cycloalkyl, 5 or 6-membered monocyclic heterocycloalkyl and —($C_1$-$C_4$ alkylene)-O—($C_1$-$C_6$ alkyl), or $R^2$ and $R^3$, together with the common carbon atom to which they are both attached, join to form a spirocyclic $C_3$-$C_7$ cycloalkyl group which can be optionally substituted as set forth in claim 1;

R[4] is selected from H, $C_1$-$C_6$ alkyl and —($C_2$-$C_4$ alkylene)-O—($C_1$-$C_6$ alkyl);

R[5] represents up to 2 optional substitutents, each being fluoro; and

R[11] is H or methyl.

8. The compound of claim 1, wherein R[2] is H, methyl or —$CH_2CH_2OCH_3$, or a pharmaceutically acceptable salt thereof.

9. The compound of claim 1, wherein R[3] is methyl, cyclopropyl, —$CH_2CH_2OCH_3$ or tetrahyrdopyranyl, or a pharmaceutically acceptable salt thereof.

10. The compound of claim 1, wherein R[2] and R[3], together with the common carbon atom to which they are both attached, join to form a spirocyclic $C_3$-$C_7$ cycloalkyl group that is optionally substituted as set forth in claim 1, or a pharmaceutically acceptable salt thereof.

11. The compound of claim 1, wherein R[1] and R[3], together with the atoms to which they are both attached, join to form a 3 to 8-membered monocyclic heterocycloalkyl group that is optionally substituted as set forth in claim 1, or a pharmaceutically acceptable salt thereof.

12. The compound of claim 1, wherein R[4] is methyl or —$CH_2CH_2OCH_3$, or a pharmaceutically acceptable salt thereof.

13. The compound of claim 1, wherein R[5] represents: (i) a single fluoro group in the para position or (ii) two fluoro groups, in the ortho and para positions, or a pharmaceutically acceptable salt thereof.

14. A compound selected from

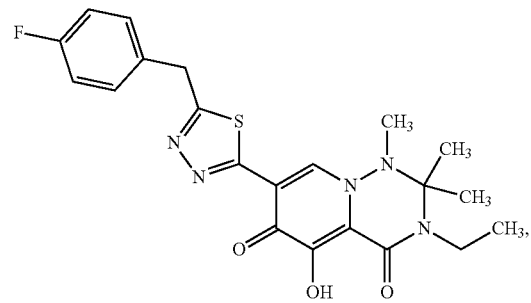

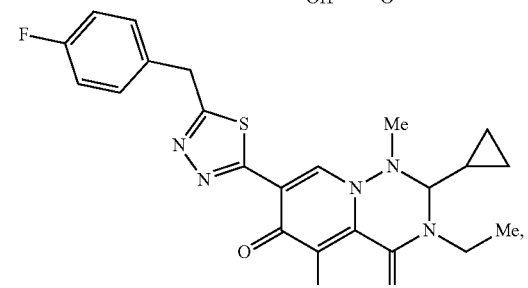

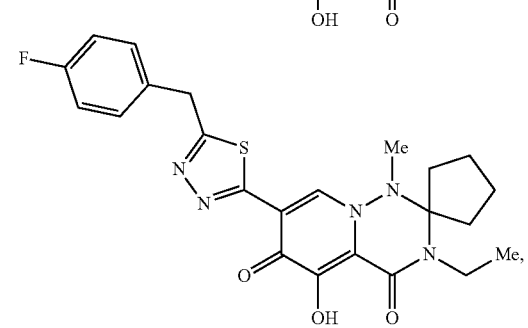

-continued

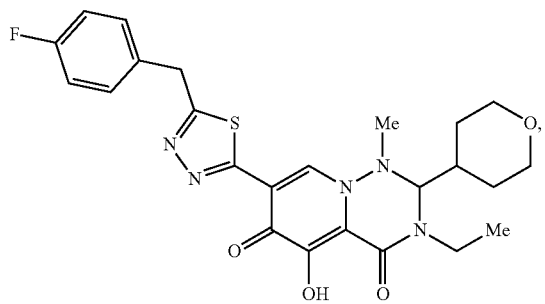

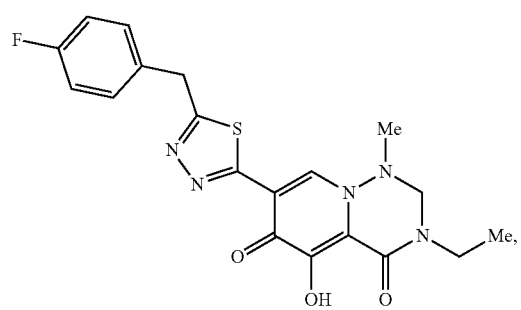

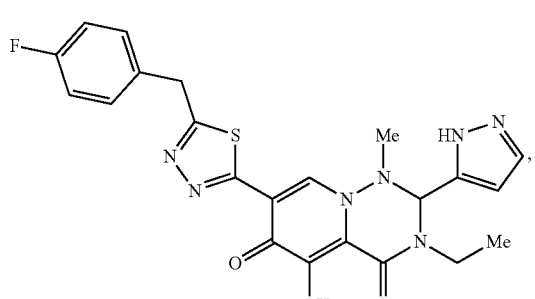

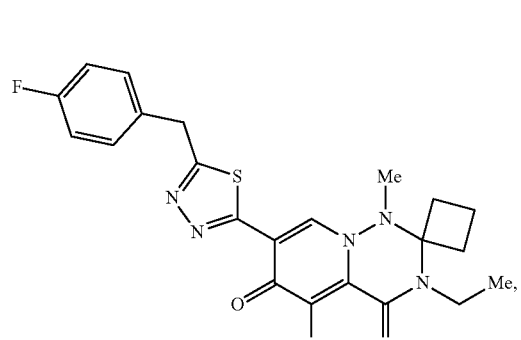

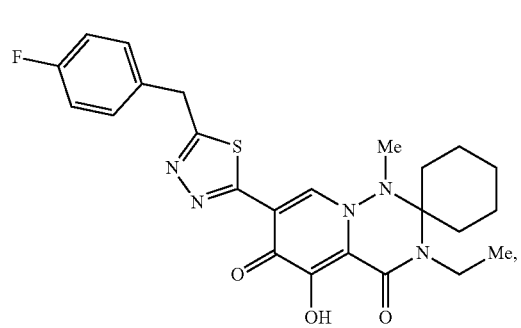

161
-continued
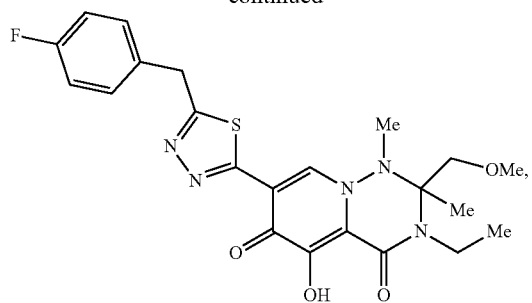
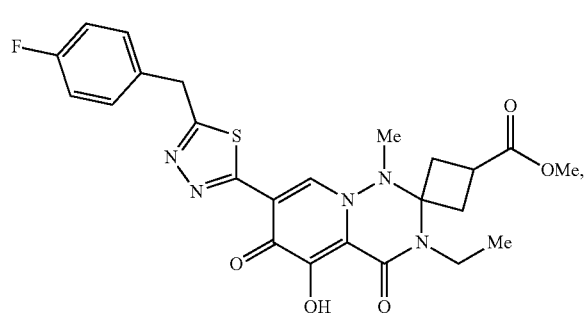
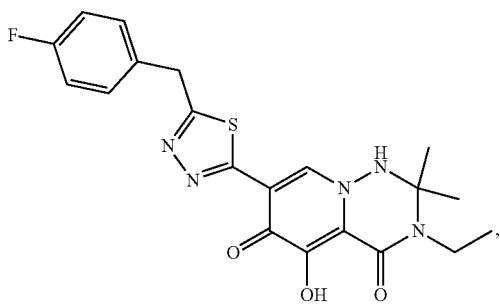
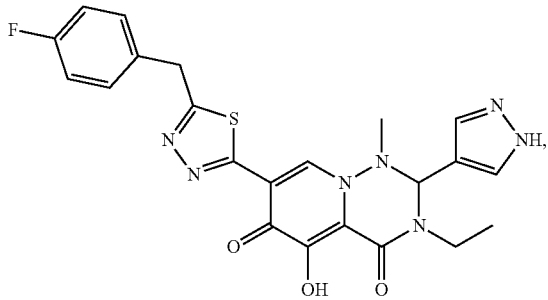
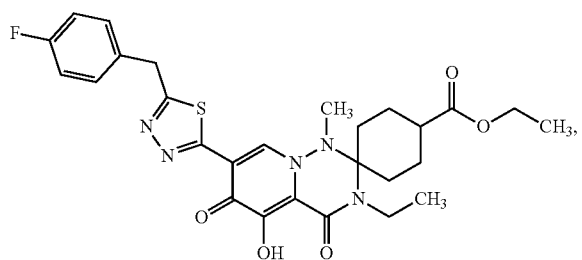
162
-continued
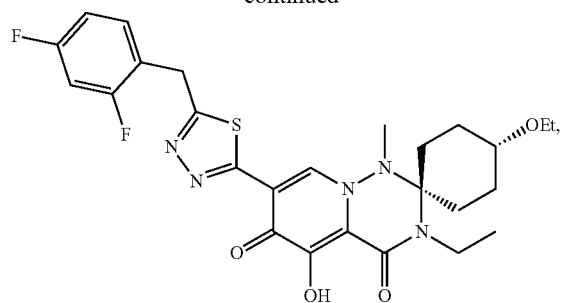
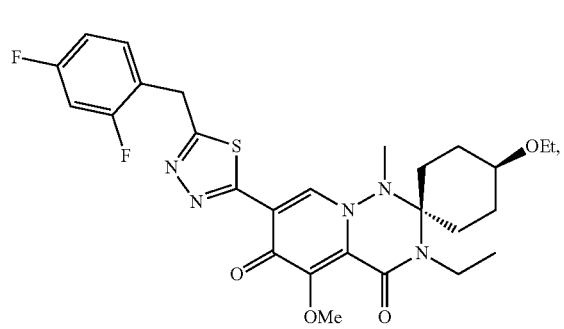
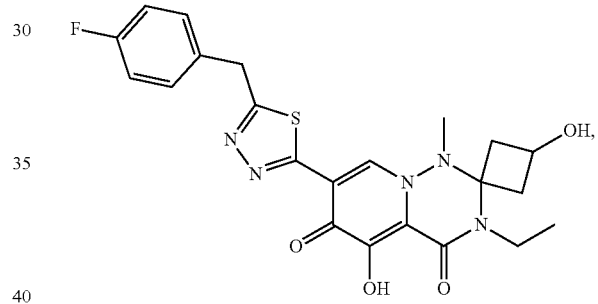
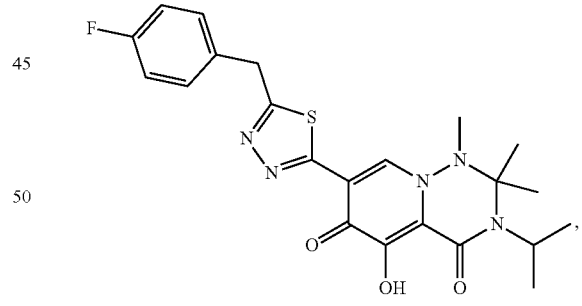
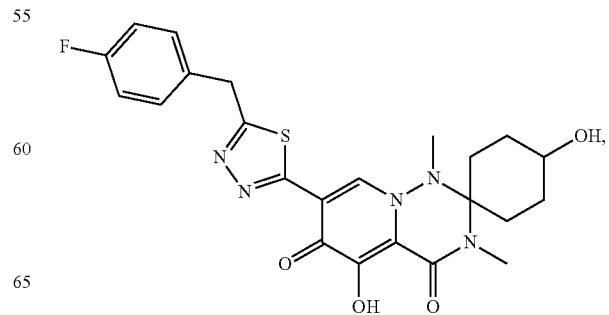

163
-continued
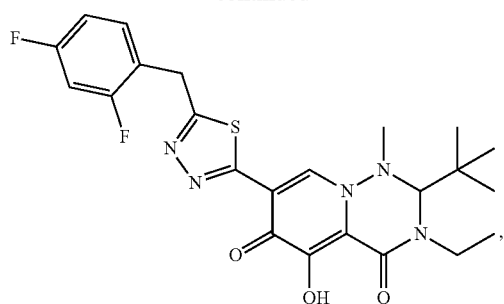
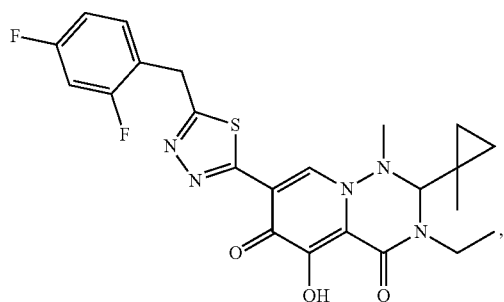
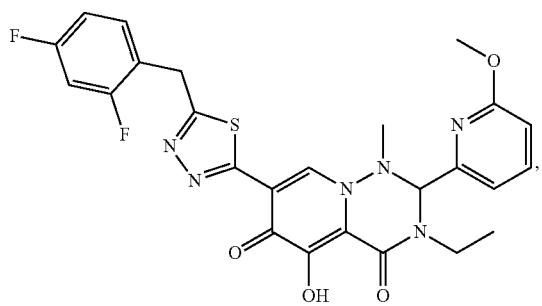
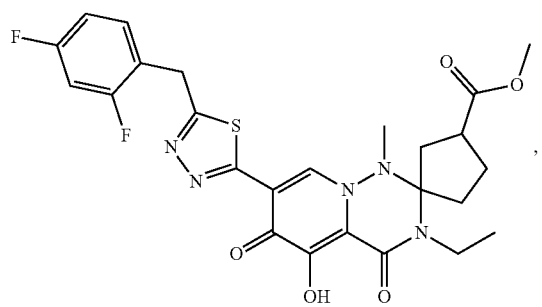
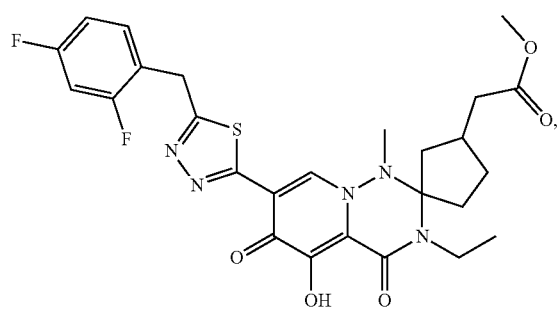
164
-continued
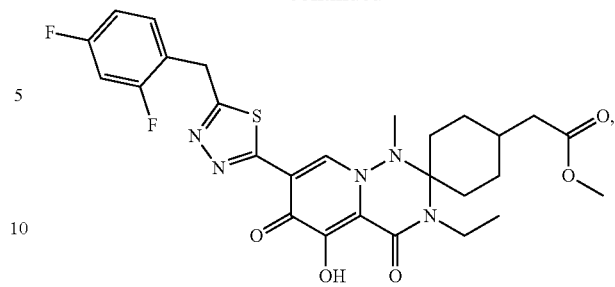
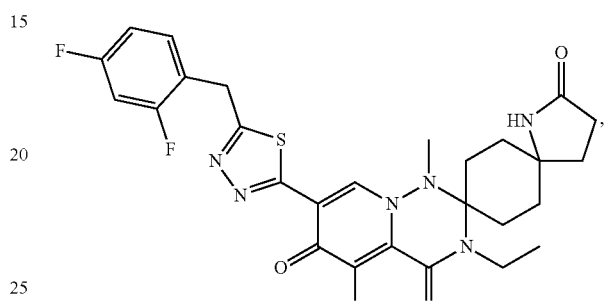
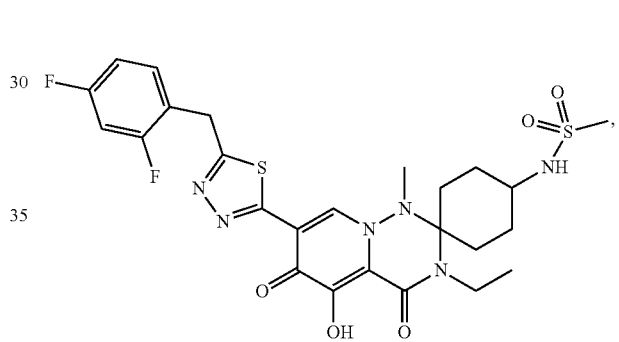
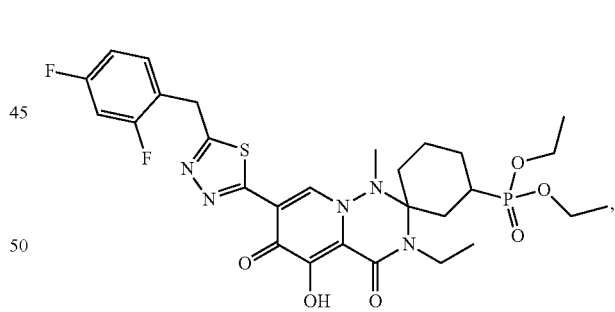
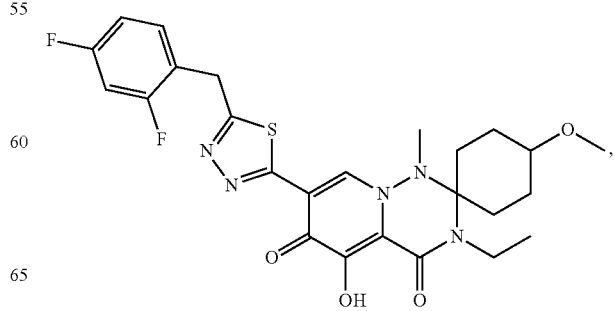

165
-continued
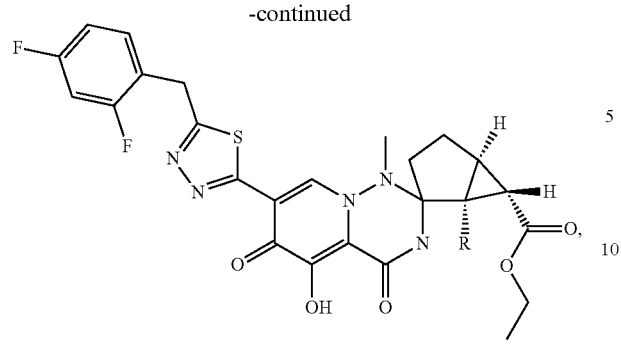
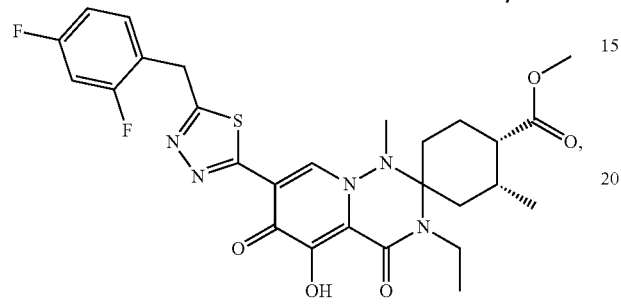
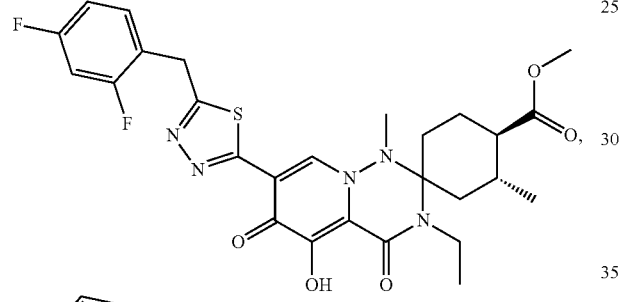
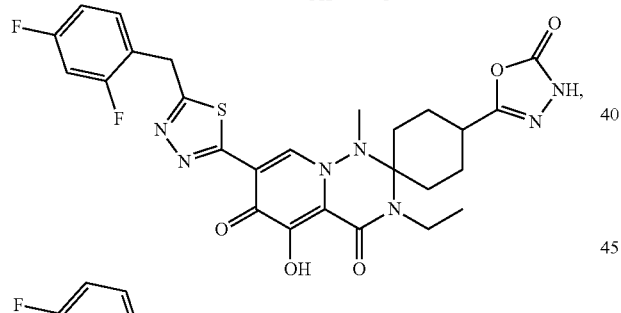
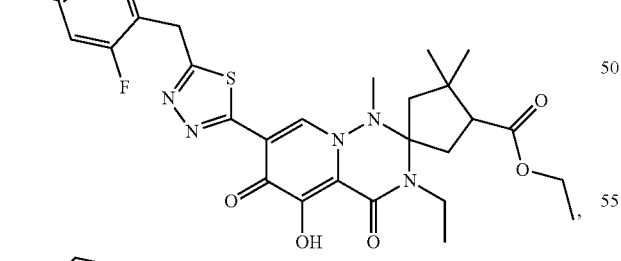
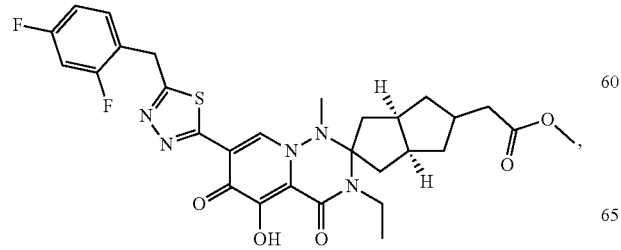
166
-continued
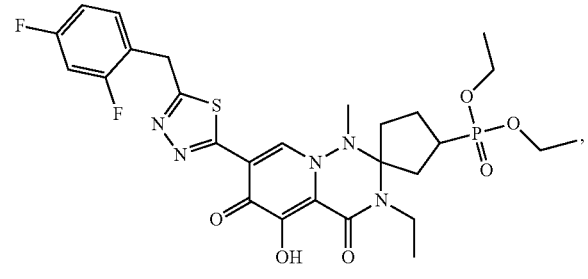
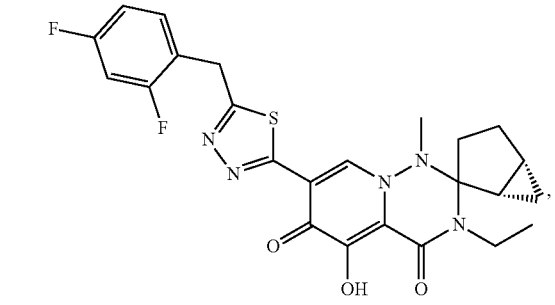
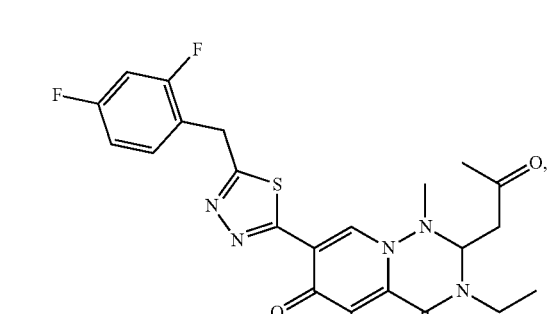
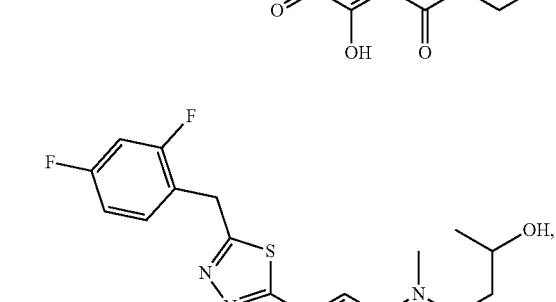
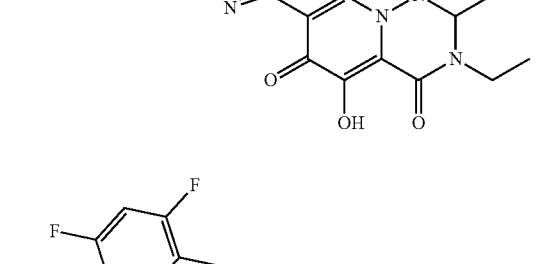
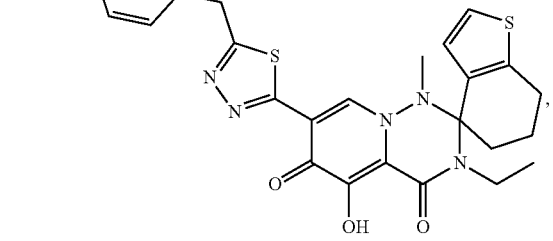

167
-continued
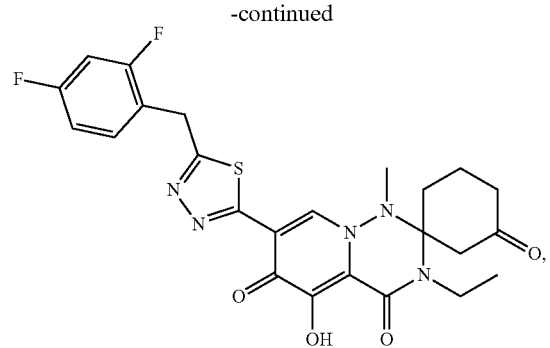
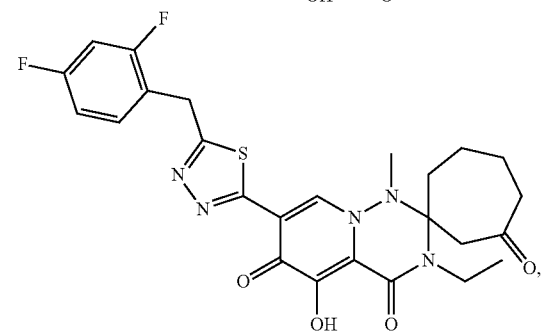
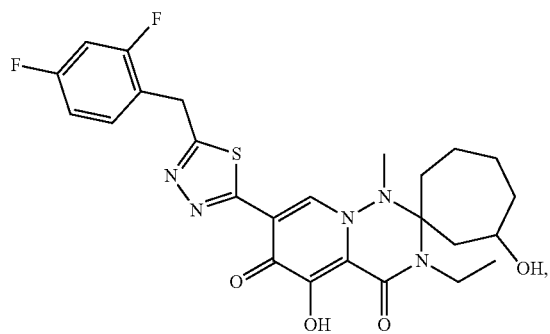
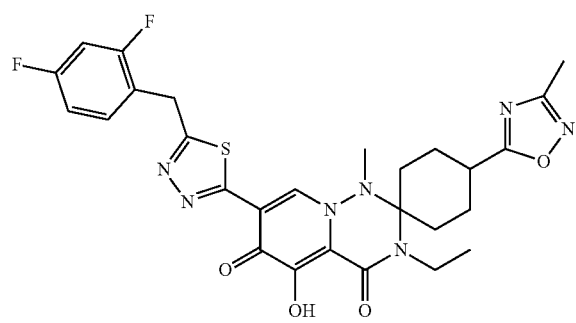
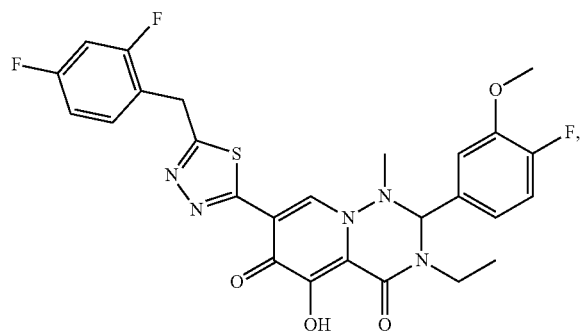
168
-continued
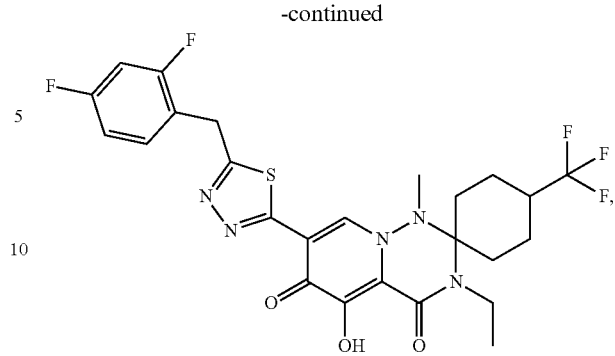
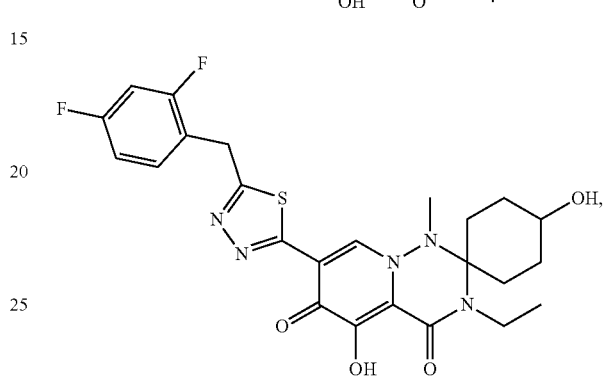
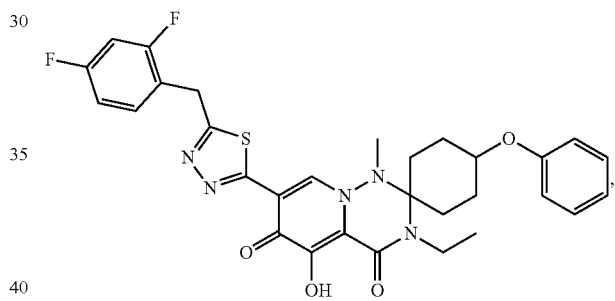
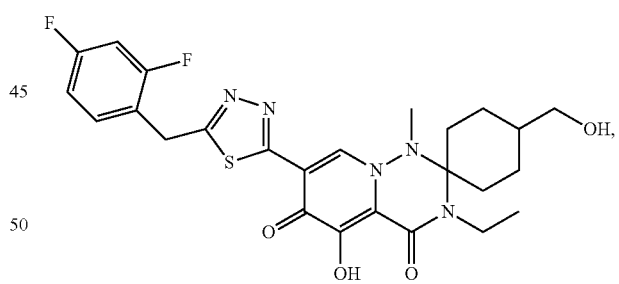
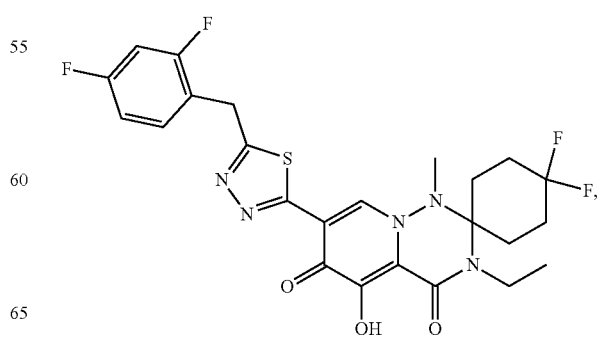

169
-continued
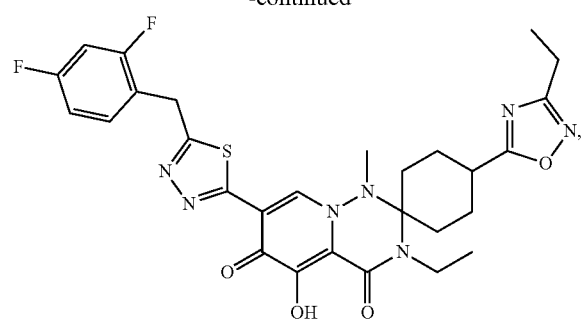
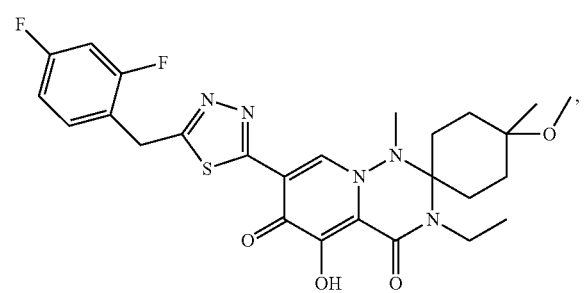
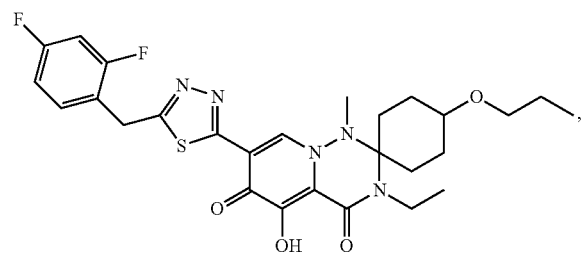
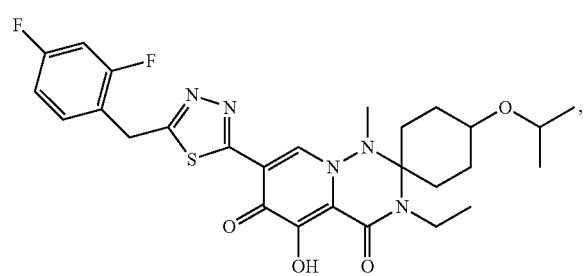
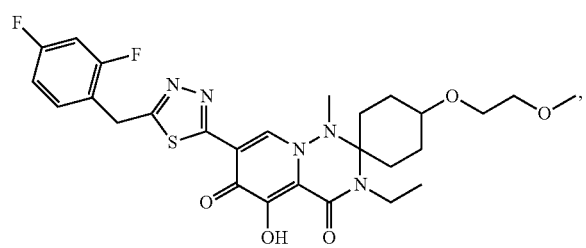
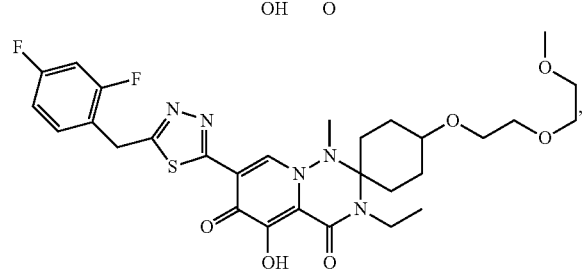
170
-continued
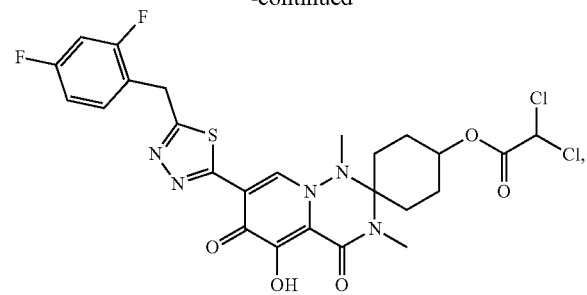
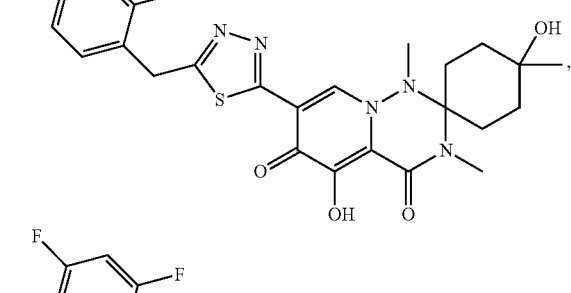
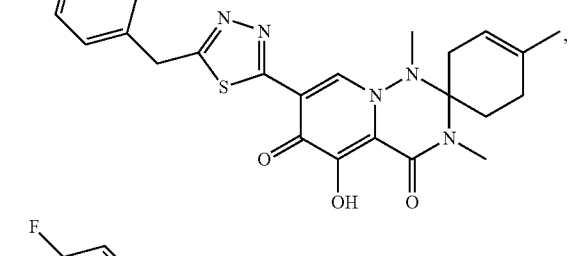
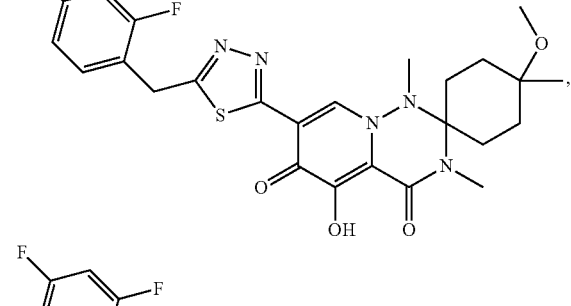
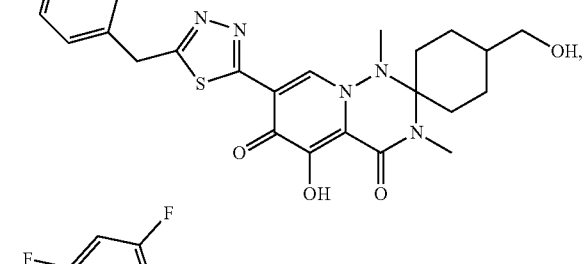
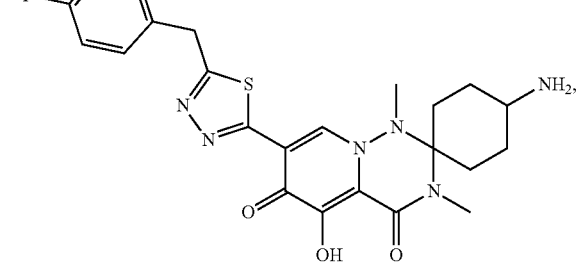

171
-continued
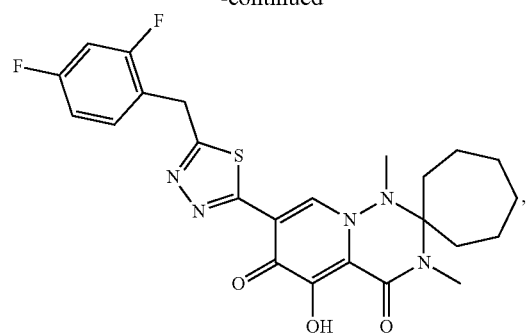
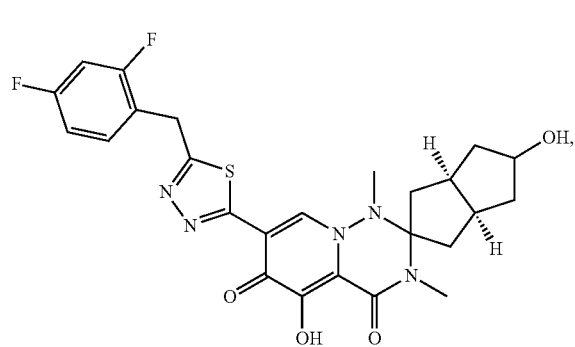
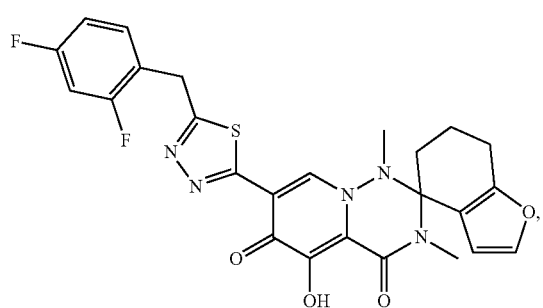
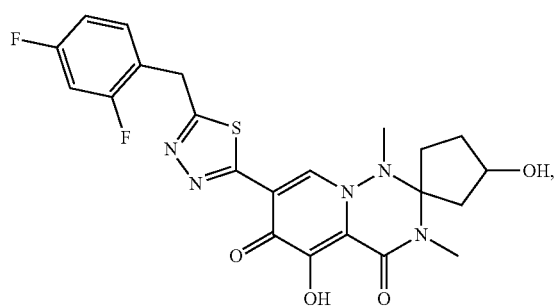
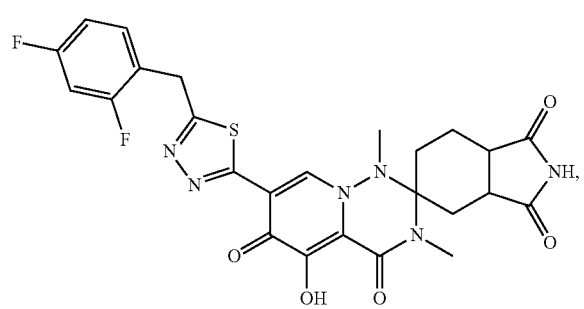
172
-continued
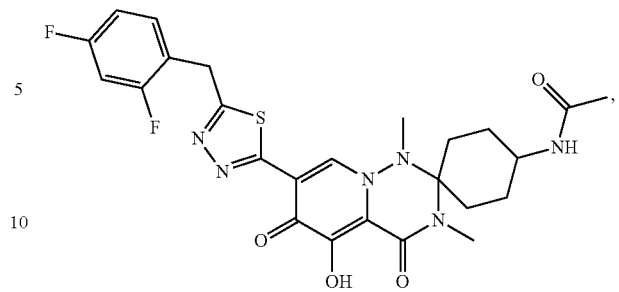
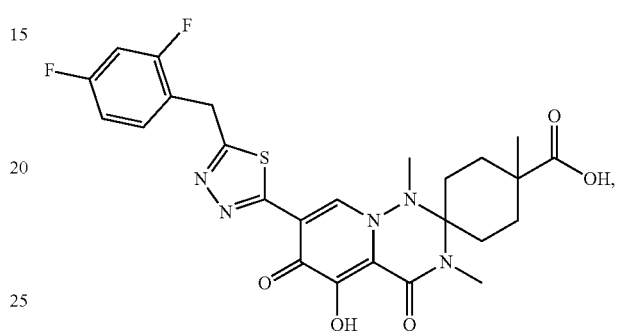
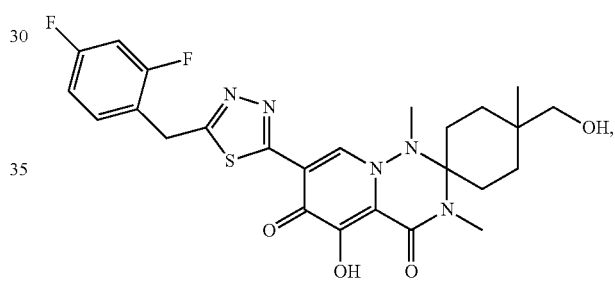
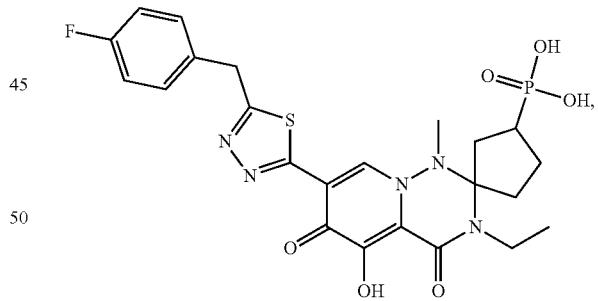
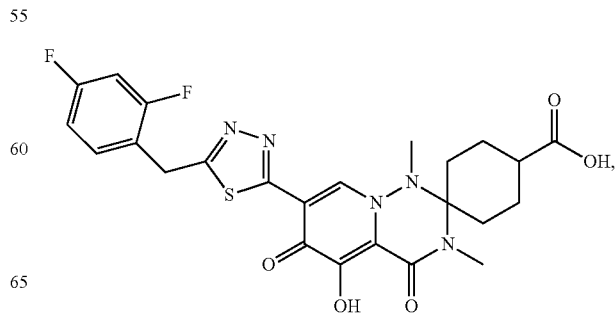

173
-continued
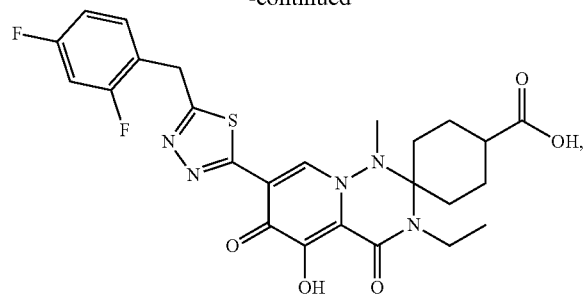
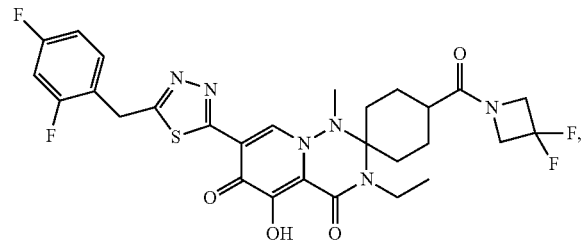
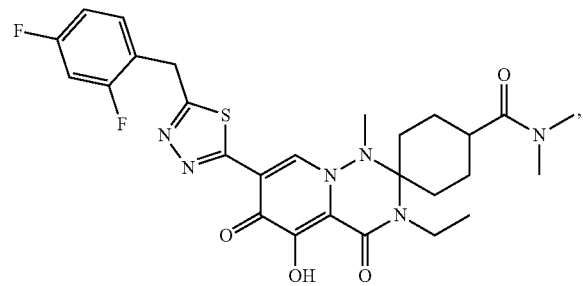
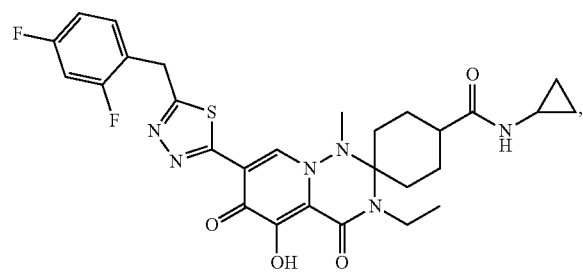
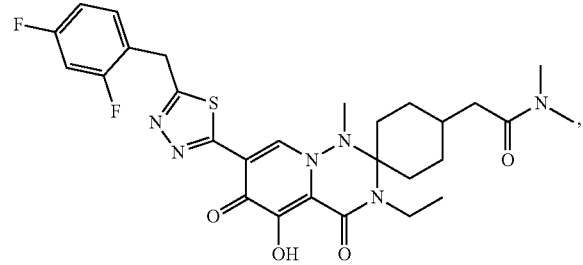
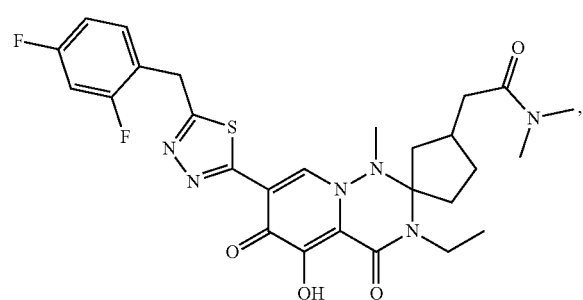
174
-continued
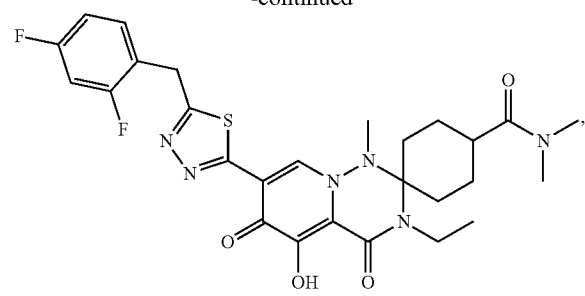
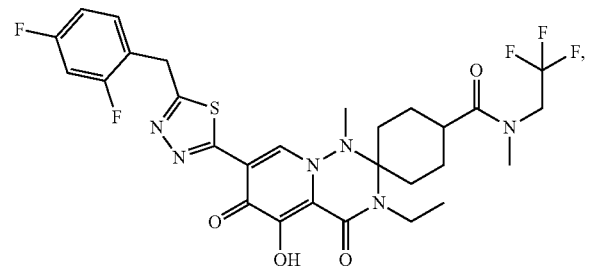
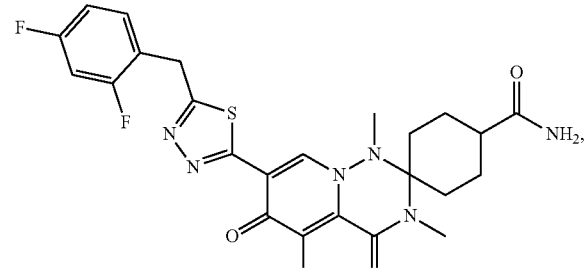
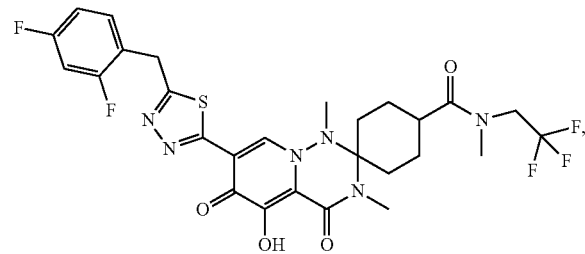
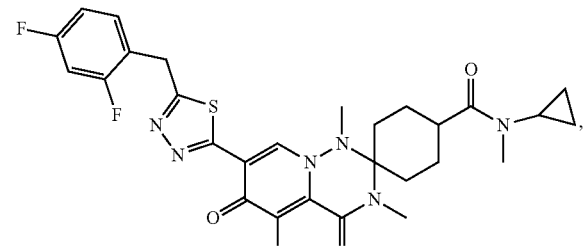
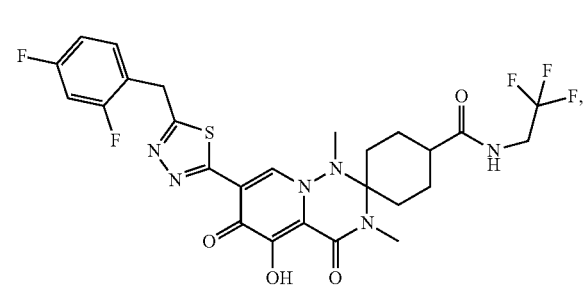

175
-continued
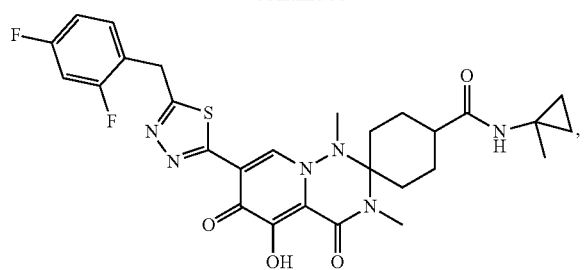
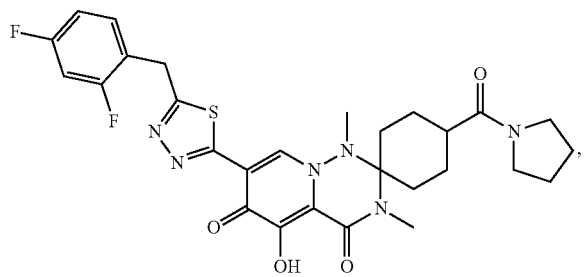
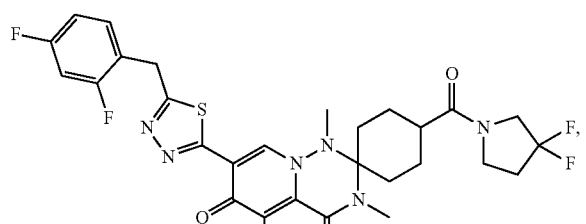
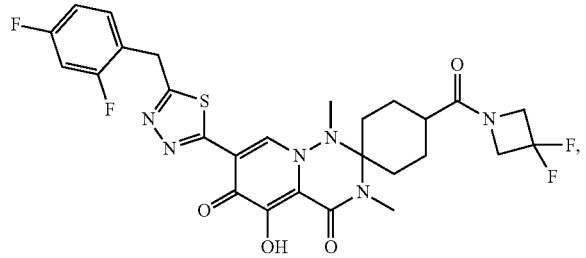
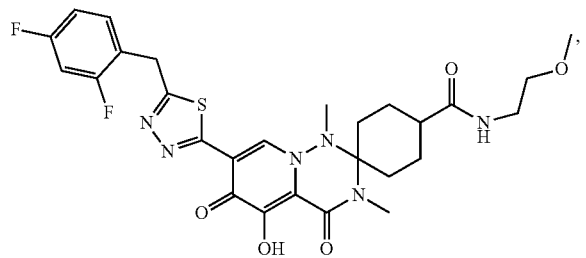
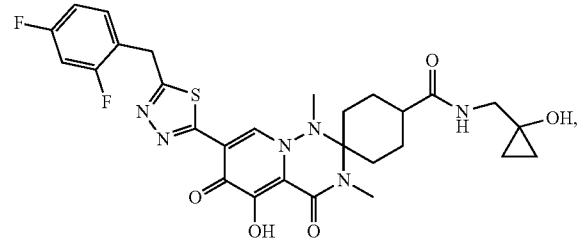
176
-continued
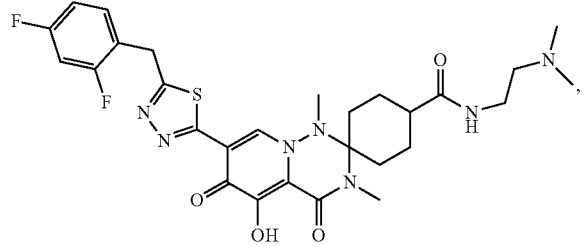
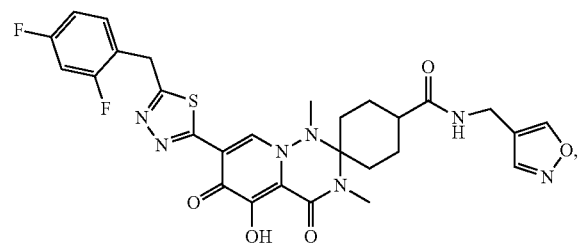
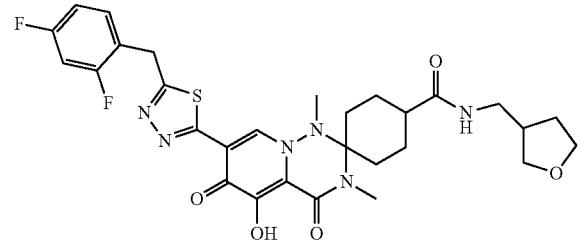
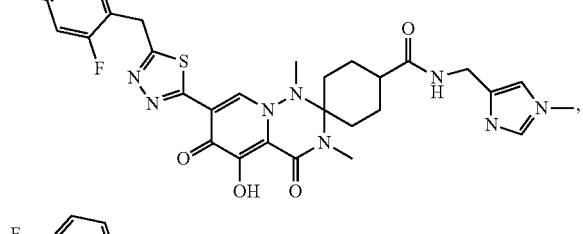
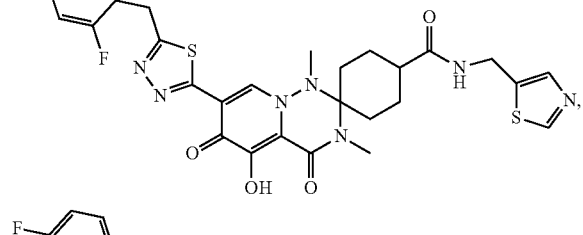
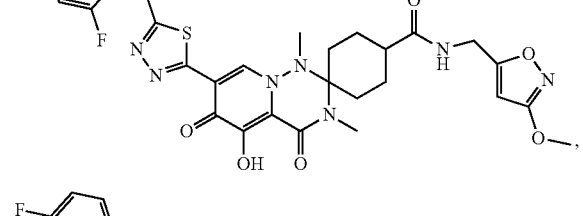
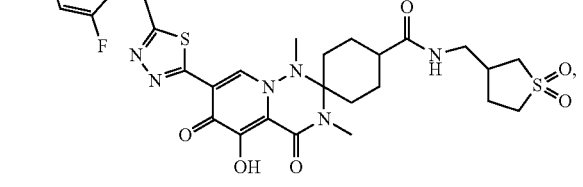

177
-continued
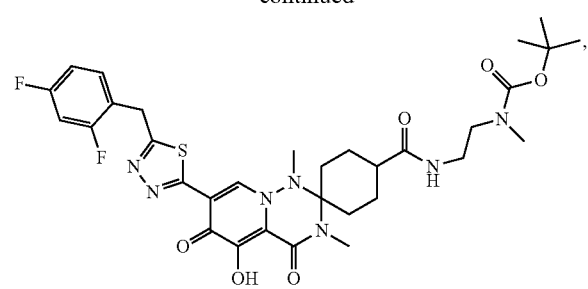
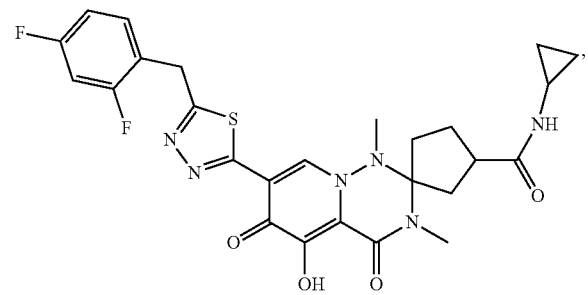
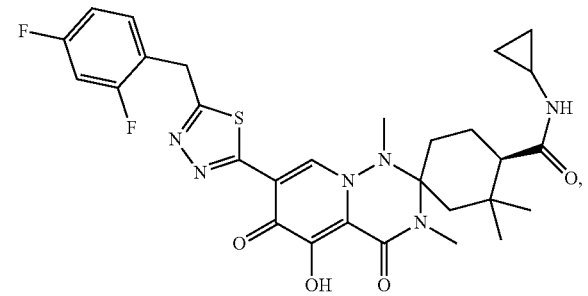
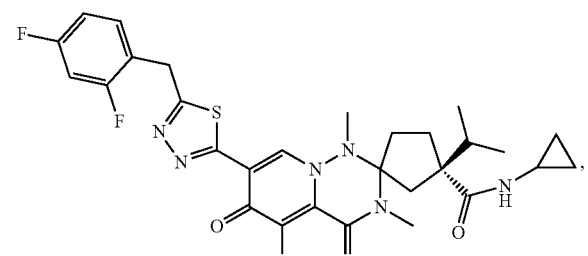
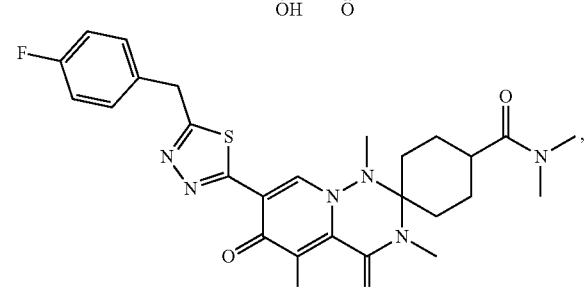
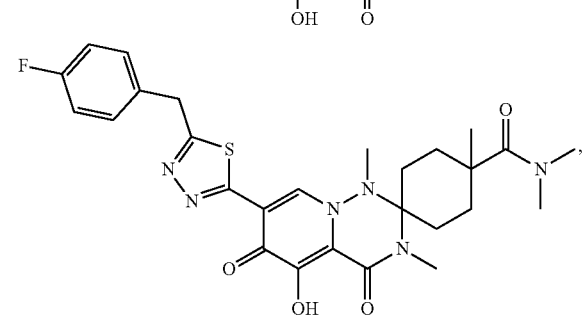
178
-continued
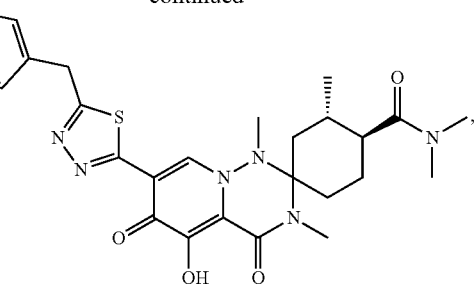
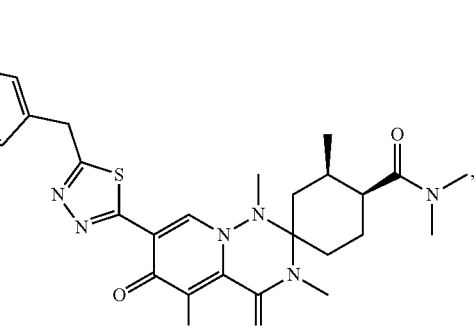
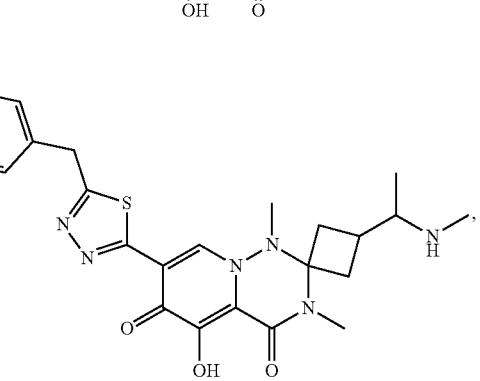
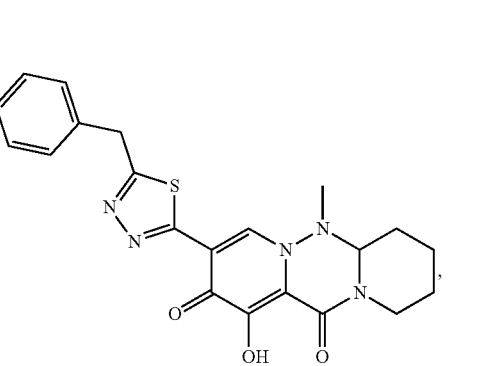
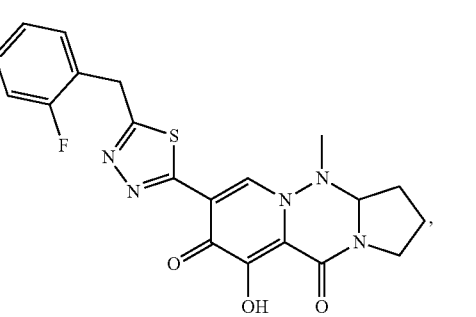

179
-continued
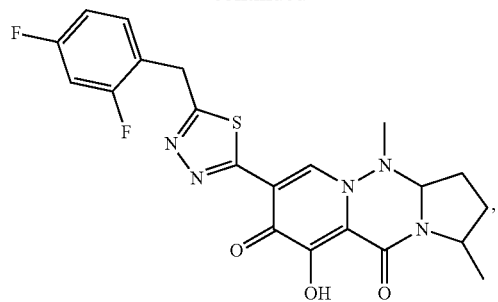
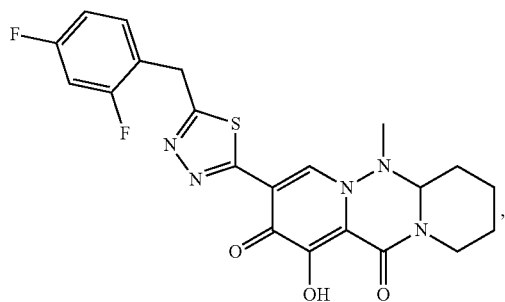
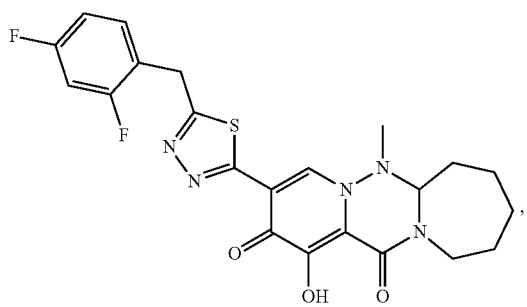
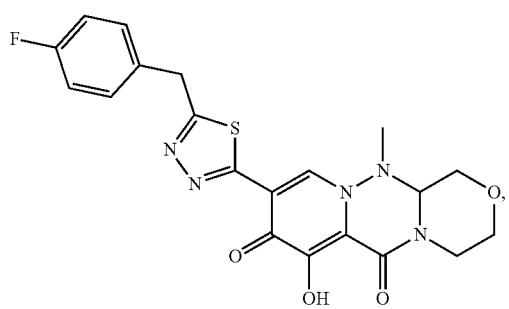
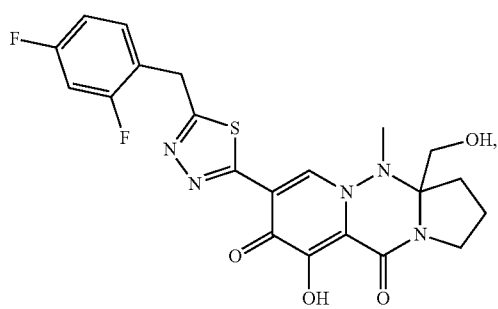
180
-continued
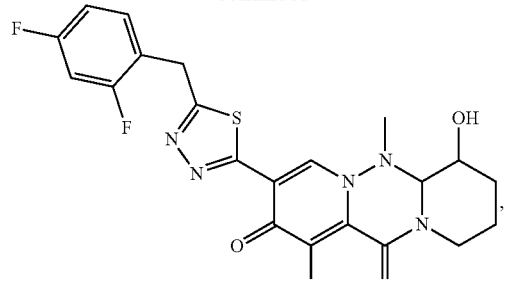
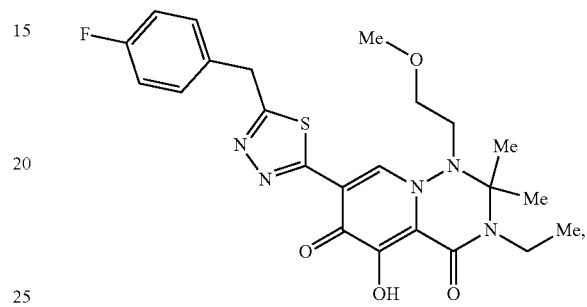
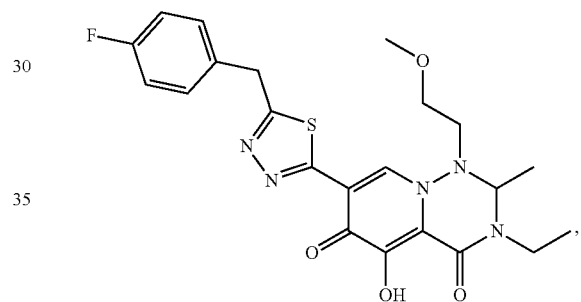
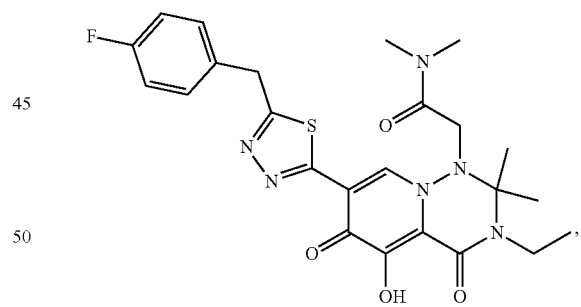
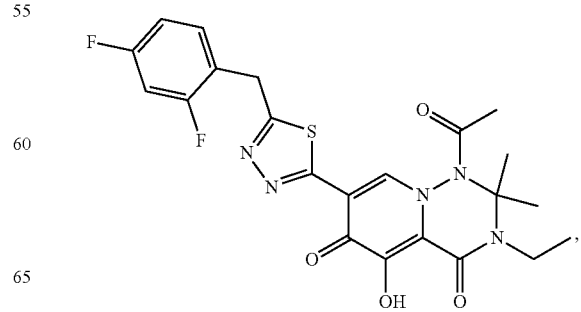

181
-continued
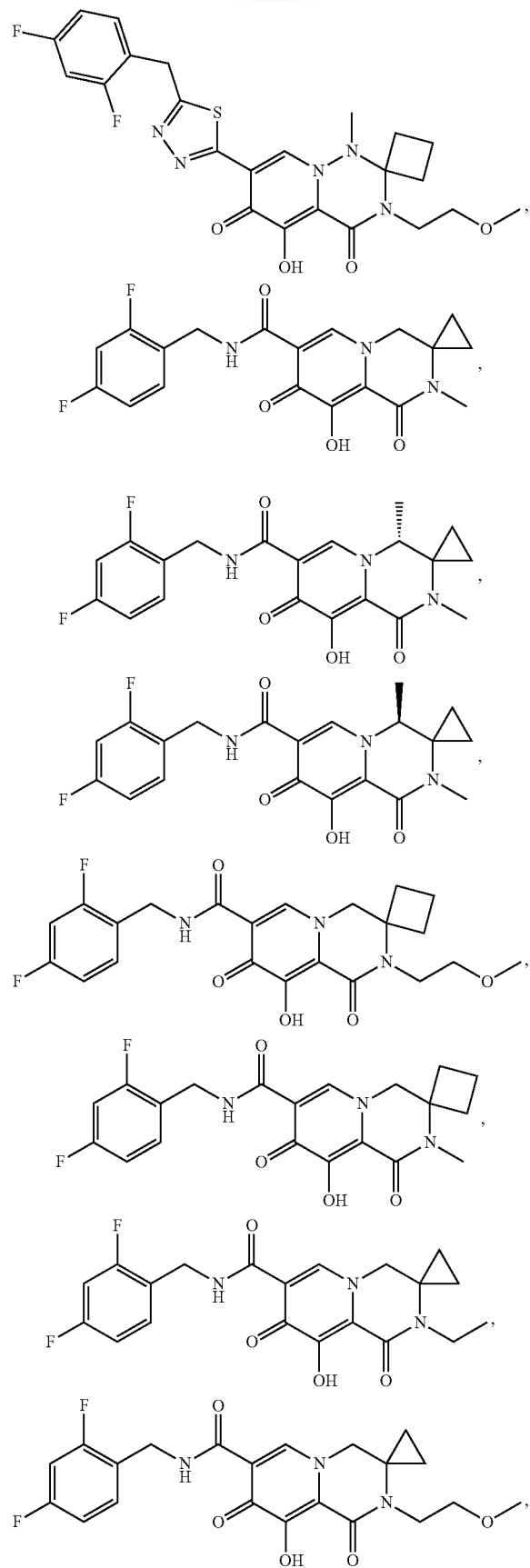
182
-continued
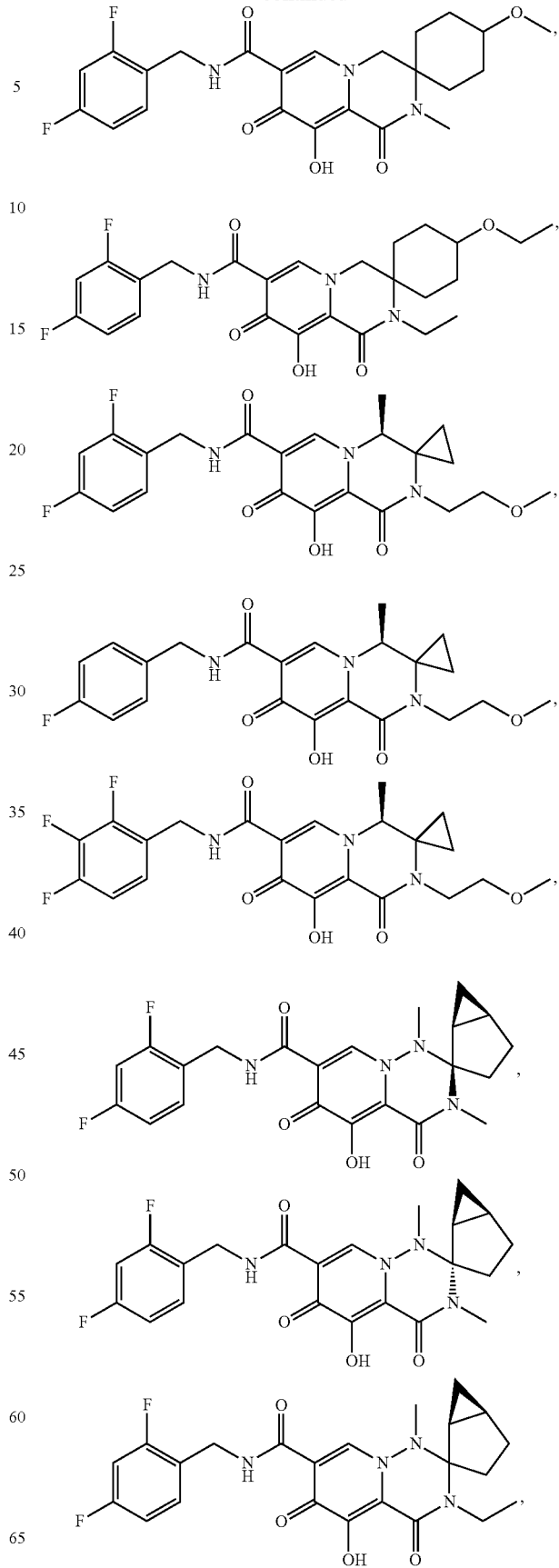

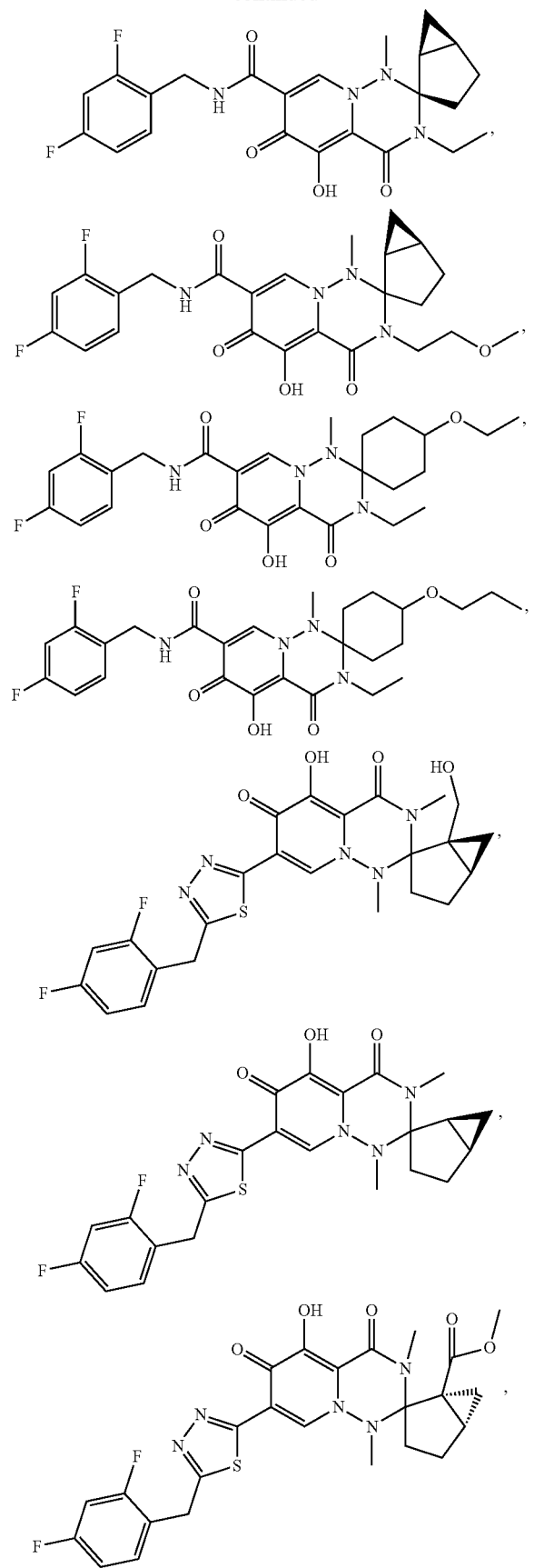
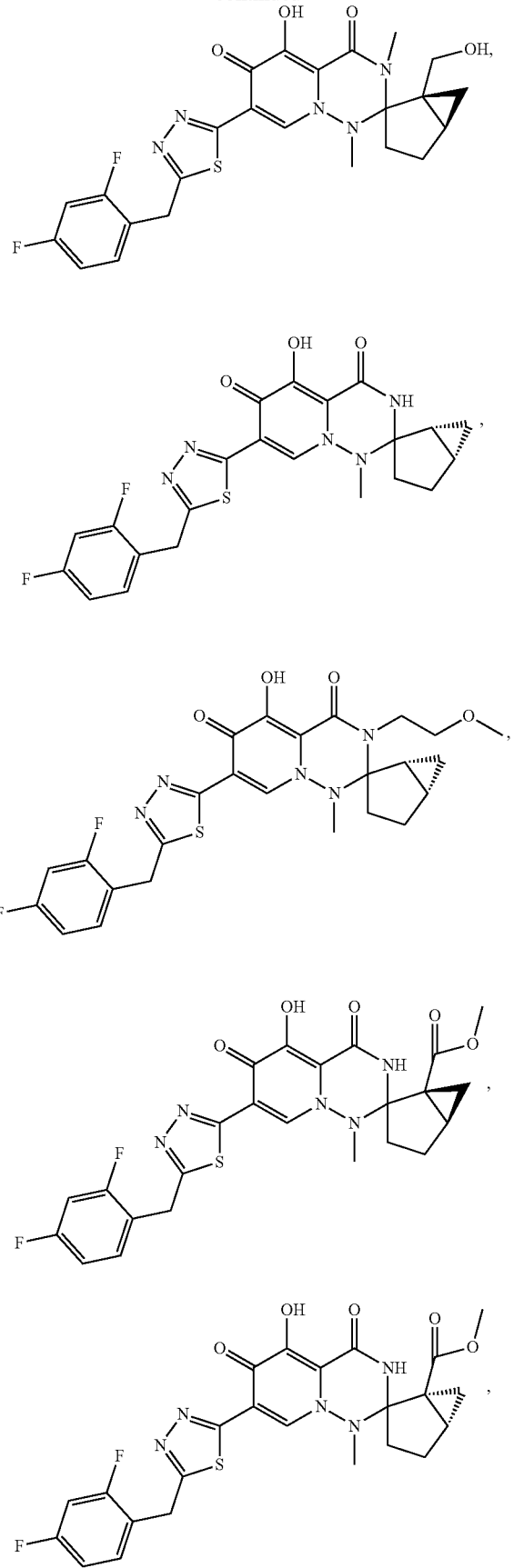

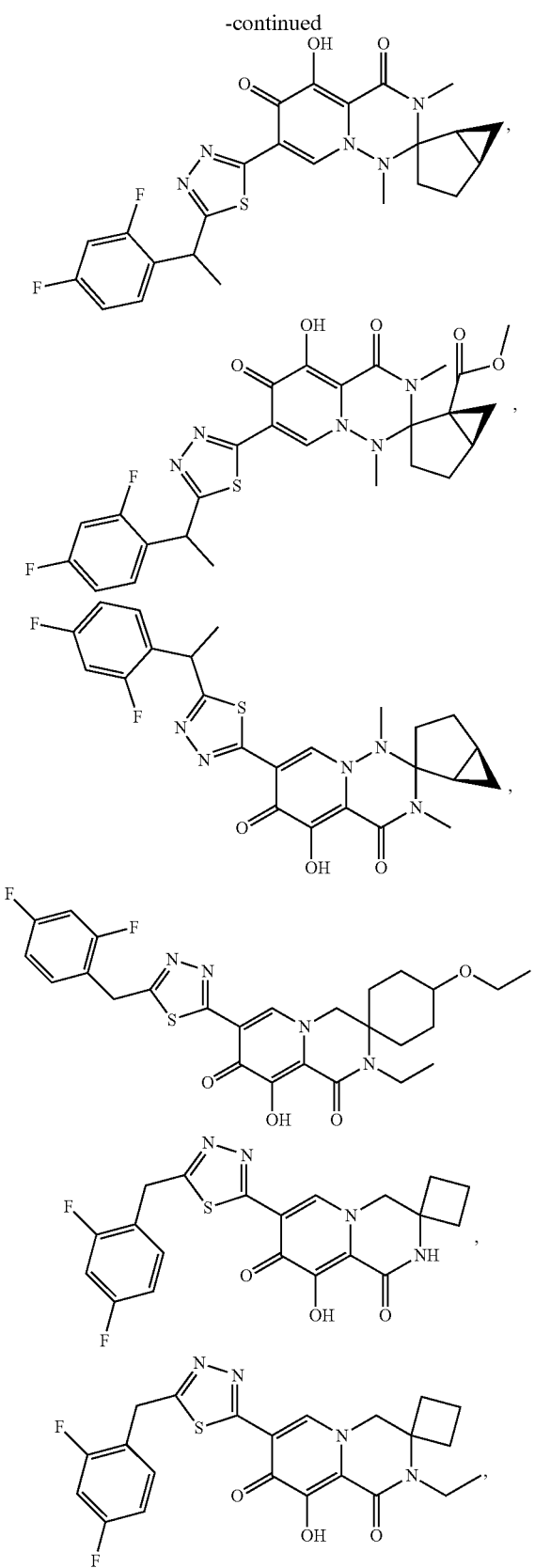

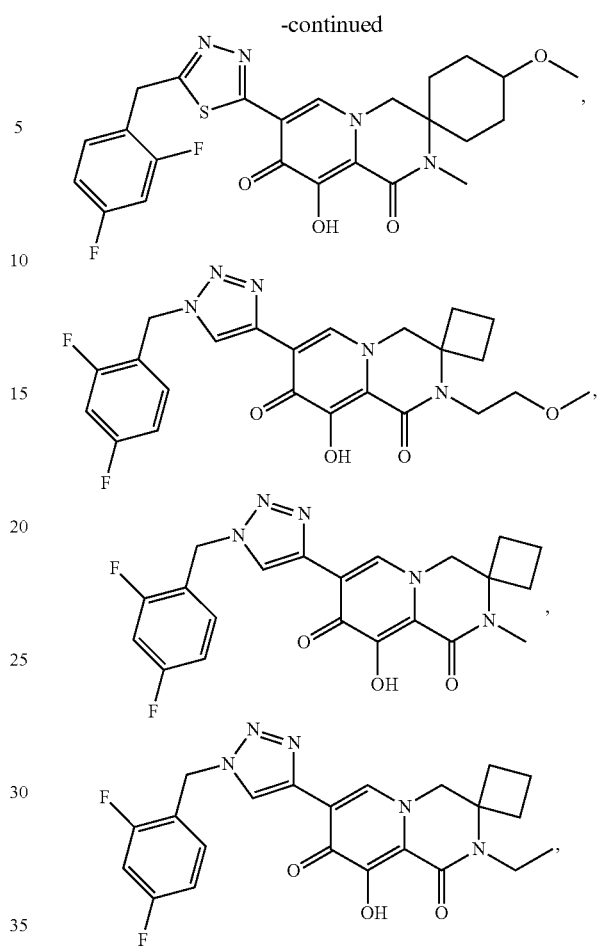

or a pharmaceutically acceptable salt thereof.

15. A pharmaceutical composition comprising an effective amount of a compound according to claim 1, or a pharmaceutically acceptable salt thereof, and a pharmaceutically acceptable carrier.

16. The pharmaceutical composition of claim 15, further comprising one or more additional therapeutic agents selected from raltegravir, lamivudine, abacavir, ritonavir, dolutegravir, arunavir, atazanavir, emtricitabine, tenofovir, elvitegravir, rilpivirine and lopinavir.

17. A method for the inhibition of HIV integrase in a subject in need thereof which comprises administering to the subject an effective amount of the compound according to claim 1, or a pharmaceutically acceptable salt thereof.

18. A method for the treatment of infection by HIV or for the treatment or delay in the onset or progression of AIDS in a subject in need thereof, which comprises administering to the subject an effective amount of the compound according to claim 1, or a pharmaceutically acceptable salt thereof.

19. The method of claim 18, further comprising administering to the subject one or more additional therapeutic agents selected from raltegravir, abacavir, lamivudine, ritonavir and lopinavir, wherein the amounts administered of the compound of claim 1 and the one or more additional therapeutic agents, are together effective to treat infection by HIV or to treat, or delay the onset or progression of AIDS.

\* \* \* \* \*